US012583920B2

(12) United States Patent
Strickland et al.

(10) Patent No.: US 12,583,920 B2
(45) Date of Patent: Mar. 24, 2026

(54) COMPOSITIONS AND METHODS FOR TREATMENT AND PREVENTION OF ALZHEIMER'S DISEASE

(71) Applicants: University of Maryland, Baltimore, Baltimore, MD (US); The General Hospital Corporation, Boston, MA (US)

(72) Inventors: Dudley K. Strickland, Brookeville, MD (US); Joanna Cooper, Baltimore, MD (US); Selen M. Catania, Brookeville, MD (US); Mary M. Migliorini, Derwood, MD (US); Brian Hampton, Gaithersburg, MD (US); Bradley T. Hyman, Madison, NH (US); Aurelien Lathuiliere, Cambridge, MA (US)

(73) Assignees: UNIVERSITY OF MARYLAND, BALTIMORE, Baltimore, MD (US); THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 17/712,167

(22) Filed: Apr. 3, 2022

(65) Prior Publication Data

US 2022/0332813 A1     Oct. 20, 2022

Related U.S. Application Data

(60) Provisional application No. 63/170,294, filed on Apr. 2, 2021.

(51) Int. Cl.
| | |
|---|---|
| *C07K 16/28* | (2006.01) |
| *A61P 25/28* | (2006.01) |
| *A61P 35/00* | (2006.01) |
| *C07H 21/02* | (2006.01) |
| *C07K 14/705* | (2006.01) |
| *C12N 15/113* | (2010.01) |
| *A61K 38/00* | (2006.01) |

(52) U.S. Cl.
CPC .............. *C07K 16/28* (2013.01); *A61P 25/28* (2018.01); *A61P 35/00* (2018.01); *C07H 21/02* (2013.01); *C07K 14/705* (2013.01); *C12N 15/1138* (2013.01); *A61K 38/00* (2013.01); *C07K 2317/76* (2013.01); *C12N 2310/14* (2013.01); *C12N 2320/32* (2013.01); *C12N 2320/51* (2013.01)

(58) Field of Classification Search
CPC ....... A61P 25/28; C07K 16/28; C07K 14/705; C07K 2317/76; A61K 38/177; A61K 38/18
See application file for complete search history.

(56) References Cited

U.S. PATENT DOCUMENTS 9,376,481 B2 *    6/2016    Gonias ............... A61K 38/1709

FOREIGN PATENT DOCUMENTS

WO        WO-2011157275 A1 *  12/2011    ......... A61K 39/3955

OTHER PUBLICATIONS

Li et al., Int J Med Sci, 2022, 19(4):659-668.*
Young et al, Cell Stem Cell, 2015, 16(4):373-385.*
Deinhardt, Nature, 2020, 580: 326-327.*
Pluta et al., In: Alzheimer's Disease: Drug Discovery, Huang X (Editor), Exon Publications, Brisbane, Australia, 2020, pp. 69-82.*
Cummings et al., Alzheimer's & Dementia: Translational Research & Clinical Interventions, 2019, 5: 272-293.*
Imbimbo et al., Expert Opinion on Investigational Drugs, published online Jul. 26, 2020, pp. 1-15.*
Madav et al., Brain Research Bulletin, 2019, 146: 171-184.*

* cited by examiner

*Primary Examiner* — Hong Sang
(74) *Attorney, Agent, or Firm* — Nevrivy Patent Law Group P.L.L.C.

(57)         ABSTRACT

The present invention provides methods and compositions for reducing internalization and/or trafficking of tau in neuronal cells comprising contacting the cells with an effective amount of an LRP1 and/or SorLA antagonist. The invention further provides a method of treating or preventing Alzheimer's disease in a subject in need thereof, comprising administering to the subject an effective amount of an LRP1 and/or SorLA antagonist.

9 Claims, 17 Drawing Sheets

Specification includes a Sequence Listing.

A.

B.

CHO WT Internalized

CHO 13-5-1 Internalized a b c a b (a)

(b)

(c)

SEQUENCE LISTING

```
<160> NUMBER OF SEQ ID NOS: 8

<210> SEQ ID NO 1
<211> LENGTH: 14923
<212> TYPE: DNA
<213> ORGANISM: Homo sapiens

<400> SEQUENCE: 1
acttcagtcc ggggaacagc ggtgcgagct ccaggcccat gcactgagga ggcggaaaca        60
aggggagccc ccagagctcc atcaagcccc ctccaaaggc tcccctaccc ggtccacgcc       120
ccccaccccc cctccccgcc tcctcccaat tgtgcatttt tgcagccgga ggcggctccg       180
agatggggct gtgagcttcg cccgggggagg gggaaagagc agcgaggagt gaagcggggg       240
ggtggggtga agggtttgga tttcggggca gggggcgcac ccccgtcagc aggccctccc       300
caaggggctc ggaactctac ctcttcaccc acgcccctgg tgcgctttgc cgaaggaaag       360
aataagaaca gagaaggagg aggggggaaag gaggaaaagg gggacccccc aactgggggg       420
ggtgaaggag agaagtagca ggaccagagg ggaaggggct gctgcttgca tcagcccaca       480
ccatgctgac cccgccgttg ctcctgctgc tgcccctgct ctcagctctg gtcgcggcgg       540
ctatcgacgc ccctaagact tgcagcccca agcagtttgc ctgcagagat caaataacct       600
gtatctcaaa gggctggcgg tgcgacggtg agagggactg cccagacgga tctgacgagg       660
cccctgagat ttgtccacag agtaaggccc agcgatgcca gccaaacgag cataactgcc       720
tgggtactga gctgtgtgtt cccatgtccc gcctctgcaa tggggtccag gactgcatgg       780
acggctcaga tgaggggccc cactgccgag agctccaagg caactgctct cgcctgggct       840
gccagcacca ttgtgtcccc acactcgatg ggcccacctg ctactgcaac agcagctttc       900
agcttcaggc agatggcaag acctgcaaag attttgatga gtgctcagtg tacggcacct       960
gcagccagct atgcaccaac acagacggct ccttcatatg tggctgtgtt gaaggatacc      1020
tcctgcagcc ggataaccgc tcctgcaagg ccaagaacga gccagtagac cggcccctg       1080 tgctgttgat agccaactcc cagaacatct tggccacgta cctgagtggg gcccaggtgt      1140
ctaccatcac acctacgagc acgcggcaga ccacagccat ggacttcagc tatgccaacg      1200
agaccgtatg ctgggtgcat gttgggggaca gtgctgctca gacgcagctc aagtgtgccc      1260
gcatgcctgg cctaaagggc ttcgtggatg agcacaccat caacatctcc ctcagtctgc      1320
accacgtgga acagatggcc atcgactggc tgacaggcaa cttctacttt gtggatgaca      1380
tcgatgatag gatctttgtc tgcaacagaa atggggacac atgtgtcaca ttgctagacc      1440
tggaactcta caaccccaag ggcattgccc tggaccctgc catggggaag gtgttttca       1500 ctgactatgg gcagatccca aaggtggaac gctgtgacat ggatgggcag aaccgcacca      1560
agctcgtcga cagcaagatt gtgtttcctc atggcatcac gctggacctg gtcagccgcc      1620
```

-continued

```
ttgtctactg ggcagatgcc tatctggact atattgaagt ggtggactat gagggcaagg      1680
gccgccagac catcatccag ggcatcctga ttgagcacct gtacggcctg actgtgtttg      1740
agaattatct ctatgccacc aactcggaca atgccaatgc ccagcagaag acgagtgtga      1800
tccgtgtgaa ccgctttaac agcaccgagt accaggttgt cacccgggtg gacaagggtg      1860
gtgccctcca catctaccac cagaggcgtc agccccgagt gaggagccat gcctgtgaaa      1920
acgaccagta tgggaagccg ggtggctgct ctgacatctg cctgctggcc aacagccaca      1980
aggcgcggac ctgccgctgc cgttccggct tcagcctggg cagtgacggg aagtcatgca      2040
agaagccgga gcatgagctg ttcctcgtgt atggcaaggg ccggccaggc atcatccggg      2100
gcatggatat ggggggccaag gtcccggatg agcacatgat ccccattgaa aacctcatga      2160 accccccgagc cctggacttc cacgctgaga ccggcttcat ctactttgcc gacaccacca      2220
gctacctcat tggccgccag aagattgatg cactgagcg ggagaccatc ctgaaggacg      2280
gcatccacaa tgtggagggt gtggccgtgg actggatggg agacaatctg tactggacgg      2340
acgatgggcc caaaaagaca atcagcgtgg ccaggctgga gaaagctgct cagacccgca      2400
agactttaat cgagggcaaa atgacacacc ccagggctat tgtggtggat ccactcaatg      2460
ggtggatgta ctggacagac tgggaggagg accccaagga cagtcggcgt gggcggctgg      2520
agagggcgtg gatggatggc tcacaccgag acatctttgt cacctccaag acagtgcttt      2580
ggcccaatgg gctaagcctg gacatcccgg ctgggcgcct ctactgggtg gatgccttct      2640
acgaccgcat cgagacgata ctgctcaatg gcacagaccg gaagattgtg tatgaaggtc      2700
ctgagctgaa ccacgccttt ggcctgtgtc accatggcaa ctacctcttc tggactgagt      2760
atcggagtgg cagtgtctac cgcttggaac ggggtgtagg aggcgcaccc cccactgtga      2820
cccttctgcg cagtgagcgg cccccatct ttgagatccg aatgtatgat gcccagcagc      2880
agcaagttgg caccaacaaa tgccgggtga acaatggcgg ctgcagcagc ctgtgcttgg      2940
ccacccctgg gagccgccag tgcgcctgtg ctgaggacca ggtgttggac gcagacggcg      3000
tcacttgctt ggcgaaccca tcctacgtgc ctccacccca gtgccagcca ggcgagtttg      3060
cctgtgccaa cagccgctgc atccaggagc gctggaagtg tgacggagac aacgattgcc      3120
tggacaacag tgatgaggcc ccagccctct gccatcagca cacctgcccc tcggaccgat      3180
tcaagtgcga gaacaaccgg tgcatcccca accgctggct ctgcgacggg acaatgact      3240 gtgggaacag tgaagatgag tccaatgcca cttgttcagc ccgcacctgc cccccaacc      3300 agttctcctg tgccagtggc cgctgcatcc ccatctcctg gacgtgtgat ctggatgacg      3360
actgtgggga ccgctctgat gagtctgctt cgtgtgccta tcccacctgc ttccccctga      3420
ctcagtttac ctgcaacaat ggcagatgta tcaacatcaa ctggagatgc gacaatgaca      3480
atgactgtgg ggacaacagt gacgaagccg gctgcagcca ctcctgttct agcacccagt      3540
tcaagtgcaa cagcgggcgt tgcatccccg agcactggac ctgcgatggg acaatgact      3600 gcggagacta cagtgatgag acacacgcca actgcaccaa ccaggccacg aggcccctg      3660 gtggctgcca cactgatgag ttccagtgcc ggctggatgg actatgcatc ccctgcggt      3720 ggcgctgcga tggggacact gactcatgg actccagcga tgagaagagc tgtgagggag      3780
tgacccacgt ctgcgatccc agtgtcaagt ttggctgcaa ggactcagct cggtgcatca      3840
gcaaagcgtg ggtgtgtgat ggcgacaatg actgtgagga taactcggac gaggagaact      3900
gcgagtccct ggcctgcagg ccaccctcgc acccttgtgc caacaacacc tcagtctgcc      3960
```

-continued

```
tgcccctga caagctgtgt gatggcaacg acgactgtgg cgacggctca gatgagggcg      4020
agctctgcga ccagtgctct ctgaataacg gtggctgcag ccacaactgc tcagtggcac      4080
ctggcgaagg cattgtgtgt tcctgccctc tgggcatgga gctggggccc gacaaccaca      4140
cctgccagat ccagagctac tgtgccaagc atctcaaatg cagccaaaag tgcgaccaga      4200
acaagttcag cgtgaagtgc tcctgctacg agggctgggt cctggaacct gacggcgaga      4260
gctgccgcag cctggacccc ttcaagccgt tcatcatttt ctccaaccgc catgaaatcc      4320
ggcgcatcga tcttcacaaa ggagactaca gcgtcctggt gcccggcctg cgcaacacca      4380
tcgccctgga cttccacctc agccagagcg ccctctactg gaccgacgtg gtggaggaca      4440
agatctaccg cgggaagctg ctggacaacg gagccctgac tagtttcgag gtggtgattc      4500
agtatggcct ggccacaccc gagggcctgg ctgtagactg gattgcaggc aacatctact      4560
gggtggagag taacctggat cagatcgagg tggccaagct ggatgggacc ctccggacca      4620
ccctgctggc cggtgacatt gagcacccaa gggcaatcgc actggatccc cgggatggga      4680
tcctgttttg gacagactgg gatgccagcc tgccccgcat tgaggcagcc tccatgagtg      4740
gggctgggcg ccgcaccgtg caccgggaga ccggctctgg gggctggccc aacgggctca      4800
ccgtggacta cctggagaag cgcatccttt ggattgacgc caggtcagat gccatttact      4860
cagcccgtta cgacggctct ggccacatgg aggtgcttcg gggacacgag ttcctgtcgc      4920
acccgtttgc agtgacgctg tacgggggg aggtctactg gactgactgg cgaacaaaca      4980
cactggctaa ggccaacaag tggaccggcc acaatgtcac cgtggtacag aggaccaaca      5040 cccagcccctt tgacctgcag gtgtaccacc cctcccgcca gcccatggct cccaatccct      5100
gtgaggccaa tgggggccag ggccctgct cccacctgtg tctcatcaac tacaaccgga      5160
ccgtgtcctg cgcctgcccc cacctcatga agctccacaa ggacaacacc acctgctatg      5220
agtttaagaa gttcctgctg tacgcacgtc agatggagat ccgaggtgtg gacctggatg      5280
ctccctacta caactacatc atctccttca cggtgcccga catcgacaac gtcacagtgc      5340
tagactacga tgcccgcgag cagcgtgtgt actggtctga cgtgcggaca caggccatca      5400
agcgggcctt catcaacggc acaggcgtgg agacagtcgt ctctgcagac ttgccaaatg      5460
cccacgggct ggctgtggac tgggtctccc gaaacctgtt ctggacaagc tatgacacca      5520
ataagaagca gatcaatgtg gcccggctgg atggctcctt caagaacgca gtggtgcagg      5580
gcctggagca gccccatggc cttgtcgtcc accctctgcg tgggaagctc tactggaccg      5640
atggtgacaa catcagcatg gccaacatgg atggcagcaa tcgcaccctg ctcttcagtg      5700
gccagaaggg ccccgtgggc ctggctattg acttccctga aagcaaactc tactggatca      5760
gctccgggaa ccataccatc aaccgctgca acctggatgg gagtgggctg gaggtcatcg      5820
atgccatgcg gagccagctg ggcaaggcca ccgccctggc catcatgggg gacaagctgt      5880
ggtgggctga tcaggtgtcg gaaaagatgg gcacatgcag caaggctgac ggctcgggct      5940
ccgtggtcct tcggaacagc accaccctgg tgatgcacat gaaggtctat gacgagagca      6000
tccagctgga ccataagggc accaacccct gcagtgtcaa caacggtgac tgctcccagc      6060
tctgcctgcc cacgtcagag acgacccgct cctgcatgtg cacagccggc tatagcctcc      6120
ggagtggcca gcaggcctgc gagggcgtag gttcctttct cctgtactct gtgcatgagg      6180
gaatcagggg aattcccctg gatcccaatg acaagtcaga tgccctggtc ccagtgtccg      6240
ggacctcgct ggctgtcggc atcgacttcc acgctgaaaa tgacaccatc tactgggtgg      6300
acatgggcct gagcacgatc agccgggcca agcgggacca gacgtggcgt gaagacgtgg      6360
```

```
tgaccaatgg cattggccgt gtggagggca ttgcagtgga ctggatcgca ggcaacatct    6420
actggacaga ccagggcttt gatgtcatcg aggtcgcccg gctcaatggc tccttccgct    6480
acgtggtgat ctcccagggt ctagacaagc cccgggccat caccgtccac ccggagaaag    6540
ggtacttgtt ctggactgag tggggtcagt atccgcgtat tgagcggtct cggctagatg    6600
gcacggagcg tgtggtgctg gtcaacgtca gcatcagctg gcccaacggc atctcagtgg    6660
actaccagga tgggaagctg tactggtgcg atgcacggac agacaagatt gaacggatcg    6720
acctggagac aggtgagaac cgcgaggtgg ttctgtccag caacaacatg gacatgtttt    6780
cagtgtctgt gtttgaggat ttcatctact ggagtgacag gactcatgcc aacggctcta    6840
tcaagcgcgg gagcaaagac aatgccacag actccgtgcc cctgcgaacc ggcatcggcg    6900
tccagcttaa agacatcaaa gtcttcaacc gggaccggca gaaaggcacc aacgtgtgcg    6960
cggtggccaa tggcgggtgc cagcagctgt gcctgtaccg gggccgtggg cagcgggcct    7020
gcgcctgtgc ccacgggatg ctggctgaag acggagcatc gtgccgcgag tatgccggct    7080
acctgctcta ctcagagcgc accattctca agagtatcca cctgtcggat gagcgcaacc    7140
tcaatgcgcc cgtgcagccc ttcgaggacc ctgagcacat gaagaacgtc atcgccctgg    7200
cctttgacta ccgggcaggc acctctccgg gcacccccaa tcgcatcttc ttcagcgaca    7260
tccactttgg gaacatccaa cagatcaacg acgatggctc caggaggatc accattgtgg    7320
aaaacgtggg ctccgtggaa ggcctggcct atcaccgtgg ctgggacact ctctattgga    7380
caagctacac gacatccacc atcacgcgcc acacagtgga ccagacccgc ccaggggcct    7440
tcgagcgtga ccgtcatc actatgtctg gagatgacca cccacgggcc ttcgtttttgg    7500 acgagtgcca gaacctcatg ttctggacca actggaatga gcagcatccc agcatcatgc    7560
gggcggcgct ctcgggagcc aatgtcctga cccttatcga gaaggacatc cgtacccca    7620 atggcctggc catcgaccac cgtgccgaga agctctactt ctctgacgcc accctggaca    7680
agatcgagcg gtgcgagtat gacggctccc accgctatgt gatcctaaag tcagagcctg    7740
tccacccctt cgggctggcc gtgtatgggg agcacatttt ctggactgac tgggtgcggc    7800
gggcagtgca gcgggccaac aagcacgtgg gcagcaacat gaagctgctg cgcgtggaca    7860
tcccccagca gcccatgggc atcatcgccg tggccaacga caccaacagc tgtgaactct    7920
ctccatgccg aatcaacaac ggtggctgcc aggacctgtg tctgctcact caccagggcc    7980
atgtcaactg ctcatgccga gggggccgaa tcctccagga tgacctcacc tgccgagcgg    8040
tgaattcctc ttgccgagca caagatgagt ttgagtgtgc caatggcgag tgcatcaact    8100
tcagcctgac ctgcgacggc gtcccccact gcaaggacaa gtccgatgag aagccatcct    8160
actgcaactc ccgccgctgc aagaagactt ccggcagtg cagcaatggg cgctgtgtgt    8220
ccaacatgct gtggtgcaac ggggccgacg actgtgggga tggctctgac gagatccctt    8280
gcaacaagac agcctgtggt gtgggcgagt ccgctgccg ggacgggacc tgcatcggga    8340
actccagccg ctgcaaccag tttgtggatt gtgaggacgc ctcagatgag atgaactgca    8400
gtgccaccga ctgcagcagc tacttccgcc tgggcgtgaa gggcgtgctc ttccagccct    8460
gcgagcggac ctcactctgc tacgcaccca gctgggtgtg tgatggcgcc aatgactgtg    8520
gggactacag tgatgagcgc gactgccag gtgtgaaacg ccccagatgc cctctgaatt    8580
acttcgcctg ccctagtggg cgctgcatcc ccatgagctg gacgtgtgac aaagaggatg    8640
actgtgaaca tggcgaggac gagacccact gcaacaagtt ctgctcagag gcccagtttg    8700
```

-continued

```
agtgccagaa ccatcgctgc atctccaagc agtggctgtg tgacggcagc gatgactgtg    8760
gggatggctc agacgaggct gctcactgtg aaggcaagac gtgcggcccc tcctccttct    8820
cctgccctgg cacccacgtg tgcgtccccg agcgctggct ctgtgacggt gacaaagact    8880
gtgctgatgg tgcagacgag agcatcgcag ctggttgctt gtacaacagc acttgtgacg    8940
accgtgagtt catgtgccag aaccgccagt gcatccccaa gcacttcgtg tgtgaccacg    9000
accgtgactg tgcagatggc tctgatgagt cccccgagtg tgagtacccg acctgcggcc    9060
ccagtgagtt ccgctgtgcc aatgggcgct gtctgagctc ccgccagtgg gagtgtgatg    9120
gcgagaatga ctgccacgac cagagtgacg aggctcccaa gaacccacac tgcaccagcc    9180
aagagcacaa gtgcaatgcc tcgtcacagt tcctgtgcag cagtgggcgc tgtgtggctg    9240
aggcactgct ctgcaacggc caggatgact gtggcgacag ctcggacgag cgtggctgcc    9300
acatcaatga gtgtctcagc cgcaagctca gtggctgcag ccaggactgt gaggacctca    9360
agatcggctt caagtgccgc tgtcgccctg gcttccggct gaaggacgac ggccggacgt    9420
gtgctgatgt ggacgagtgc agcaccacct tcccctgcag ccagcgctgc atcaacactc    9480
atggcagcta taagtgtctg tgtgtggagg gctatgcacc ccgcggcggc gacccccaca    9540
gctgcaaggc tgtgactgac gaggaaccgt ttctgatctt cgccaaccgg tactacctgc    9600
gcaagctcaa cctggacggg tccaactaca cgttacttaa gcagggcctg aacaacgccg    9660
ttgccttgga ttttgactac cgagagcaga tgatctactg gacagatgtg accacccagg    9720
gcagcatgat ccgaaggatg caccttaacg ggagcaatgt gcaggtccta caccgtacag    9780
gcctcagcaa ccccgatggg ctggctgtgg actgggtggg tggcaacctg tactggtgcg    9840
acaaaggccg ggacaccatc gaggtgtcca agctcaatgg ggcctatcgg acggtgctgg    9900
tcagctctgg cctccgtgag cccagggctc tggtggtgga tgtgcagaat gggtacctgt    9960
actggacaga ctggggtgac cattcactga tcggccgcat cggcatggat gggtccagcc    10020
gcagcgtcat cgtggacacc aagatcacat ggcccaatgg cctgacgctg gactatgtca    10080
ctgagcgcat ctactgggcc gacgcccgcg aggactacat tgaatttgcc agcctggatg    10140
gctccaatcg ccacgttgtg ctgagccagg acatcccgca catctttgca ctgaccctgt    10200
ttgaggacta cgtctactgg accgactggg aaacaaagtc cattaaccga gcccacaaga    10260
ccacgggcac caacaaaacg ctcctcatca gcacgctgca ccggcccatg gacctgcatg    10320
tcttccatgc cctgcgccag ccagacgtgc ccaatcaccc ctgcaaggtc aacaatggtg    10380
gctgcagcaa cctgtgcctg ctgtcccccg ggggagggca caaatgtgcc tgccccacca    10440
acttctacct gggcagcgat gggcgcacct gtgtgtccaa ctgcacggct agccagtttg    10500
tatgcaagaa cgacaagtgc atccccttct ggtggaagtg tgacaccgag gacgactgcg    10560
gggaccactc agacgagccc ccggactgcc ctgagttcaa gtgccggccc ggacagttcc    10620
agtgctccac aggtatctgc acaaaccctg ccttcatctg cgatggcgac aatgactgcc    10680
aggacaacag tgacgaggcc aactgtgaca tccacgtctg cttgcccagt cagttcaaat    10740
gcaccaacac caaccgctgt attcccggca tcttccgctg caatgggcag gacaactgcg    10800
gagatgggga ggatgagagg gactgccccg aggtgacctg cgcccccaac cagttccagt    10860
gctccattac caaacggtgc atcccccggg tctgggtctg cgaccgggac aatgactgtg    10920
tggatggcag tgatgagccc gccaactgca cccagatgac ctgtggtgtg gacgagttcc    10980
gctgcaagga ttcgggccgc tgcatcccag cgcgttggaa gtgtgacgga gaggatgact    11040 gtgggggatgg ctcggatgag cccaaggaag agtgtgatga acgcacctgt gagccatacc    11100
```

```
agttccgctg caagaacaac cgctgcgtgc ccggccgctg gcagtgcgac tacgacaacg   11160
attgcggtga caactccgat gaagagagct gcacccctcg gccctgctcc gagagtgagt   11220
tctcctgtgc caacggccgc tgcatcgcgg ggcgctggaa atgcgatgga gaccacgact   11280
gcgcggacgg ctcggacgag aaagactgca ccccccgctg tgacatggac cagttccagt   11340
gcaagagcgg ccactgcatc cccctgcgct ggcgctgtga cgcagacgcc gactgcatgg   11400
acggcagcga cgaggaggcc tgcggcactg gcgtgcggac ctgccccctg gacgagttcc   11460
agtgcaacaa caccttgtgc aagccgctgg cctggaagtg cgatggcgag gatgactgtg   11520
gggacaactc agatgagaac cccgaggagt gtgcccggtt cgtgtgccct cccaaccggc   11580
ccttccgttg caagaatgac cgcgtctgtc tgtggatcgg gcgccaatgc gatggcacgg   11640
acaactgtgg ggatgggact gatgaagagg actgtgagcc ccccacagcc cacaccaccc   11700
actgcaaaga caagaaggag tttctgtgcc ggaaccagcg ctgcctctcc tcctccctgc   11760
gctgcaacat gttcgatgac tgcgggacg gctctgacga ggaggactgc agcatcgacc   11820
ccaagctgac cagctgcgcc accaatgcca gcatctgtgg ggacgaggca cgctgcgtgc   11880
gcaccgagaa agcggcctac tgtgcctgcc gctcgggctt ccacaccgtg cccggccagc   11940
ccggatgcca agacatcaac gagtgcctgc gcttcggcac ctgctcccag ctctgcaaca   12000
acaccaaggg cggccacctc tgcagctgcg ctcggaactt catgaagacg cacaacacct   12060
gcaaggccga aggctctgag taccaggtcc tgtacatcgc tgatgacaat gagatccgca   12120
gcctgttccc cggccacccc cattcggctt acgagcaggc attccagggt gacgagagtg   12180
tccgcattga tgctatggat gtccatgtca aggctggccg tgtctattgg accaactggc   12240
acacgggcac catctcctac cgcagcctgc cacctgctgc gcctcctacc acttccaacc   12300
gccaccggcg acagattgac cggggtgtca cccacctcaa catttcaggg ctgaagatgc   12360
ccagaggcat cgccatcgac tgggtggccg gaaacgtgta ctggaccgac tcgggccgag   12420
atgtgattga ggtggcgcag atgaagggcg agaaccgcaa gacgctcatc tcgggcatga   12480
ttgacgagcc ccacgccatt gtggtggacc cactgagggg gaccatgtac tggtcagact   12540
ggggcaacca ccccaagatt gagacggcag cgatggatgg gacgcttcgg gagacactgg   12600
tgcaggacaa cattcagtgg cccacaggcc tggccgtgga ttatcacaat gagcggctgt   12660
actgggcaga cgccaagctt tcagtcatcg gcagcatccg gctcaatggc acggacccca   12720
ttgtggctgc tgacagcaaa cgaggcctaa gtcaccccctt cagcatcgac gtctttgagg   12780
attacatcta tggtgtcacc tacatcaata atcgtgtctt caagatccat aagtttggcc   12840 acagccccctt ggtcaacctg acagggggcc tgagccacgc ctctgacgtg gtcctttacc   12900
atcagcacaa gcagcccgaa gtgaccaacc catgtgaccg caagaaatgc gagtggctct   12960
gcctgctgag ccccagtggg cctgtctgca cctgtcccaa tgggaagcgg ctggacaacg   13020
gcacatgcgt gcctgtgccc tctccaacgc cccccccaga tgctccccgg cctgaacctt   13080
gtaacctgca gtgcttcaac ggtggcagct gtttcctcaa tgcacggagg cagcccaagt   13140
gccgctgcca accccgctac acgggtgaca agtgtgaact ggaccagtgc tgggagcact   13200
gtcgcaatgg gggcacctgt gctgcctccc cctctggcat gcccacgtgc cggtgcccca   13260
cgggcttcac gggcccccaaa tgcacccagc aggtgtgtgc gggctactgt gccaacaaca   13320
gcacctgcac tgtcaaccag ggcaaccagc cccagtgccg atgcctaccc ggcttcctgg   13380
gcgaccgctg ccagtaccgg cagtgctctg gctactgtga gaactttggc acatgccaga   13440
```

-continued

```
tggctgctga tggctcccga caatgccgct gcactgccta ctttgaggga tcgaggtgtg   13500
aggtgaacaa gtgcagccgc tgtctcgaag gggcctgtgt ggtcaacaag cagagtgggg   13560
atgtcacctg caactgcacg gatggccggg tggcccccag ctgtctgacc tgcgtcggcc   13620
actgcagcaa tggcggctcc tgtaccatga acagcaaaat gatgcctgag tgccagtgcc   13680
caccccacat gacagggccc cggtgtgagg agcacgtctt cagccagcag cagccaggac   13740
atatagcctc catcctaatc cctctgctgt tgctgctgct gctggttctg gtggccggag   13800
tggtattctg gtataagcgg cgagtccaag gggctaaggg cttccagcac caacggatga   13860
ccaacggggc catgaacgtg gagattggaa accccaccta caagatgtac gaaggcggag   13920
agcctgatga tgtgggaggc ctactggacg ctgactttgc cctggaccct gacaagccca   13980
ccaacttcac caaccccgtg tatgccacac tctacatggg gggccatggc agtcgccact   14040
ccctggccag cacggacgag aagcgagaac tcctgggccg gggccctgag gacgagatag   14100
gggacccctt ggcatagggc cctgccccgt cggactgccc ccagaaagcc tcctgccccc   14160
tgccagtgaa gtccttcagt gagcccctcc ccagccagcc cttccctggc cccgccggat   14220
gtataaatgt aaaaatgaag gaattacatt ttatatgtga gcgagcaagc cggcaagcga   14280
gcacagtatt atttctccat cccctccctg cctgctcctt ggcaccccca tgctgccttc   14340
agggagacag gcagggaggg cttggggctg cacctcctac cctcccacca gaacgcaccc   14400
cactgggaga gctggtggtg cagccttccc ctccctgtat aagacacttt gccaaggctc   14460
tcccctctcg ccccatccct gcttgcccgc tcccacagct tcctgagggc taattctggg   14520
aagggagagt tctttgctgc ccctgtctgg aagacgtggc tctgggtgag gtaggcggga   14580
aaggatggag tgttttagtt cttgggggag gccaccccaa accccagccc caactccagg   14640
ggcacctatg agatggccat gctcaacccc cctcccagac aggccctccc tgtctccagg   14700
gcccccaccg aggttcccag ggctggagac ttcctctggt aaacattcct ccagcctccc   14760
ctcccctggg gacgccaagg aggtgggcca cacccaggaa gggaaagcgg gcagcccgt   14820 tttggggacg tgaacgtttt aataattttt gctgaattcc tttacaacta aataacacag   14880
atattgttat aaataaaatt gtaaaaaaaa aaaaaaaaa aaa                        14923
```

<210> SEQ ID NO 2
<211> LENGTH: 10863
<212> TYPE: DNA
<213> ORGANISM: Homo sapiens

<400> SEQUENCE: 2

```
agtagcgttc gcccgaacat ggcgacacgg agcagcagga gggagtcgcg actcccgttc     60
ctattcaccc tggtcgcact gctgccgccc ggagctctct gcgaagtctg gacgcagagg    120
ctgcacggcg gcagcgcgcc cttgccccag gaccggggct tcctcgtggt gcagggcgac    180
ccgcgcgagc tgcggctgtg ggcgcgcggg gatgccaggg gggcgagccg cgcggacgag    240
aagccgctcc ggaggaaacg gagcgctgcc ctgcagcccg agcccatcaa ggtgtacgga    300
caggttagtc tgaatgattc ccacaatcag atggtggtgc actgggctgg agagaaaagc    360
aacgtgatcg tggccttggc ccgagatagc ctggcattgg cgaggcccaa gagcagtgat    420
gtgtacgtgt cttacgacta tggaaaatca ttcaagaaaa tttcagacaa gttaaacttt    480
ggcttgggaa ataggagtga agctgttatc gcccagttct accacagccc tgcggacaac    540
aagcggtaca tctttgcaga cgcttatgcc cagtacctct ggatcacgtt tgacttctgc    600
aacactcttc aaggcttttc catcccattt cgggcagctg atctcctcct acacagtaag    660
```

-continued

```
gcctccaacc ttctcttggg ctttgacagg tcccacccca acaagcagct gtggaagtca    720
gatgactttg gccagacctg gatcatgatt caggaacatg tcaagtcctt ttcttgggga    780
attgatccct atgacaaacc aaataccatc tacattgaac gacatgaacc ctctggctac    840
tccactgtct tccgaagtac agatttcttc cagtcccggg aaaaccagga agtgatcctt    900
gaggaagtga gagattttca gcttcgggac aagtacatgt ttgctacaaa ggtggtgcat    960
ctcttgggca gtgaacagca gtcttctgtc cagctctggg tctcctttgg ccggaagccc    1020
atgagagcag cccagtttgt cacaagacat cctattaatg aatattacat cgcagatgcc    1080
tccgaggacc aggtgtttgt gtgtgtcagc cacagtaaca accgcaccaa tttatacatc    1140
tcagaggcag aggggctgaa gttctccctg tccttggaga acgtgctcta ttacagccca    1200
ggaggggccg gcagtgacac cttggtgagg tattttgcaa atgaaccatt tgctgacttc    1260
caccgagtgg aaggattgca aggagtctac attgctactc tgattaatgg ttctatgaat    1320
gaggagaaca tgagatcggt catcaccttt gacaaagggg gaacctggga gtttcttcag    1380
gctccagcct tcacgggata tggagagaaa atcaattgtg agctttccca gggctgttcc    1440
cttcatctgg ctcagcgcct cagtcagctc ctcaacctcc agctccggag aatgcccatc    1500
ctgtccaagg agtcggctcc aggcctcatc atcgccactg gctcagtggg aaagaacttg    1560
gctagcaaga caaacgtgta catctctagc agtgctggag ccaggtggcg agaggcactt    1620
cctggacctc actactacac atggggagac cacggcggaa tcatcacggc cattgcccag    1680
ggcatggaaa ccaacgagct aaaatacagt accaatgaag gggagacctg gaaaacattc    1740
atcttctctg agaagccagt gtttgtgtat ggcctcctca cagaacctgg ggagaagagc    1800
actgtcttca ccatctttgg ctcgaacaaa gagaatgtcc acagctggct gatcctccag    1860
gtcaatgcca cggatgcctt gggagttccc tgcacagaga atgactacaa gctgtggtca    1920
ccatctgatg agcgggggaa tgagtgtttg ctgggacaca agactgtttt caaacggcgg    1980 acccccatg ccacatgctt caatggagag gactttgaca ggccggtggt cgtgtccaac    2040
tgctcctgca cccgggagga ctatgagtgt gacttcggtt tcaagatgag tgaagatttg    2100
tcattagagg tttgtgttcc agatccggaa ttttctggaa agtcatactc ccctcctgtg    2160
ccttgccctg tgggttctac ttacaggaga acgagaggct accggaagat ttctggggac    2220
acttgtagcg gaggagatgt tgaagcgcga ctggaaggag agctggtccc ctgtcccctg    2280
gcagaagaga acgagttcat tctgtatgct gtgaggaaat ccatctaccg ctatgacctg    2340
gcctcgggag ccaccgagca gttgcctctc accgggctac gggcagcagt ggccctggac    2400
tttgactatg agcacaactg tttgtattgg tccgacctgg ccttggacgt catccagcgc    2460
ctctgtttga atggaagcac agggcaagag gtgatcatca attctggcct ggagacagta    2520
gaagctttgg cttttgaacc cctcagccag ctgctttact gggtagatgc aggcttcaaa    2580
aagattgagg tagctaatcc agatggcgac ttccgactca caatcgtcaa ttcctctgtg    2640
cttgatcgtc ccagggctct ggtcctcgtg ccccaagagg gggtgatgtt ctggacagac    2700
tggggagacc tgaagcctgg gatttatcgg agcaatatgg atggttctgc tgcctatcac    2760
ctggtgtctg aggatgtgaa gtggcccaat ggcatctctg tggacgacca gtggatttac    2820
tggacggatg cctacctgga gtgcatagag cggatcacgt tcagtggcca gcagcgctct    2880
gtcattctgg acaacctccc gcaccccat gccattgctg tctttaagaa tgaaatctac    2940
tgggatgact ggtcacagct cagcatattc cgagcttcca aatacagtgg gtcccagatg    3000
```

-continued

```
gagattctgg caaaccagct cacggggctc atggacatga agattttcta caaggggaag    3060
aacactggaa gcaatgcctg tgtgcccagg ccatgcagcc tgctgtgcct gcccaaggcc    3120
aacaacagta gaagctgcag gtgtccagag gatgtgtcca gcagtgtgct tccatcaggg    3180
gacctgatgt gtgactgccc tcagggctat cagctcaaga acaataccctg tgtcaaacaa    3240 gagaacacct gtcttcgcaa ccagtatcgc tgcagcaacg ggaactgtat caacagcatt    3300
tggtggtgtg actttgacaa cgactgtgga gacatgagcg atgagagaaa ctgccctacc    3360
accatctgtg acctggacac ccagtttcgt tgccaggagt ctgggacttg tatcccactg    3420
tcctataaat gtgaccttga ggatgactgt ggagacaaca gtgatgaaag tcattgtgaa    3480
atgcaccagt gccggagtga cgagtacaac tgcagttccg gcatgtgcat ccgctcctcc    3540
tgggtatgtg acggggacaa cgactgcagg gactggtctg atgaagccaa ctgtaccgcc    3600
atctatcaca cctgtgaggc ctccaacttc cagtgccgaa acgggcactg catcccccag    3660
cggtgggcgt gtgacgggga tacggactgc caggatggtt ccgatgagga tccagtcaac    3720
tgtgagaaga agtgcaatgg attccgctgc ccaaacggca cttgcatccc atccagcaaa    3780
cattgtgatg gtctgcgtga ttgctctgat ggctccgatg aacagcactg cgagcccctc    3840
tgtacgcact tcatggactt tgtgtgtaag aaccgccagc agtgcctgtt ccactccatg    3900
gtctgtgacg gaatcatcca gtgccgcgac gggtccgatg aggatgcggc gtttgcagga    3960
tgctcccaag atcctgagtt ccacaaggta tgtgatgagt tcggtttcca gtgtcagaat    4020
ggagtgtgca tcagtttgat ttggaagtgc gacgggatgg atgattgcgg cgattattct    4080
gatgaagcca actgcgaaaa ccccacagaa gccccaaact gctccgcta cttccagttt    4140 cggtgtgaga atggccactg catccccaac agatggaaat gtgacaggga gaacgactgt    4200
ggggactggt ctgatgagaa ggattgtgga gattcacata ttcttccctt ctcgactcct    4260
gggccctcca cgtgtctgcc caattactac cgctgcagca gtgggacctg cgtgatggac    4320
acctgggtgt gcgacgggta ccgagattgt gcagatggct ctgacgagga agcctgcccc    4380
ttgcttgcaa acgtcactgc tgcctccact cccacccaac ttgggcgatg tgaccgattt    4440
gagttcgaat gccaccaacc gaagacgtgt attcccaact ggaagcgctg tgacggccac    4500
caagattgcc aggatggccg ggacgaggcc aattgcccca cacacagcac cttgacttgc    4560
atgagcaggg agtccagtg cgaggacggg gaggcctgca ttgtgctctc ggagcgctgc    4620
gacggcttcc tggactgctc ggacgagagc gatgaaaagg cctgcagtga tgagttgact    4680
gtgtacaaag tacagaatct tcagtggaca gctgacttct ctggggatgt gactttgacc    4740
tggatgaggc ccaaaaaaat gccctctgct tcttgtgtat ataatgtcta ctacagggtg    4800
gttggagaga gcatatggaa gactctggag acccacagca ataagacaaa cactgtatta    4860
aaagtcttga aaccagatac cacgtatcag gttaaagtac aggttcagtg tctcagcaag    4920
gcacacaaca ccaatgactt tgtgaccctg aggaccccag agggattgcc agatgcccct    4980
cgaaatctcc agctgtcact ccccagggaa gcagaaggtg tgattgtagg ccactgggct    5040
cctcccatcc acacccatgg cctcatccgt gagtacattg tagaatacag caggagtggt    5100
tccaagatgt gggcctccca gagggctgct agtaactta cagaaatcaa gaacttattg    5160
gtcaacactc tatacaccgt cagagtggct gcggtgacta gtcgtggaat aggaaactgg    5220
agcgattcta aatccattac caccataaaa ggaaaagtga tcccaccacc agatatccac    5280
attgacagca tggtgaaaa ttatctaagc ttcaccctga ccatggagag tgatatcaag    5340
gtgaatggct atgtggtgaa ccttttctgg gcatttgaca cccacaagca agagaggaga    5400
```

-continued

```
actttgaact tccgaggaag catattgtca cacaaagttg gcaatctgac agctcataca   5460
tcctatgaga tttctgcctg ggccaagact gacttggggg atagccctct ggcatttgag   5520
catgttatga ccagaggggt tcgcccacct gcacctagcc tcaaggccaa agccatcaac   5580
cagactgcag tggaatgtac ctggaccggc ccccggaatg tggtttatgg tattttctat   5640
gccacgtcct ttcttgacct ctatcgcaac ccgaagagct tgactacttc actccacaac   5700
aagacggtca ttgtcagtaa ggatgagcag tatttgtttc tggtccgtgt agtggtaccc   5760
taccaggggc catcctctga ctacgttgta gtgaagatga tcccggacag caggcttcca   5820
ccccgtcacc tgcatgtggt tcatacgggc aaaacctccg tggtcatcaa gtgggaatca   5880
ccgtatgact ctcctgacca ggacttgttg tatgcagttg cagtcaaaga tctcataaga   5940
aagactgaca ggagctacaa agtaaaatcc cgtaacagca ctgtggaata cacccttaac   6000
aagttggagc ctggcgggaa ataccacatc attgtccaac tggggaacat gagcaaagat   6060
tccagcataa aaattaccac agtttcatta tcagcacctg atgccttaaa aatcataaca   6120
gaaaatgatc atgttcttct gttttggaaa agcctggctt taaaggaaaa gcattttaat   6180
gaaagcaggg gctatgagat acacatgttt gatagtgcca tgaatatcac agcttacctt   6240
gggaatacta ctgacaattt ctttaaaatt tccaacctga agatgggtca taattacacg   6300
ttcaccgtcc aagcaagatg cctttttggc aaccagatct gtggggagcc tgccatcctg   6360
ctgtacgatg agctgggggtc tggtgcagat gcatctgcaa cgcaggctgc cagatctacg   6420
gatgttgctg ctgtggtggt gcccatctta ttcctgatac tgctgagcct gggggtgggg   6480
tttgccatcc tgtacacgaa gcaccggagg ctgcagagca gcttcaccgc cttcgccaac   6540
agccactaca gctccaggct ggggtccgca atcttctcct ctggggatga cctgggggaa   6600
gatgatgaag atgcccctat gataactgga ttttcagatg acgtccccat ggtgatagcc   6660
tgaaagagct ttcctcacta gaaaccaaat ggtgtaaata ttttatttga taaagatagt   6720
tgatggttta ttttaaaaga tgcactttga gttgcaatat gttattttta tatgggccaa   6780
aaacaaaaaa caaaaaaaaa aaaaggaaa gaaaggaatg aataaacttt gtagtaatca   6840
actgtgaact tcaaaccagg ttgatttag taacccaatt gctttgattt gacattaatg   6900
tagtcttaca gggctgtgct tgctgggcat gctttttacgt ctgtgagata atttcggttc   6960
agtaaattgg ccaatctttt tatttttcta agacacagaa atgtatttaa taaaaacctc   7020
gagagagtga tgggtggaac cccttctcct tgaaagtgtg tacagatatt ccattttgtt   7080
tggatatagt ttataggaaa gtgtgtggat gtattatggc ggaaggtttc tttatgttat   7140
tttgttaatt tattgggact ctgtgtaagg ccaggcttta gtggtcatta gacaccacat   7200
gtgttatgag cccttaccc ataggggtgg gggtgggaag agaagcatat tttttttgcca   7260 ttccggaagc aatccatttt tattcacttg tgtgtcatgt aatggtcttt ggcaggagag   7320
agcactgagt cattgctgga gttcagttca acagagctgc agcttgggaa gccctgtaag   7380
cccacagctt cctctcttat attaattgat ggaatttttac tgtatgtgcc tctgtacaag   7440
atgtagcttt gagagctaca aaatgataac actgctttat tacacactgg tttcattgtc   7500
attgcaaaaa cttaccctgg ttgtggggga gagttctaga tctgtgccat gatccataca   7560
ctggctaata gagtacataa ttttttccatt ttccatttt tgttttttact tactactgaa   7620 ggatctcaga tgtaaaatta tgtatttggt ttgagatggc cacttattgt ccttaaaaat   7680
ccatactgat atatgcagtc attttgaatt ggacagtgcc ttctcttttt ttttctcctc   7740
```

-continued

```
ttcttccatc tccctcaccc atgcccccac ccaatctaaa gagacagtgc tgtacattct      7800
catagagata gagaagatct aaaaagttga gactactcaa tccagttaac aacagcagga      7860
gcactagagt ttgttcattt attctctctg taaaacaagc tgtgcttttt ttcttctgcc      7920
tttaaaatgc cacccgtgta ttcaaaccat ggccacttga tacttatgta gaatccatcg      7980
tgggctgatg caagcccttt atttaggctt agtgttgtgg gcaccaatgt cgagcatcgt      8040
tgtgacttgt gctgtatgat tctcactgaa gaatttcctt tcagccaaga agcagtgagg      8100
tctgggaata ttccaaagtc atgtctctga atatgtgtcc ttgacgtgca agctttgtaa      8160
aaccccatcc ccgcttaggt gcgaggcatc accttctcac aagtgtttag tttctttttaa     8220 ccacaagtat cattcttggg tgataatata gtttcattct acttagggat tgtttagaaa      8280
acaaagaaag agccaattaa attttttagt ttttgaaatt tttatttata tgtatactta      8340
gatgagtatt ttaagctgtc gacctttagt ttgccatacg ggtaggactg tatttcatgt      8400
taacaactgg tggtaatgat aagccttctt ctagcgtatt ttctcttctt tcctgtcact      8460
ttcctaagtt ttttttttta aagactggaa ttttttttgg ctttatcttg tcttaccgta      8520
gagatttgtt caaaactcta agccctacca cctccccttt aataagctct ttaaatagtt      8580
gaatcattaa caacctggtg ggaggcaagt catttaattg aaccactagg aagtgtattt      8640
tcttttcttt ttctgccaac tttttggtgg catttgtaaa agctgatata aaaggctctg      8700
agatgttatt ttcagttatt ccataggcaa gcctttttac agagcatatg tctccagttg      8760
gcagcttgag atatttccga gcatccggtt ctagctacca gtgcctccca atgcttagtg      8820
cacagtactg tagactggcc atcacccctc tccttggaaa atgccactgt gctgtttgaa      8880
aaaaagcagc cttttagggc tagagtattt tatataaaca gaagagctaa gttcctgaag      8940
actaagctag atagctgcag ctatatgtaa attgtatatt tttatgaact tttgaagcac      9000
acactcctgt ttccctctgt gtagctttgt ggggatttca tgtatatatg ctgtctgaaa      9060
gaatccagag gttggagtgc caatagaaaa tgaaaacaaa tgccttgtac tacaggcagc      9120
ctctgaaggt gaccacataa ctgtcttcac tgtgaccaat cggagtccct gcttgcttgt      9180
gaagaagggg ctttttgtacc ttgttggaga tgccacctca gaagttcaca ctgtgcagga     9240
aaaaggtttt attctctcct ggcatacatt agaatgtcag atgcttgcat ccatgtggac      9300
cacgatgggc ctctaaaaat tggtgggcag ggggtttgct tatgagtttt ctctggaaac      9360
cgattttact cctggatgta ttgaatgccc cttgagcttt atgagatacg agtccacatg      9420
gataaaatgt tagagagtgg agttctacag aggattccag gaagaggcca tgtctgtgca      9480
gtcctagttc cagacaggtg agaagctcca ggaactactg gctaccttga caagctgggt      9540
aaatagttat cattctgggt aactggttga aactctgact tttggacaag taattcctgg      9600
ggttctgtct ttggtagcat caccagggat atttgggtgg gacagacaga agacacacag      9660
ctgcctgttc tctcctgccc atcatgtttg gcccactaga tgaagctgta ctcagcaatt      9720
tagggaatgt aacccttctc agaactggcc attttcaggg gaagcttggg agagcaatag      9780
tatggtgagc cccttagaga tgagcgccta ctccttcttg gcgaatgctg ccttcagatg      9840
cttaccaagt ggtcactgca tctagtaaga ttatatttcc agtacacttc cttagggcag      9900
aaacaccatc ctatcaggtt tggtcagtcc cttcttcatg aagggagtca tggggaattc      9960
ctgaaaattt tcttccttct gcagacagtt ggatgagtcc cttagagaag gcatccagag      10020
acataactaa actgaatatc atcccatatt gattttagga attgactcta aaactctgtg      10080
cagaatcttg tgttgggatt gtatcttgac attcctgttg tgttattttt cttaactgga      10140
```

-continued

```
gtgtgtgctg cctttcaggt acaatttttg tgtaataaaa gccagtgcat taagtttata    10200
tagactactt tctatgcaag actgagatat ggaatagata ggaagagata tgtactgctg    10260
ggtacatgga cagtaagtgt gttttcagat ggagtaccag caccgaaaat gggttgaggg    10320
aggatgggtt gtatgtatgt ttctgcccac taattttgag cagccatatt atgaattaaa    10380
tcgtcacagc caagtaataa cccaagaatg gtatgagttt catgtgtaat agctcaaatg    10440
gaataagcat gaatgctgga gtggaccatt atcctcaaat attctatgtc acttctcatt    10500
taaagactct tgttatgaac tattagaaac tttaggcaaa atcaaaagta tttgcggcaa    10560
aataaaggcc tattctactc ttatttaaag tgaaacactg tatacttgtt tctctccaaa    10620
gcgaaattaa gtatttataa tttcaattgc ctcgataagt ttccaagtca ctgaaatctg    10680
ctgaaggttt tactgtattg ttgcacaact ttaagataat ttttgtctca atgtcaactt    10740
ttttcactga ataaaaattt aactgggtca agaaaacacc tctttgaaaa tccactgtct    10800
ctgtgtgtct cgagctgttc tttagagcgc aataaagatg gctgacgcag tctccaaacc    10860
cca                                                                  10863
```

```
<210> SEQ ID NO 3
<211> LENGTH: 2214
<212> TYPE: PRT
<213> ORGANISM: Homo sapiens

<400> SEQUENCE: 3

Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
            115                 120                 125

Arg Pro Lys Ser Ser Asp Val Tyr Val Ser Tyr Asp Tyr Gly Lys Ser
    130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
                180                 185                 190

Phe Cys Asn Thr Leu Gln Gly Phe Ser Ile Pro Phe Arg Ala Ala Asp
            195                 200                 205

Leu Leu Leu His Ser Lys Ala Ser Asn Leu Leu Leu Gly Phe Asp Arg
    210                 215                 220

Ser His Pro Asn Lys Gln Leu Trp Lys Ser Asp Asp Phe Gly Gln Thr
225                 230                 235                 240
```

-continued

```
Trp Ile Met Ile Gln Glu His Val Lys Ser Phe Ser Trp Gly Ile Asp
            245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
            275                 280                 285

Asn Gln Glu Val Ile Leu Glu Glu Val Arg Asp Phe Gln Leu Arg Asp
            290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335

Ala Ala Gln Phe Val Thr Arg His Pro Ile Asn Glu Tyr Tyr Ile Ala
            340                 345                 350

Asp Ala Ser Glu Asp Gln Val Phe Val Cys Val Ser His Ser Asn Asn
            355                 360                 365

Arg Thr Asn Leu Tyr Ile Ser Glu Ala Glu Gly Leu Lys Phe Ser Leu
            370                 375                 380

Ser Leu Glu Asn Val Leu Tyr Tyr Ser Pro Gly Gly Ala Gly Ser Asp
385                 390                 395                 400

Thr Leu Val Arg Tyr Phe Ala Asn Glu Pro Phe Ala Asp Phe His Arg
                405                 410                 415

Val Glu Gly Leu Gln Gly Val Tyr Ile Ala Thr Leu Ile Asn Gly Ser
                420                 425                 430

Met Asn Glu Glu Asn Met Arg Ser Val Ile Thr Phe Asp Lys Gly Gly
            435                 440                 445

Thr Trp Glu Phe Leu Gln Ala Pro Ala Phe Thr Gly Tyr Gly Glu Lys
            450                 455                 460

Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                485                 490                 495

Lys Glu Ser Ala Pro Gly Leu Ile Ile Ala Thr Gly Ser Val Gly Lys
            500                 505                 510

Asn Leu Ala Ser Lys Thr Asn Val Tyr Ile Ser Ser Ser Ala Gly Ala
            515                 520                 525

Arg Trp Arg Glu Ala Leu Pro Gly Pro His Tyr Tyr Thr Trp Gly Asp
            530                 535                 540

His Gly Gly Ile Ile Thr Ala Ile Ala Gln Gly Met Glu Thr Asn Glu
545                 550                 555                 560

Leu Lys Tyr Ser Thr Asn Glu Gly Glu Thr Trp Lys Thr Phe Ile Phe
                565                 570                 575

Ser Glu Lys Pro Val Phe Val Tyr Gly Leu Leu Thr Glu Pro Gly Glu
            580                 585                 590

Lys Ser Thr Val Phe Thr Ile Phe Gly Ser Asn Lys Glu Asn Val His
            595                 600                 605

Ser Trp Leu Ile Leu Gln Val Asn Ala Thr Asp Ala Leu Gly Val Pro
            610                 615                 620

Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
                645                 650                 655
```

-continued

```
His Ala Thr Cys Phe Asn Gly Glu Asp Phe Asp Arg Pro Val Val Val
              660             665             670

Ser Asn Cys Ser Cys Thr Arg Glu Asp Tyr Glu Cys Asp Phe Gly Phe
              675             680             685

Lys Met Ser Glu Asp Leu Ser Leu Glu Val Cys Val Pro Asp Pro Glu
          690             695             700

Phe Ser Gly Lys Ser Tyr Ser Pro Pro Val Pro Cys Pro Val Gly Ser
705             710             715             720

Thr Tyr Arg Arg Thr Arg Gly Tyr Arg Lys Ile Ser Gly Asp Thr Cys
              725             730             735

Ser Gly Gly Asp Val Glu Ala Arg Leu Glu Gly Glu Leu Val Pro Cys
          740             745             750

Pro Leu Ala Glu Glu Asn Glu Phe Ile Leu Tyr Ala Val Arg Lys Ser
          755             760             765

Ile Tyr Arg Tyr Asp Leu Ala Ser Gly Ala Thr Glu Gln Leu Pro Leu
    770             775             780

Thr Gly Leu Arg Ala Ala Val Ala Leu Asp Phe Asp Tyr Glu His Asn
785             790             795             800

Cys Leu Tyr Trp Ser Asp Leu Ala Leu Asp Val Ile Gln Arg Leu Cys
              805             810             815

Leu Asn Gly Ser Thr Gly Gln Glu Val Ile Ile Asn Ser Gly Leu Glu
          820             825             830

Thr Val Glu Ala Leu Ala Phe Glu Pro Leu Ser Gln Leu Leu Tyr Trp
          835             840             845

Val Asp Ala Gly Phe Lys Lys Ile Glu Val Ala Asn Pro Asp Gly Asp
    850             855             860

Phe Arg Leu Thr Ile Val Asn Ser Ser Val Leu Asp Arg Pro Arg Ala
865             870             875             880

Leu Val Leu Val Pro Gln Glu Gly Val Met Phe Trp Thr Asp Trp Gly
              885             890             895

Asp Leu Lys Pro Gly Ile Tyr Arg Ser Asn Met Asp Gly Ser Ala Ala
          900             905             910

Tyr His Leu Val Ser Glu Asp Val Lys Trp Pro Asn Gly Ile Ser Val
          915             920             925

Asp Asp Gln Trp Ile Tyr Trp Thr Asp Ala Tyr Leu Glu Cys Ile Glu
    930             935             940

Arg Ile Thr Phe Ser Gly Gln Gln Arg Ser Val Ile Leu Asp Asn Leu
945             950             955             960

Pro His Pro Tyr Ala Ile Ala Val Phe Lys Asn Glu Ile Tyr Trp Asp
              965             970             975

Asp Trp Ser Gln Leu Ser Ile Phe Arg Ala Ser Lys Tyr Ser Gly Ser
          980             985             990

Gln Met Glu Ile Leu Ala Asn Gln  Leu Thr Gly Leu Met  Asp Met Lys
          995             1000            1005

Ile Phe  Tyr Lys Gly Lys Asn  Thr Gly Ser Asn Ala  Cys Val Pro
    1010            1015            1020

Arg Pro  Cys Ser Leu Leu Cys  Leu Pro Lys Ala Asn  Asn Ser Arg
    1025            1030            1035

Ser Cys  Arg Cys Pro Glu Asp  Val Ser Ser Ser Val  Leu Pro Ser
    1040            1045            1050

Gly Asp  Leu Met Cys Asp Cys  Pro Gln Gly Tyr Gln  Leu Lys Asn
    1055            1060            1065

Asn Thr  Cys Val Lys Gln Glu  Asn Thr Cys Leu Arg  Asn Gln Tyr
```

-continued

```
          1070              1075              1080

Arg Cys Ser Asn Gly Asn Cys Ile Asn Ser Ile Trp  Trp Cys Asp
    1085              1090              1095

Phe Asp Asn Asp Cys Gly Asp Met Ser Asp Glu Arg  Asn Cys Pro
    1100              1105              1110

Thr Thr Ile Cys Asp Leu Asp Thr Gln Phe Arg Cys  Gln Glu Ser
    1115              1120              1125

Gly Thr Cys Ile Pro Leu Ser Tyr Lys Cys Asp Leu  Glu Asp Asp
    1130              1135              1140

Cys Gly Asp Asn Ser Asp Glu Ser His Cys Glu Met  His Gln Cys
    1145              1150              1155

Arg Ser Asp Glu Tyr Asn Cys Ser Ser Gly Met Cys  Ile Arg Ser
    1160              1165              1170

Ser Trp Val Cys Asp Gly Asp Asn Asp Cys Arg Asp  Trp Ser Asp
    1175              1180              1185

Glu Ala Asn Cys Thr Ala Ile Tyr His Thr Cys Glu  Ala Ser Asn
    1190              1195              1200

Phe Gln Cys Arg Asn Gly His Cys Ile Pro Gln Arg  Trp Ala Cys
    1205              1210              1215

Asp Gly Asp Thr Asp Cys Gln Asp Gly Ser Asp Glu  Asp Pro Val
    1220              1225              1230

Asn Cys Glu Lys Lys Cys Asn Gly Phe Arg Cys Pro  Asn Gly Thr
    1235              1240              1245

Cys Ile Pro Ser Ser Lys His Cys Asp Gly Leu Arg  Asp Cys Ser
    1250              1255              1260

Asp Gly Ser Asp Glu Gln His Cys Glu Pro Leu Cys  Thr His Phe
    1265              1270              1275

Met Asp Phe Val Cys Lys Asn Arg Gln Gln Cys Leu  Phe His Ser
    1280              1285              1290

Met Val Cys Asp Gly Ile Ile Gln Cys Arg Asp Gly  Ser Asp Glu
    1295              1300              1305

Asp Ala Ala Phe Ala Gly Cys Ser Gln Asp Pro Glu  Phe His Lys
    1310              1315              1320

Val Cys Asp Glu Phe Gly Phe Gln Cys Gln Asn Gly  Val Cys Ile
    1325              1330              1335

Ser Leu Ile Trp Lys Cys Asp Gly Met Asp Asp Cys  Gly Asp Tyr
    1340              1345              1350

Ser Asp Glu Ala Asn Cys Glu Asn Pro Thr Glu Ala  Pro Asn Cys
    1355              1360              1365

Ser Arg Tyr Phe Gln Phe Arg Cys Glu Asn Gly His  Cys Ile Pro
    1370              1375              1380

Asn Arg Trp Lys Cys Asp Arg Glu Asn Asp Cys Gly  Asp Trp Ser
    1385              1390              1395

Asp Glu Lys Asp Cys Gly Asp Ser His Ile Leu Pro  Phe Ser Thr
    1400              1405              1410

Pro Gly Pro Ser Thr Cys Leu Pro Asn Tyr Tyr Arg  Cys Ser Ser
    1415              1420              1425

Gly Thr Cys Val Met Asp Thr Trp Val Cys Asp Gly  Tyr Arg Asp
    1430              1435              1440

Cys Ala Asp Gly Ser Asp Glu Glu Ala Cys Pro Leu  Leu Ala Asn
    1445              1450              1455

Val Thr Ala Ala Ser Thr Pro Thr Gln Leu Gly Arg  Cys Asp Arg
    1460              1465              1470
```

-continued

```
Phe Glu  Phe Glu Cys His Gln  Pro Lys Thr Cys Ile  Pro Asn Trp
    1475             1480              1485

Lys Arg  Cys Asp Gly His Gln  Asp Cys Gln Asp Gly  Arg Asp Glu
    1490             1495              1500

Ala Asn  Cys Pro Thr His Ser  Thr Leu Thr Cys Met  Ser Arg Glu
    1505             1510              1515

Phe Gln  Cys Glu Asp Gly Glu  Ala Cys Ile Val Leu  Ser Glu Arg
    1520             1525              1530

Cys Asp  Gly Phe Leu Asp Cys  Ser Asp Glu Ser Asp  Glu Lys Ala
    1535             1540              1545

Cys Ser  Asp Glu Leu Thr Val  Tyr Lys Val Gln Asn  Leu Gln Trp
    1550             1555              1560

Thr Ala  Asp Phe Ser Gly Asp  Val Thr Leu Thr Trp  Met Arg Pro
    1565             1570              1575

Lys Lys  Met Pro Ser Ala Ser  Cys Val Tyr Asn Val  Tyr Tyr Arg
    1580             1585              1590

Val Val  Gly Glu Ser Ile Trp  Lys Thr Leu Glu Thr  His Ser Asn
    1595             1600              1605

Lys Thr  Asn Thr Val Leu Lys  Val Leu Lys Pro Asp  Thr Thr Tyr
    1610             1615              1620

Gln Val  Lys Val Gln Val Gln  Cys Leu Ser Lys Ala  His Asn Thr
    1625             1630              1635

Asn Asp  Phe Val Thr Leu Arg  Thr Pro Glu Gly Leu  Pro Asp Ala
    1640             1645              1650

Pro Arg  Asn Leu Gln Leu Ser  Leu Pro Arg Glu Ala  Glu Gly Val
    1655             1660              1665

Ile Val  Gly His Trp Ala Pro  Pro Ile His Thr His  Gly Leu Ile
    1670             1675              1680

Arg Glu  Tyr Ile Val Glu Tyr  Ser Arg Ser Gly Ser  Lys Met Trp
    1685             1690              1695

Ala Ser  Gln Arg Ala Ala Ser  Asn Phe Thr Glu Ile  Lys Asn Leu
    1700             1705              1710

Leu Val  Asn Thr Leu Tyr Thr  Val Arg Val Ala Ala  Val Thr Ser
    1715             1720              1725

Arg Gly  Ile Gly Asn Trp Ser  Asp Ser Lys Ser Ile  Thr Thr Ile
    1730             1735              1740

Lys Gly  Lys Val Ile Pro Pro  Pro Asp Ile His Ile  Asp Ser Tyr
    1745             1750              1755

Gly Glu  Asn Tyr Leu Ser Phe  Thr Leu Thr Met Glu  Ser Asp Ile
    1760             1765              1770

Lys Val  Asn Gly Tyr Val Val  Asn Leu Phe Trp Ala  Phe Asp Thr
    1775             1780              1785

His Lys  Gln Glu Arg Arg Thr  Leu Asn Phe Arg Gly  Ser Ile Leu
    1790             1795              1800

Ser His  Lys Val Gly Asn Leu  Thr Ala His Thr Ser  Tyr Glu Ile
    1805             1810              1815

Ser Ala  Trp Ala Lys Thr Asp  Leu Gly Asp Ser Pro  Leu Ala Phe
    1820             1825              1830

Glu His  Val Met Thr Arg Gly  Val Arg Pro Pro Ala  Pro Ser Leu
    1835             1840              1845

Lys Ala  Lys Ala Ile Asn Gln  Thr Ala Val Glu Cys  Thr Trp Thr
    1850             1855              1860
```

-continued

| Gly | Pro | Arg | Asn | Val | Val | Tyr | Gly | Ile | Phe | Tyr | Ala | Thr | Ser | Phe |
| | 1865 | | | | | 1870 | | | | 1875 | | | | |

Leu Asp Leu Tyr Arg Asn Pro Lys Ser Leu Thr Thr Ser Leu His
    1880              1885              1890

Asn Lys Thr Val Ile Val Ser Lys Asp Glu Gln Tyr Leu Phe Leu
    1895              1900              1905

Val Arg Val Val Val Pro Tyr Gln Gly Pro Ser Ser Asp Tyr Val
    1910              1915              1920

Val Val Lys Met Ile Pro Asp Ser Arg Leu Pro Pro Arg His Leu
    1925              1930              1935

His Val Val His Thr Gly Lys Thr Ser Val Val Ile Lys Trp Glu
    1940              1945              1950

Ser Pro Tyr Asp Ser Pro Asp Gln Asp Leu Leu Tyr Ala Val Ala
    1955              1960              1965

Val Lys Asp Leu Ile Arg Lys Thr Asp Arg Ser Tyr Lys Val Lys
    1970              1975              1980

Ser Arg Asn Ser Thr Val Glu Tyr Thr Leu Asn Lys Leu Glu Pro
    1985              1990              1995

Gly Gly Lys Tyr His Ile Ile Val Gln Leu Gly Asn Met Ser Lys
    2000              2005              2010

Asp Ser Ser Ile Lys Ile Thr Thr Val Ser Leu Ser Ala Pro Asp
    2015              2020              2025

Ala Leu Lys Ile Ile Thr Glu Asn Asp His Val Leu Leu Phe Trp
    2030              2035              2040

Lys Ser Leu Ala Leu Lys Glu Lys His Phe Asn Glu Ser Arg Gly
    2045              2050              2055

Tyr Glu Ile His Met Phe Asp Ser Ala Met Asn Ile Thr Ala Tyr
    2060              2065              2070

Leu Gly Asn Thr Thr Asp Asn Phe Phe Lys Ile Ser Asn Leu Lys
    2075              2080              2085

Met Gly His Asn Tyr Thr Phe Thr Val Gln Ala Arg Cys Leu Phe
    2090              2095              2100

Gly Asn Gln Ile Cys Gly Glu Pro Ala Ile Leu Leu Tyr Asp Glu
    2105              2110              2115

Leu Gly Ser Gly Ala Asp Ala Ser Ala Thr Gln Ala Ala Arg Ser
    2120              2125              2130

Thr Asp Val Ala Ala Val Val Val Pro Ile Leu Phe Leu Ile Leu
    2135              2140              2145

Leu Ser Leu Gly Val Gly Phe Ala Ile Leu Tyr Thr Lys His Arg
    2150              2155              2160

Arg Leu Gln Ser Ser Phe Thr Ala Phe Ala Asn Ser His Tyr Ser
    2165              2170              2175

Ser Arg Leu Gly Ser Ala Ile Phe Ser Ser Gly Asp Asp Leu Gly
    2180              2185              2190

Glu Asp Asp Glu Asp Ala Pro Met Ile Thr Gly Phe Ser Asp Asp
    2195              2200              2205

Val Pro Met Val Ile Ala
    2210

<210> SEQ ID NO 4
<211> LENGTH: 4544
<212> TYPE: PRT
<213> ORGANISM: Homo sapiens

<400> SEQUENCE: 4

-continued

```
Met Leu Thr Pro Pro Leu Leu Leu Leu Leu Pro Leu Leu Ser Ala Leu
1               5                   10                  15

Val Ala Ala Ala Ile Asp Ala Pro Lys Thr Cys Ser Pro Lys Gln Phe
                20                  25                  30

Ala Cys Arg Asp Gln Ile Thr Cys Ile Ser Lys Gly Trp Arg Cys Asp
            35                  40                  45

Gly Glu Arg Asp Cys Pro Asp Gly Ser Asp Glu Ala Pro Glu Ile Cys
        50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
        130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
            195                 200                 205

Ile Leu Ala Thr Tyr Leu Ser Gly Ala Gln Val Ser Thr Ile Thr Pro
        210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
            275                 280                 285

Trp Leu Thr Gly Asn Phe Tyr Phe Val Asp Asp Ile Asp Asp Arg Ile
        290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
            325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365

Pro His Gly Ile Thr Leu Asp Leu Val Ser Arg Leu Val Tyr Trp Ala
        370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
            405                 410                 415
```

-continued

```
Thr Val Phe Glu Asn Tyr Leu Tyr Ala Thr Asn Ser Asp Asn Ala Asn
            420             425             430

Ala Gln Gln Lys Thr Ser Val Ile Arg Val Asn Arg Phe Asn Ser Thr
            435             440             445

Glu Tyr Gln Val Val Thr Arg Val Asp Lys Gly Gly Ala Leu His Ile
            450             455             460

Tyr His Gln Arg Arg Gln Pro Arg Val Arg Ser His Ala Cys Glu Asn
465             470             475             480

Asp Gln Tyr Gly Lys Pro Gly Gly Cys Ser Asp Ile Cys Leu Leu Ala
                485             490             495

Asn Ser His Lys Ala Arg Thr Cys Arg Cys Arg Ser Gly Phe Ser Leu
            500             505             510

Gly Ser Asp Gly Lys Ser Cys Lys Lys Pro Glu His Glu Leu Phe Leu
            515             520             525

Val Tyr Gly Lys Gly Arg Pro Gly Ile Ile Arg Gly Met Asp Met Gly
            530             535             540

Ala Lys Val Pro Asp Glu His Met Ile Pro Ile Glu Asn Leu Met Asn
545             550             555             560

Pro Arg Ala Leu Asp Phe His Ala Glu Thr Gly Phe Ile Tyr Phe Ala
                565             570             575

Asp Thr Thr Ser Tyr Leu Ile Gly Arg Gln Lys Ile Asp Gly Thr Glu
            580             585             590

Arg Glu Thr Ile Leu Lys Asp Gly Ile His Asn Val Glu Gly Val Ala
            595             600             605

Val Asp Trp Met Gly Asp Asn Leu Tyr Trp Thr Asp Asp Gly Pro Lys
            610             615             620

Lys Thr Ile Ser Val Ala Arg Leu Glu Lys Ala Ala Gln Thr Arg Lys
625             630             635             640

Thr Leu Ile Glu Gly Lys Met Thr His Pro Arg Ala Ile Val Val Asp
                645             650             655

Pro Leu Asn Gly Trp Met Tyr Trp Thr Asp Trp Glu Glu Asp Pro Lys
            660             665             670

Asp Ser Arg Arg Gly Arg Leu Glu Arg Ala Trp Met Asp Gly Ser His
            675             680             685

Arg Asp Ile Phe Val Thr Ser Lys Thr Val Leu Trp Pro Asn Gly Leu
            690             695             700

Ser Leu Asp Ile Pro Ala Gly Arg Leu Tyr Trp Val Asp Ala Phe Tyr
705             710             715             720

Asp Arg Ile Glu Thr Ile Leu Leu Asn Gly Thr Asp Arg Lys Ile Val
                725             730             735

Tyr Glu Gly Pro Glu Leu Asn His Ala Phe Gly Leu Cys His His Gly
            740             745             750

Asn Tyr Leu Phe Trp Thr Glu Tyr Arg Ser Gly Ser Val Tyr Arg Leu
            755             760             765

Glu Arg Gly Val Gly Gly Ala Pro Pro Thr Val Thr Leu Leu Arg Ser
            770             775             780

Glu Arg Pro Pro Ile Phe Glu Ile Arg Met Tyr Asp Ala Gln Gln Gln
785             790             795             800

Gln Val Gly Thr Asn Lys Cys Arg Val Asn Asn Gly Gly Cys Ser Ser
                805             810             815

Leu Cys Leu Ala Thr Pro Gly Ser Arg Gln Cys Ala Cys Ala Glu Asp
            820             825             830

Gln Val Leu Asp Ala Asp Gly Val Thr Cys Leu Ala Asn Pro Ser Tyr
```

-continued

```
                835              840              845
Val Pro Pro Gln Cys Gln Pro Gly Glu Phe Ala Cys Ala Asn Ser
    850              855              860

Arg Cys Ile Gln Glu Arg Trp Lys Cys Asp Gly Asp Asn Asp Cys Leu
865              870              875              880

Asp Asn Ser Asp Glu Ala Pro Ala Leu Cys His Gln His Thr Cys Pro
                885              890              895

Ser Asp Arg Phe Lys Cys Glu Asn Asn Arg Cys Ile Pro Asn Arg Trp
                900              905              910

Leu Cys Asp Gly Asp Asn Asp Cys Gly Asn Ser Glu Asp Glu Ser Asn
            915              920              925

Ala Thr Cys Ser Ala Arg Thr Cys Pro Pro Asn Gln Phe Ser Cys Ala
    930              935              940

Ser Gly Arg Cys Ile Pro Ile Ser Trp Thr Cys Asp Leu Asp Asp Asp
945              950              955              960

Cys Gly Asp Arg Ser Asp Glu Ser Ala Ser Cys Ala Tyr Pro Thr Cys
            965              970              975

Phe Pro Leu Thr Gln Phe Thr Cys Asn Asn Gly Arg Cys Ile Asn Ile
            980              985              990

Asn Trp Arg Cys Asp Asn Asp Asn  Asp Cys Gly Asp Asn  Ser Asp Glu
        995              1000              1005

Ala Gly Cys Ser His Ser Cys  Ser Ser Thr Gln Phe  Lys Cys Asn
    1010              1015              1020

Ser Gly Arg Cys Ile Pro Glu  His Trp Thr Cys Asp  Gly Asp Asn
    1025              1030              1035

Asp Cys Gly Asp Tyr Ser Asp  Glu Thr His Ala Asn  Cys Thr Asn
    1040              1045              1050

Gln Ala Thr Arg Pro Pro Gly  Gly Cys His Thr Asp  Glu Phe Gln
    1055              1060              1065

Cys Arg Leu Asp Gly Leu Cys  Ile Pro Leu Arg Trp  Arg Cys Asp
    1070              1075              1080

Gly Asp Thr Asp Cys Met Asp  Ser Ser Asp Glu Lys  Ser Cys Glu
    1085              1090              1095

Gly Val Thr His Val Cys Asp  Pro Ser Val Lys Phe  Gly Cys Lys
    1100              1105              1110

Asp Ser Ala Arg Cys Ile Ser  Lys Ala Trp Val Cys  Asp Gly Asp
    1115              1120              1125

Asn Asp Cys Glu Asp Asn Ser  Asp Glu Glu Asn Cys  Glu Ser Leu
    1130              1135              1140

Ala Cys Arg Pro Pro Ser His  Pro Cys Ala Asn Asn  Thr Ser Val
    1145              1150              1155

Cys Leu Pro Pro Asp Lys Leu  Cys Asp Gly Asn Asp  Asp Cys Gly
    1160              1165              1170

Asp Gly Ser Asp Glu Gly Glu  Leu Cys Asp Gln Cys  Ser Leu Asn
    1175              1180              1185

Asn Gly Gly Cys Ser His Asn  Cys Ser Val Ala Pro  Gly Glu Gly
    1190              1195              1200

Ile Val Cys Ser Cys Pro Leu  Gly Met Glu Leu Gly  Pro Asp Asn
    1205              1210              1215

His Thr Cys Gln Ile Gln Ser  Tyr Cys Ala Lys His  Leu Lys Cys
    1220              1225              1230

Ser Gln Lys Cys Asp Gln Asn  Lys Phe Ser Val Lys  Cys Ser Cys
    1235              1240              1245
```

-continued

```
Tyr Glu  Gly Trp Val Leu Glu  Pro Asp Gly Glu Ser  Cys Arg Ser
    1250                 1255              1260

Leu Asp  Pro Phe Lys Pro Phe  Ile Ile Phe Ser Asn  Arg His Glu
    1265                 1270              1275

Ile Arg  Arg Ile Asp Leu His  Lys Gly Asp Tyr Ser  Val Leu Val
    1280                 1285              1290

Pro Gly  Leu Arg Asn Thr Ile  Ala Leu Asp Phe His  Leu Ser Gln
    1295                 1300              1305

Ser Ala  Leu Tyr Trp Thr Asp  Val Val Glu Asp Lys  Ile Tyr Arg
    1310                 1315              1320

Gly Lys  Leu Leu Asp Asn Gly  Ala Leu Thr Ser Phe  Glu Val Val
    1325                 1330              1335

Ile Gln  Tyr Gly Leu Ala Thr  Pro Glu Gly Leu Ala  Val Asp Trp
    1340                 1345              1350

Ile Ala  Gly Asn Ile Tyr Trp  Val Glu Ser Asn Leu  Asp Gln Ile
    1355                 1360              1365

Glu Val  Ala Lys Leu Asp Gly  Thr Leu Arg Thr Thr  Leu Leu Ala
    1370                 1375              1380

Gly Asp  Ile Glu His Pro Arg  Ala Ile Ala Leu Asp  Pro Arg Asp
    1385                 1390              1395

Gly Ile  Leu Phe Trp Thr Asp  Trp Asp Ala Ser Leu  Pro Arg Ile
    1400                 1405              1410

Glu Ala  Ala Ser Met Ser Gly  Ala Gly Arg Arg Thr  Val His Arg
    1415                 1420              1425

Glu Thr  Gly Ser Gly Gly Trp  Pro Asn Gly Leu Thr  Val Asp Tyr
    1430                 1435              1440

Leu Glu  Lys Arg Ile Leu Trp  Ile Asp Ala Arg Ser  Asp Ala Ile
    1445                 1450              1455

Tyr Ser  Ala Arg Tyr Asp Gly  Ser Gly His Met Glu  Val Leu Arg
    1460                 1465              1470

Gly His  Glu Phe Leu Ser His  Pro Phe Ala Val Thr  Leu Tyr Gly
    1475                 1480              1485

Gly Glu  Val Tyr Trp Thr Asp  Trp Arg Thr Asn Thr  Leu Ala Lys
    1490                 1495              1500

Ala Asn  Lys Trp Thr Gly His  Asn Val Thr Val Val  Gln Arg Thr
    1505                 1510              1515

Asn Thr  Gln Pro Phe Asp Leu  Gln Val Tyr His Pro  Ser Arg Gln
    1520                 1525              1530

Pro Met  Ala Pro Asn Pro Cys  Glu Ala Asn Gly Gly  Gln Gly Pro
    1535                 1540              1545

Cys Ser  His Leu Cys Leu Ile  Asn Tyr Asn Arg Thr  Val Ser Cys
    1550                 1555              1560

Ala Cys  Pro His Leu Met Lys  Leu His Lys Asp Asn  Thr Thr Cys
    1565                 1570              1575

Tyr Glu  Phe Lys Lys Phe Leu  Leu Tyr Ala Arg Gln  Met Glu Ile
    1580                 1585              1590

Arg Gly  Val Asp Leu Asp Ala  Pro Tyr Tyr Asn Tyr  Ile Ile Ser
    1595                 1600              1605

Phe Thr  Val Pro Asp Ile Asp  Asn Val Thr Val Leu  Asp Tyr Asp
    1610                 1615              1620

Ala Arg  Glu Gln Arg Val Tyr  Trp Ser Asp Val Arg  Thr Gln Ala
    1625                 1630              1635
```

-continued

```
Ile Lys  Arg Ala Phe Ile Asn  Gly Thr Gly Val Glu  Thr Val Val
    1640             1645             1650

Ser Ala  Asp Leu Pro Asn Ala  His Gly Leu Ala Val  Asp Trp Val
    1655             1660             1665

Ser Arg  Asn Leu Phe Trp Thr  Ser Tyr Asp Thr Asn  Lys Lys Gln
    1670             1675             1680

Ile Asn  Val Ala Arg Leu Asp  Gly Ser Phe Lys Asn  Ala Val Val
    1685             1690             1695

Gln Gly  Leu Glu Gln Pro His  Gly Leu Val Val His  Pro Leu Arg
    1700             1705             1710

Gly Lys  Leu Tyr Trp Thr Asp  Gly Asp Asn Ile Ser  Met Ala Asn
    1715             1720             1725

Met Asp  Gly Ser Asn Arg Thr  Leu Leu Phe Ser Gly  Gln Lys Gly
    1730             1735             1740

Pro Val  Gly Leu Ala Ile Asp  Phe Pro Glu Ser Lys  Leu Tyr Trp
    1745             1750             1755

Ile Ser  Ser Gly Asn His Thr  Ile Asn Arg Cys Asn  Leu Asp Gly
    1760             1765             1770

Ser Gly  Leu Glu Val Ile Asp  Ala Met Arg Ser Gln  Leu Gly Lys
    1775             1780             1785

Ala Thr  Ala Leu Ala Ile Met  Gly Asp Lys Leu Trp  Trp Ala Asp
    1790             1795             1800

Gln Val  Ser Glu Lys Met Gly  Thr Cys Ser Lys Ala  Asp Gly Ser
    1805             1810             1815

Gly Ser  Val Val Leu Arg Asn  Ser Thr Thr Leu Val  Met His Met
    1820             1825             1830

Lys Val  Tyr Asp Glu Ser Ile  Gln Leu Asp His Lys  Gly Thr Asn
    1835             1840             1845

Pro Cys  Ser Val Asn Asn Gly  Asp Cys Ser Gln Leu  Cys Leu Pro
    1850             1855             1860

Thr Ser  Glu Thr Thr Arg Ser  Cys Met Cys Thr Ala  Gly Tyr Ser
    1865             1870             1875

Leu Arg  Ser Gly Gln Gln Ala  Cys Glu Gly Val Gly  Ser Phe Leu
    1880             1885             1890

Leu Tyr  Ser Val His Glu Gly  Ile Arg Gly Ile Pro  Leu Asp Pro
    1895             1900             1905

Asn Asp  Lys Ser Asp Ala Leu  Val Pro Val Ser Gly  Thr Ser Leu
    1910             1915             1920

Ala Val  Gly Ile Asp Phe His  Ala Glu Asn Asp Thr  Ile Tyr Trp
    1925             1930             1935

Val Asp  Met Gly Leu Ser Thr  Ile Ser Arg Ala Lys  Arg Asp Gln
    1940             1945             1950

Thr Trp  Arg Glu Asp Val Val  Thr Asn Gly Ile Gly  Arg Val Glu
    1955             1960             1965

Gly Ile  Ala Val Asp Trp Ile  Ala Gly Asn Ile Tyr  Trp Thr Asp
    1970             1975             1980

Gln Gly  Phe Asp Val Ile Glu  Val Ala Arg Leu Asn  Gly Ser Phe
    1985             1990             1995

Arg Tyr  Val Val Ile Ser Gln  Gly Leu Asp Lys Pro  Arg Ala Ile
    2000             2005             2010

Thr Val  His Pro Glu Lys Gly  Tyr Leu Phe Trp Thr  Glu Trp Gly
    2015             2020             2025

Gln Tyr  Pro Arg Ile Glu Arg  Ser Arg Leu Asp Gly  Thr Glu Arg
```

```
            2030                2035                2040

Val Val  Leu Val Asn Val Ser  Ile Ser Trp Pro Asn  Gly Ile Ser
    2045                2050                2055

Val Asp  Tyr Gln Asp Gly Lys  Leu Tyr Trp Cys Asp  Ala Arg Thr
    2060                2065                2070

Asp Lys  Ile Glu Arg Ile Asp  Leu Glu Thr Gly Glu  Asn Arg Glu
    2075                2080                2085

Val Val  Leu Ser Ser Asn Asn  Met Asp Met Phe Ser  Val Ser Val
    2090                2095                2100

Phe Glu  Asp Phe Ile Tyr Trp  Ser Asp Arg Thr His  Ala Asn Gly
    2105                2110                2115

Ser Ile  Lys Arg Gly Ser Lys  Asp Asn Ala Thr Asp  Ser Val Pro
    2120                2125                2130

Leu Arg  Thr Gly Ile Gly Val  Gln Leu Lys Asp Ile  Lys Val Phe
    2135                2140                2145

Asn Arg  Asp Arg Gln Lys Gly  Thr Asn Val Cys Ala  Val Ala Asn
    2150                2155                2160

Gly Gly  Cys Gln Gln Leu Cys  Leu Tyr Arg Gly Arg  Gly Gln Arg
    2165                2170                2175

Ala Cys  Ala Cys Ala His Gly  Met Leu Ala Glu Asp  Gly Ala Ser
    2180                2185                2190

Cys Arg  Glu Tyr Ala Gly Tyr  Leu Leu Tyr Ser Glu  Arg Thr Ile
    2195                2200                2205

Leu Lys  Ser Ile His Leu Ser  Asp Glu Arg Asn Leu  Asn Ala Pro
    2210                2215                2220

Val Gln  Pro Phe Glu Asp Pro  Glu His Met Lys Asn  Val Ile Ala
    2225                2230                2235

Leu Ala  Phe Asp Tyr Arg Ala  Gly Thr Ser Pro Gly  Thr Pro Asn
    2240                2245                2250

Arg Ile  Phe Phe Ser Asp Ile  His Phe Gly Asn Ile  Gln Gln Ile
    2255                2260                2265

Asn Asp  Asp Gly Ser Arg Arg  Ile Thr Ile Val Glu  Asn Val Gly
    2270                2275                2280

Ser Val  Glu Gly Leu Ala Tyr  His Arg Gly Trp Asp  Thr Leu Tyr
    2285                2290                2295

Trp Thr  Ser Tyr Thr Thr Ser  Thr Ile Thr Arg His  Thr Val Asp
    2300                2305                2310

Gln Thr  Arg Pro Gly Ala Phe  Glu Arg Glu Thr Val  Ile Thr Met
    2315                2320                2325

Ser Gly  Asp Asp His Pro Arg  Ala Phe Val Leu Asp  Glu Cys Gln
    2330                2335                2340

Asn Leu  Met Phe Trp Thr Asn  Trp Asn Glu Gln His  Pro Ser Ile
    2345                2350                2355

Met Arg  Ala Ala Leu Ser Gly  Ala Asn Val Leu Thr  Leu Ile Glu
    2360                2365                2370

Lys Asp  Ile Arg Thr Pro Asn  Gly Leu Ala Ile Asp  His Arg Ala
    2375                2380                2385

Glu Lys  Leu Tyr Phe Ser Asp  Ala Thr Leu Asp Lys  Ile Glu Arg
    2390                2395                2400

Cys Glu  Tyr Asp Gly Ser His  Arg Tyr Val Ile Leu  Lys Ser Glu
    2405                2410                2415

Pro Val  His Pro Phe Gly Leu  Ala Val Tyr Gly Glu  His Ile Phe
    2420                2425                2430
```

-continued

```
Trp Thr  Asp Trp Val Arg Arg  Ala Val Gln Arg Ala  Asn Lys His
    2435                 2440                 2445

Val Gly  Ser Asn Met Lys Leu  Leu Arg Val Asp Ile  Pro Gln Gln
    2450                 2455                 2460

Pro Met  Gly Ile Ile Ala Val  Ala Asn Asp Thr Asn  Ser Cys Glu
    2465                 2470                 2475

Leu Ser  Pro Cys Arg Ile Asn  Asn Gly Gly Cys Gln  Asp Leu Cys
    2480                 2485                 2490

Leu Leu  Thr His Gln Gly His  Val Asn Cys Ser Cys  Arg Gly Gly
    2495                 2500                 2505

Arg Ile  Leu Gln Asp Asp Leu  Thr Cys Arg Ala Val  Asn Ser Ser
    2510                 2515                 2520

Cys Arg  Ala Gln Asp Glu Phe  Glu Cys Ala Asn Gly  Glu Cys Ile
    2525                 2530                 2535

Asn Phe  Ser Leu Thr Cys Asp  Gly Val Pro His Cys  Lys Asp Lys
    2540                 2545                 2550

Ser Asp  Glu Lys Pro Ser Tyr  Cys Asn Ser Arg Arg  Cys Lys Lys
    2555                 2560                 2565

Thr Phe  Arg Gln Cys Ser Asn  Gly Arg Cys Val Ser  Asn Met Leu
    2570                 2575                 2580

Trp Cys  Asn Gly Ala Asp Asp  Cys Gly Asp Gly Ser  Asp Glu Ile
    2585                 2590                 2595

Pro Cys  Asn Lys Thr Ala Cys  Gly Val Gly Glu Phe  Arg Cys Arg
    2600                 2605                 2610

Asp Gly  Thr Cys Ile Gly Asn  Ser Ser Arg Cys Asn  Gln Phe Val
    2615                 2620                 2625

Asp Cys  Glu Asp Ala Ser Asp  Glu Met Asn Cys Ser  Ala Thr Asp
    2630                 2635                 2640

Cys Ser  Ser Tyr Phe Arg Leu  Gly Val Lys Gly Val  Leu Phe Gln
    2645                 2650                 2655

Pro Cys  Glu Arg Thr Ser Leu  Cys Tyr Ala Pro Ser  Trp Val Cys
    2660                 2665                 2670

Asp Gly  Ala Asn Asp Cys Gly  Asp Tyr Ser Asp Glu  Arg Asp Cys
    2675                 2680                 2685

Pro Gly  Val Lys Arg Pro Arg  Cys Pro Leu Asn Tyr  Phe Ala Cys
    2690                 2695                 2700

Pro Ser  Gly Arg Cys Ile Pro  Met Ser Trp Thr Cys  Asp Lys Glu
    2705                 2710                 2715

Asp Asp  Cys Glu His Gly Glu  Asp Glu Thr His Cys  Asn Lys Phe
    2720                 2725                 2730

Cys Ser  Glu Ala Gln Phe Glu  Cys Gln Asn His Arg  Cys Ile Ser
    2735                 2740                 2745

Lys Gln  Trp Leu Cys Asp Gly  Ser Asp Asp Cys Gly  Asp Gly Ser
    2750                 2755                 2760

Asp Glu  Ala Ala His Cys Glu  Gly Lys Thr Cys Gly  Pro Ser Ser
    2765                 2770                 2775

Phe Ser  Cys Pro Gly Thr His  Val Cys Val Pro Glu  Arg Trp Leu
    2780                 2785                 2790

Cys Asp  Gly Asp Lys Asp Cys  Ala Asp Gly Ala Asp  Glu Ser Ile
    2795                 2800                 2805

Ala Ala  Gly Cys Leu Tyr Asn  Ser Thr Cys Asp Asp  Arg Glu Phe
    2810                 2815                 2820
```

-continued

```
Met Cys Gln Asn Arg Gln Cys  Ile Pro Lys His Phe  Val Cys Asp
2825                2830                 2835

His Asp Arg Asp Cys Ala Asp  Gly Ser Asp Glu Ser  Pro Glu Cys
2840                2845                 2850

Glu Tyr Pro Thr Cys Gly Pro  Ser Glu Phe Arg Cys  Ala Asn Gly
2855                2860                 2865

Arg Cys Leu Ser Ser Arg Gln  Trp Glu Cys Asp Gly  Glu Asn Asp
2870                2875                 2880

Cys His Asp Gln Ser Asp Glu  Ala Pro Lys Asn Pro  His Cys Thr
2885                2890                 2895

Ser Gln Glu His Lys Cys Asn  Ala Ser Ser Gln Phe  Leu Cys Ser
2900                2905                 2910

Ser Gly Arg Cys Val Ala Glu  Ala Leu Leu Cys Asn  Gly Gln Asp
2915                2920                 2925

Asp Cys Gly Asp Ser Ser Asp  Glu Arg Gly Cys His  Ile Asn Glu
2930                2935                 2940

Cys Leu Ser Arg Lys Leu Ser  Gly Cys Ser Gln Asp  Cys Glu Asp
2945                2950                 2955

Leu Lys Ile Gly Phe Lys Cys  Arg Cys Arg Pro Gly  Phe Arg Leu
2960                2965                 2970

Lys Asp Asp Gly Arg Thr Cys  Ala Asp Val Asp Glu  Cys Ser Thr
2975                2980                 2985

Thr Phe Pro Cys Ser Gln Arg  Cys Ile Asn Thr His  Gly Ser Tyr
2990                2995                 3000

Lys Cys Leu Cys Val Glu Gly  Tyr Ala Pro Arg Gly  Gly Asp Pro
3005                3010                 3015

His Ser Cys Lys Ala Val Thr  Asp Glu Glu Pro Phe  Leu Ile Phe
3020                3025                 3030

Ala Asn Arg Tyr Tyr Leu Arg  Lys Leu Asn Leu Asp  Gly Ser Asn
3035                3040                 3045

Tyr Thr Leu Leu Lys Gln Gly  Leu Asn Asn Ala Val  Ala Leu Asp
3050                3055                 3060

Phe Asp Tyr Arg Glu Gln Met  Ile Tyr Trp Thr Asp  Val Thr Thr
3065                3070                 3075

Gln Gly Ser Met Ile Arg Arg  Met His Leu Asn Gly  Ser Asn Val
3080                3085                 3090

Gln Val Leu His Arg Thr Gly  Leu Ser Asn Pro Asp  Gly Leu Ala
3095                3100                 3105

Val Asp Trp Val Gly Gly Asn  Leu Tyr Trp Cys Asp  Lys Gly Arg
3110                3115                 3120

Asp Thr Ile Glu Val Ser Lys  Leu Asn Gly Ala Tyr  Arg Thr Val
3125                3130                 3135

Leu Val Ser Ser Gly Leu Arg  Glu Pro Arg Ala Leu  Val Val Asp
3140                3145                 3150

Val Gln Asn Gly Tyr Leu Tyr  Trp Thr Asp Trp Gly  Asp His Ser
3155                3160                 3165

Leu Ile Gly Arg Ile Gly Met  Asp Gly Ser Ser Arg  Ser Val Ile
3170                3175                 3180

Val Asp Thr Lys Ile Thr Trp  Pro Asn Gly Leu Thr  Leu Asp Tyr
3185                3190                 3195

Val Thr Glu Arg Ile Tyr Trp  Ala Asp Ala Arg Glu  Asp Tyr Ile
3200                3205                 3210

Glu Phe Ala Ser Leu Asp Gly  Ser Asn Arg His Val  Val Leu Ser
```

-continued

```
            3215                     3220                     3225

Gln Asp Ile Pro His Ile Phe Ala Leu Thr Leu Phe Glu Asp Tyr
        3230                    3235                    3240

Val Tyr Trp Thr Asp Trp Glu Thr Lys Ser Ile Asn Arg Ala His
        3245                    3250                    3255

Lys Thr Thr Gly Thr Asn Lys Thr Leu Leu Ile Ser Thr Leu His
        3260                    3265                    3270

Arg Pro Met Asp Leu His Val Phe His Ala Leu Arg Gln Pro Asp
        3275                    3280                    3285

Val Pro Asn His Pro Cys Lys Val Asn Asn Gly Gly Cys Ser Asn
        3290                    3295                    3300

Leu Cys Leu Leu Ser Pro Gly Gly Gly His Lys Cys Ala Cys Pro
        3305                    3310                    3315

Thr Asn Phe Tyr Leu Gly Ser Asp Gly Arg Thr Cys Val Ser Asn
        3320                    3325                    3330

Cys Thr Ala Ser Gln Phe Val Cys Lys Asn Asp Lys Cys Ile Pro
        3335                    3340                    3345

Phe Trp Trp Lys Cys Asp Thr Glu Asp Asp Cys Gly Asp His Ser
        3350                    3355                    3360

Asp Glu Pro Pro Asp Cys Pro Glu Phe Lys Cys Arg Pro Gly Gln
        3365                    3370                    3375

Phe Gln Cys Ser Thr Gly Ile Cys Thr Asn Pro Ala Phe Ile Cys
        3380                    3385                    3390

Asp Gly Asp Asn Asp Cys Gln Asp Asn Ser Asp Glu Ala Asn Cys
        3395                    3400                    3405

Asp Ile His Val Cys Leu Pro Ser Gln Phe Lys Cys Thr Asn Thr
        3410                    3415                    3420

Asn Arg Cys Ile Pro Gly Ile Phe Arg Cys Asn Gly Gln Asp Asn
        3425                    3430                    3435

Cys Gly Asp Gly Glu Asp Glu Arg Asp Cys Pro Glu Val Thr Cys
        3440                    3445                    3450

Ala Pro Asn Gln Phe Gln Cys Ser Ile Thr Lys Arg Cys Ile Pro
        3455                    3460                    3465

Arg Val Trp Val Cys Asp Arg Asp Asn Asp Cys Val Asp Gly Ser
        3470                    3475                    3480

Asp Glu Pro Ala Asn Cys Thr Gln Met Thr Cys Gly Val Asp Glu
        3485                    3490                    3495

Phe Arg Cys Lys Asp Ser Gly Arg Cys Ile Pro Ala Arg Trp Lys
        3500                    3505                    3510

Cys Asp Gly Glu Asp Asp Cys Gly Asp Gly Ser Asp Glu Pro Lys
        3515                    3520                    3525

Glu Glu Cys Asp Glu Arg Thr Cys Glu Pro Tyr Gln Phe Arg Cys
        3530                    3535                    3540

Lys Asn Asn Arg Cys Val Pro Gly Arg Trp Gln Cys Asp Tyr Asp
        3545                    3550                    3555

Asn Asp Cys Gly Asp Asn Ser Asp Glu Glu Ser Cys Thr Pro Arg
        3560                    3565                    3570

Pro Cys Ser Glu Ser Glu Phe Ser Cys Ala Asn Gly Arg Cys Ile
        3575                    3580                    3585

Ala Gly Arg Trp Lys Cys Asp Gly Asp His Asp Cys Ala Asp Gly
        3590                    3595                    3600

Ser Asp Glu Lys Asp Cys Thr Pro Arg Cys Asp Met Asp Gln Phe
        3605                    3610                    3615
```

-continued

```
Gln Cys Lys Ser Gly His Cys  Ile Pro Leu Arg Trp  Arg Cys Asp
    3620                3625                3630

Ala Asp Ala Asp Cys Met Asp  Gly Ser Asp Glu Glu  Ala Cys Gly
    3635                3640                3645

Thr Gly Val Arg Thr Cys Pro  Leu Asp Glu Phe Gln  Cys Asn Asn
    3650                3655                3660

Thr Leu Cys Lys Pro Leu Ala  Trp Lys Cys Asp Gly  Glu Asp Asp
    3665                3670                3675

Cys Gly Asp Asn Ser Asp Glu  Asn Pro Glu Glu Cys  Ala Arg Phe
    3680                3685                3690

Val Cys Pro Pro Asn Arg Pro  Phe Arg Cys Lys Asn  Asp Arg Val
    3695                3700                3705

Cys Leu Trp Ile Gly Arg Gln  Cys Asp Gly Thr Asp  Asn Cys Gly
    3710                3715                3720

Asp Gly Thr Asp Glu Glu Asp  Cys Glu Pro Pro Thr  Ala His Thr
    3725                3730                3735

Thr His Cys Lys Asp Lys Lys  Glu Phe Leu Cys Arg  Asn Gln Arg
    3740                3745                3750

Cys Leu Ser Ser Ser Leu Arg  Cys Asn Met Phe Asp  Asp Cys Gly
    3755                3760                3765

Asp Gly Ser Asp Glu Glu Asp  Cys Ser Ile Asp Pro  Lys Leu Thr
    3770                3775                3780

Ser Cys Ala Thr Asn Ala Ser  Ile Cys Gly Asp Glu  Ala Arg Cys
    3785                3790                3795

Val Arg Thr Glu Lys Ala Ala  Tyr Cys Ala Cys Arg  Ser Gly Phe
    3800                3805                3810

His Thr Val Pro Gly Gln Pro  Gly Cys Gln Asp Ile  Asn Glu Cys
    3815                3820                3825

Leu Arg Phe Gly Thr Cys Ser  Gln Leu Cys Asn Asn  Thr Lys Gly
    3830                3835                3840

Gly His Leu Cys Ser Cys Ala  Arg Asn Phe Met Lys  Thr His Asn
    3845                3850                3855

Thr Cys Lys Ala Glu Gly Ser  Glu Tyr Gln Val Leu  Tyr Ile Ala
    3860                3865                3870

Asp Asp Asn Glu Ile Arg Ser  Leu Phe Pro Gly His  Pro His Ser
    3875                3880                3885

Ala Tyr Glu Gln Ala Phe Gln  Gly Asp Glu Ser Val  Arg Ile Asp
    3890                3895                3900

Ala Met Asp Val His Val Lys  Ala Gly Arg Val Tyr  Trp Thr Asn
    3905                3910                3915

Trp His Thr Gly Thr Ile Ser  Tyr Arg Ser Leu Pro  Pro Ala Ala
    3920                3925                3930

Pro Pro Thr Thr Ser Asn Arg  His Arg Arg Gln Ile  Asp Arg Gly
    3935                3940                3945

Val Thr His Leu Asn Ile Ser  Gly Leu Lys Met Pro  Arg Gly Ile
    3950                3955                3960

Ala Ile Asp Trp Val Ala Gly  Asn Val Tyr Trp Thr  Asp Ser Gly
    3965                3970                3975

Arg Asp Val Ile Glu Val Ala  Gln Met Lys Gly Glu  Asn Arg Lys
    3980                3985                3990

Thr Leu Ile Ser Gly Met Ile  Asp Glu Pro His Ala  Ile Val Val
    3995                4000                4005
```

```
Asp Pro  Leu Arg Gly Thr Met  Tyr Trp Ser Asp Trp  Gly Asn His
    4010              4015                  4020

Pro Lys  Ile Glu Thr Ala Ala  Met Asp Gly Thr Leu  Arg Glu Thr
    4025              4030                  4035

Leu Val  Gln Asp Asn Ile Gln  Trp Pro Thr Gly Leu  Ala Val Asp
    4040              4045                  4050

Tyr His  Asn Glu Arg Leu Tyr  Trp Ala Asp Ala Lys  Leu Ser Val
    4055              4060                  4065

Ile Gly  Ser Ile Arg Leu Asn  Gly Thr Asp Pro Ile  Val Ala Ala
    4070              4075                  4080

Asp Ser  Lys Arg Gly Leu Ser  His Pro Phe Ser Ile  Asp Val Phe
    4085              4090                  4095

Glu Asp  Tyr Ile Tyr Gly Val  Thr Tyr Ile Asn Asn  Arg Val Phe
    4100              4105                  4110

Lys Ile  His Lys Phe Gly His  Ser Pro Leu Val Asn  Leu Thr Gly
    4115              4120                  4125

Gly Leu  Ser His Ala Ser Asp  Val Val Leu Tyr His  Gln His Lys
    4130              4135                  4140

Gln Pro  Glu Val Thr Asn Pro  Cys Asp Arg Lys Lys  Cys Glu Trp
    4145              4150                  4155

Leu Cys  Leu Leu Ser Pro Ser  Gly Pro Val Cys Thr  Cys Pro Asn
    4160              4165                  4170

Gly Lys  Arg Leu Asp Asn Gly  Thr Cys Val Pro Val  Pro Ser Pro
    4175              4180                  4185

Thr Pro  Pro Pro Asp Ala Pro  Arg Pro Gly Thr Cys  Asn Leu Gln
    4190              4195                  4200

Cys Phe  Asn Gly Gly Ser Cys  Phe Leu Asn Ala Arg  Arg Gln Pro
    4205              4210                  4215

Lys Cys  Arg Cys Gln Pro Arg  Tyr Thr Gly Asp Lys  Cys Glu Leu
    4220              4225                  4230

Asp Gln  Cys Trp Glu His Cys  Arg Asn Gly Gly Thr  Cys Ala Ala
    4235              4240                  4245

Ser Pro  Ser Gly Met Pro Thr  Cys Arg Cys Pro Thr  Gly Phe Thr
    4250              4255                  4260

Gly Pro  Lys Cys Thr Gln Gln  Val Cys Ala Gly Tyr  Cys Ala Asn
    4265              4270                  4275

Asn Ser  Thr Cys Thr Val Asn  Gln Gly Asn Gln Pro  Gln Cys Arg
    4280              4285                  4290

Cys Leu  Pro Gly Phe Leu Gly  Asp Arg Cys Gln Tyr  Arg Gln Cys
    4295              4300                  4305

Ser Gly  Tyr Cys Glu Asn Phe  Gly Thr Cys Gln Met  Ala Ala Asp
    4310              4315                  4320

Gly Ser  Arg Gln Cys Arg Cys  Thr Ala Tyr Phe Glu  Gly Ser Arg
    4325              4330                  4335

Cys Glu  Val Asn Lys Cys Ser  Arg Cys Leu Glu Gly  Ala Cys Val
    4340              4345                  4350

Val Asn  Lys Gln Ser Gly Asp  Val Thr Cys Asn Cys  Thr Asp Gly
    4355              4360                  4365

Arg Val  Ala Pro Ser Cys Leu  Thr Cys Val Gly His  Cys Ser Asn
    4370              4375                  4380

Gly Gly  Ser Cys Thr Met Asn  Ser Lys Met Met Pro  Glu Cys Gln
    4385              4390                  4395

Cys Pro  Pro His Met Thr Gly  Pro Arg Cys Glu Glu  His Val Phe
```

-continued

```
    4400                  4405                  4410

Ser Gln  Gln Gln Pro Gly His  Ile Ala Ser Ile Leu  Ile Pro Leu
    4415                  4420                  4425

Leu Leu  Leu Leu Leu Leu Val  Leu Val Ala Gly Val  Val Phe Trp
    4430                  4435                  4440

Tyr Lys  Arg Arg Val Gln Gly  Ala Lys Gly Phe Gln  His Gln Arg
    4445                  4450                  4455

Met Thr  Asn Gly Ala Met Asn  Val Glu Ile Gly Asn  Pro Thr Tyr
    4460                  4465                  4470

Lys Met  Tyr Glu Gly Gly Glu  Pro Asp Asp Val Gly  Gly Leu Leu
    4475                  4480                  4485

Asp Ala  Asp Phe Ala Leu Asp  Pro Asp Lys Pro Thr  Asn Phe Thr
    4490                  4495                  4500

Asn Pro  Val Tyr Ala Thr Leu  Tyr Met Gly Gly His  Gly Ser Arg
    4505                  4510                  4515

His Ser  Leu Ala Ser Thr Asp  Glu Lys Arg Glu Leu  Leu Gly Arg
    4520                  4525                  4530

Gly Pro  Glu Asp Glu Ile Gly  Asp Pro Leu Ala
    4535                  4540

<210> SEQ ID NO 5
<211> LENGTH: 19
<212> TYPE: RNA
<213> ORGANISM: Homo sapiens

<400> SEQUENCE: 5
ccacgugucu gcccaauua                                                     19

<210> SEQ ID NO 6
<211> LENGTH: 19
<212> TYPE: RNA
<213> ORGANISM: Homo sapiens

<400> SEQUENCE: 6
gacaggagcu acaaaguaa                                                     19

<210> SEQ ID NO 7
<211> LENGTH: 19
<212> TYPE: RNA
<213> ORGANISM: Homo sapiens

<400> SEQUENCE: 7
ccgaagagcu ugacuacuu                                                     19

<210> SEQ ID NO 8
<211> LENGTH: 19
<212> TYPE: RNA
<213> ORGANISM: Homo sapiens

<400> SEQUENCE: 8
ccaugaauau cacagcuua                                                     19
```

COMPOSITIONS AND METHODS FOR TREATMENT AND PREVENTION OF ALZHEIMER'S DISEASE

CROSS-REFERENCE TO RELATED APPLICATIONS

This application claims the benefit of U.S. Provisional Appl. No. 63/170,294, filed Apr. 2, 2021, the contents of which are hereby incorporated by reference in their entirety.

STATEMENT REGARDING FEDERALLY SPONSORED RESEARCH OR DEVELOPMENT

This invention was made with government support under Grant Numbers HL135743, HL007698, HL145952, AG063347, and AG073236 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 94,332 Byte ASCII (Text) file named "Sequence_listing_ST25.txt," created on Apr. 1, 2022.

FIELD OF THE INVENTION

The field of the invention relates to medicine, in particular therapeutics for the treatment and prevention of Alzheimer's disease.

BACKGROUND OF THE INVENTION

Cognitive decline in Alzheimer's disease is closely linked to aggregated forms of tau which form neurofibrillary tangles ("NFT") that initiate in the entorhinal cortex and spread as the disease progresses (Hyman et al., *Science* (80-), (1984), 225, 1168-1170; Serrano-Pozo et al., *J. Neuropathol. Exp. Neurol.*, (2013), 72, 1182-1192). How this occurs is not clear, but the process may involve trans-synaptic transfer of tau between neurons or uptake of extracellular tau that is constitutively secreted from neurons (Medina et al., *Cell. Neurosci.*, (2014) 8, 1-7; Wegmann et al., *Sci. Adv.*, (2019), 5; Takeda et al., *Nat. Commun.*, (2015) 6; Chai et al., *Neurobiol. Dis.*, (2012), 48, 356-366; Merezhko et al., *Cell Rep.*, (2018), 25, 2027-2035.e4; Pooler et al., *EMBO Rep.*, (2013), 14, 389-394). Specific receptors involved in these processes have remained elusive.

Progressive accumulation of protein aggregates throughout the brain is a common feature of many neurodegenerative diseases and dementias, including Alzheimer's disease ("AD"). The two primary lesions in AD are neurofibrillary tangles ("NFT") and senile plaques. NFT consists of abnormal accumulations of excessively phosphorylated forms of the microtubule-associated protein tau within the cytoplasm of certain neurons, while senile plaques consist of a central core of β-amyloid ("Aβ"), surrounded by abnormal neuronal processes. The presence of extracellular tau in brain interstitial fluid led to the discovery that tau is constitutively secreted from neurons which increases during neuronal activity and upon aging (Chai et al., *Neurobiol. Dis.*, (2012), 48, 356-366; Merezhko et al., *Cell Rep.*, (2018), 25, 2027-2035.e4; Pooler et al., *EMBO Rep.*, (2013), 14, 389-394;

Yamada et al., *J. Exp. Med.*, (2014), 211, 387-393; Huijbers et al., *J. Neurosci.*, (2019), 39, 548-556; Harrison et al., *Ann. Neurol.*, (2019), 85, 229-240). In mouse models of AD in which human mutant P301L tau is over-expressed in the entorhinal cortex, aggregated tau accumulates in brain regions with neuronal projections from the entorhinal cortex such as the dentate gyrus supporting the notion that the pathological tau protein can spread from one anatomical region of the brain to another (Polydoro et al., *J. Neurosci.*, (2013), 33, 13300-13311; De Calignon et al., *Neuron*, (2012), 73, 685-697; Liu et al., *PLoS One* 7, (2012), 1-9; Harris et al., *PLoS One*, (2012), 7). This process appears to be exacerbated in the presence of amyloid pathology (Pooler et al., *Commun.*, (2015), 3, 14). Extracellular tau is toxic to neurons and can induce accumulation and aggregation of intracellular tau (Yamada et al., *Front. Neurosci.*, (2017), 11, 1-5; Swanson et al., *J. Alzheimer's Dis.*, (2017), 58, 803-820). Monomeric forms of tau gain entry into cells by multiple processes which include a rapid dynamin-dependent pathway as well as a slower non-specific actin-dependent pathway (Evans et al., *Cell Rep.*, (2018), 22, 3612-3624). The entry of aggregated tau into cells appears to be largely dynamin dependent and involves heparin sulfate proteoglycans (Evans et al., *Cell Rep.*, (2018), 22, 3612-3624; Holmes et al., *Proc. Natl. Acad. Sci. U.S.A*, (2013), 110). Until now, the receptor(s) involved in these processes have not been identified.

What is needed are new compositions and methods that are useful to treat and prevent AD. The foregoing description of the background is provided to aid in understanding the invention, and is not admitted to be or to describe prior art to the invention.

SUMMARY OF THE INVENTION

It is to be understood that both the foregoing general description of the invention and the following detailed description are exemplary, and thus do not restrict the scope of the invention.

Here, the present inventors show that the low-density lipoprotein ("LDL") receptor-related protein 1 ("LRP1") functions as an endocytic receptor for tau that mediates its internalization into cells and its lysosomal degradation. Tau internalization is inhibited by LRP1 antagonists and is inefficient in cells lacking LRP1. Finally, the data of the present disclosure demonstrates that apolipoprotein E ("ApoE") inhibits tau internalization, with the ApoE4 isoform being a more potent inhibitor than other ApoE isoforms. The ability of ApoE4 to prevent the LRP1-mediated uptake of tau may disrupt the normal physiological process of tau catabolism, leading to tau uptake by other mechanisms and exacerbating the progression of tau-mediated cognitive loss.

The present data provides that the interaction of tau with LRP1 may be important for the progression of AD and that the identification of agents capable of blocking the interaction between tau and LRP1 could be beneficial for the treatment of AD. This is supported by demonstrating that LRP1 expressing cells, but not those deficient in LRP1, promote the seeding of tau polymers isolated from human AD brains.

The data further provide herein that SorLA, a receptor for ApoE, also known as Sortilin Related Receptor 1, or SORL1, could play a role similar to that of LRP1 regarding the uptake of tau into human neurons. Antagonists of LRP1 or SorLA can be useful as therapeutic agents for treating or preventing AD by preventing tau internalization. In some aspects, the present invention provides methods of preventing tau internalization in cells in a subject in need thereof, the method comprising administering at least one LRP1 antagonist and/or at least one SorLA antagonist. The present studies confirm that tau internalization in cells is attenuated by the LRP1 antagonist known as receptor associated protein ("RAP"). In some embodiments, LRP1 antagonists include antibodies, such as monoclonal antibodies, or immunoglobulin variants. In some embodiments, LRP1 antagonists include, agents such as nucleic acids that inhibit the expression of LRP1, where such nucleic acids can be RNAs, DNAs, or a combination thereof, ribozymes, small interfering RNAs ("siRNAs"), or short hairpin RNAs ("shRNAs"). Suitable RNAs can be designed with the aid of a computer program. Nucleic acid LRP1 antagonists can be delivered to a subject in, for example, a viral vector, or lipid or lipid-like particle. In some embodiments, the LRP1 antagonists include proteins, peptides, lipids, carbohydrates, organic molecules, inorganic molecules and peptidomimetics. In some embodiments, LRP1 antagonists include but are not limited to agents that disrupt the binding between LRP1 and myelin-associated glycoprotein (MAG), oligodendrocyte myelin glycoprotein (OMgp), Nogo-A, Nogo-B, Nogo-C and/or fragments thereof, lactoferrin, suramin, $\alpha_2$-macroglobulin and a soluble LRP1 receptor polypeptide.

The LRP1 antagonist or SorLA antagonist can be administered by topical, intravenous, subcutaneous, intramuscular, intracutaneous, transcutaneous, intrathecal, intranasal, intraarterial, rectal, intragastric, parenteral, or oral administration.

The present invention also provides pharmaceutical compositions for the treatment and/or prevention of Alzheimer's disease, comprising at least one LRP1 antagonist and/or at least one SorLA antagonist.

The LRP1 antagonist or SorLA antagonist can be RAP or a fragment or derivative thereof, or can be a species of one of the classes of materials identified above as being LRP1 antagonists. In certain embodiments, compositions of the invention can further comprise a pharmaceutically acceptable carrier.

In some embodiments, the antagonist comprises a fragment of RAP that comprises the D3 domain or RAP.

In another aspect, the invention provides a method of screening for potential antagonists of LRP1 or SorLA that reduce internalization of tau in cells. In some embodiments, the method comprises providing a cell expressing LRP1 and/or SorLA or a functional equivalent of LRP1 and/or SorLA; providing tau protein to the cell, wherein the tau protein is extracellular; treating the cell with a potential LRP1 or SorLA antagonist; and assaying the cellular uptake of tau. In some embodiments, the method comprises comparing the cellular uptake of tau in the cell with cells that have not been treated with the antagonist.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

Figure 1:
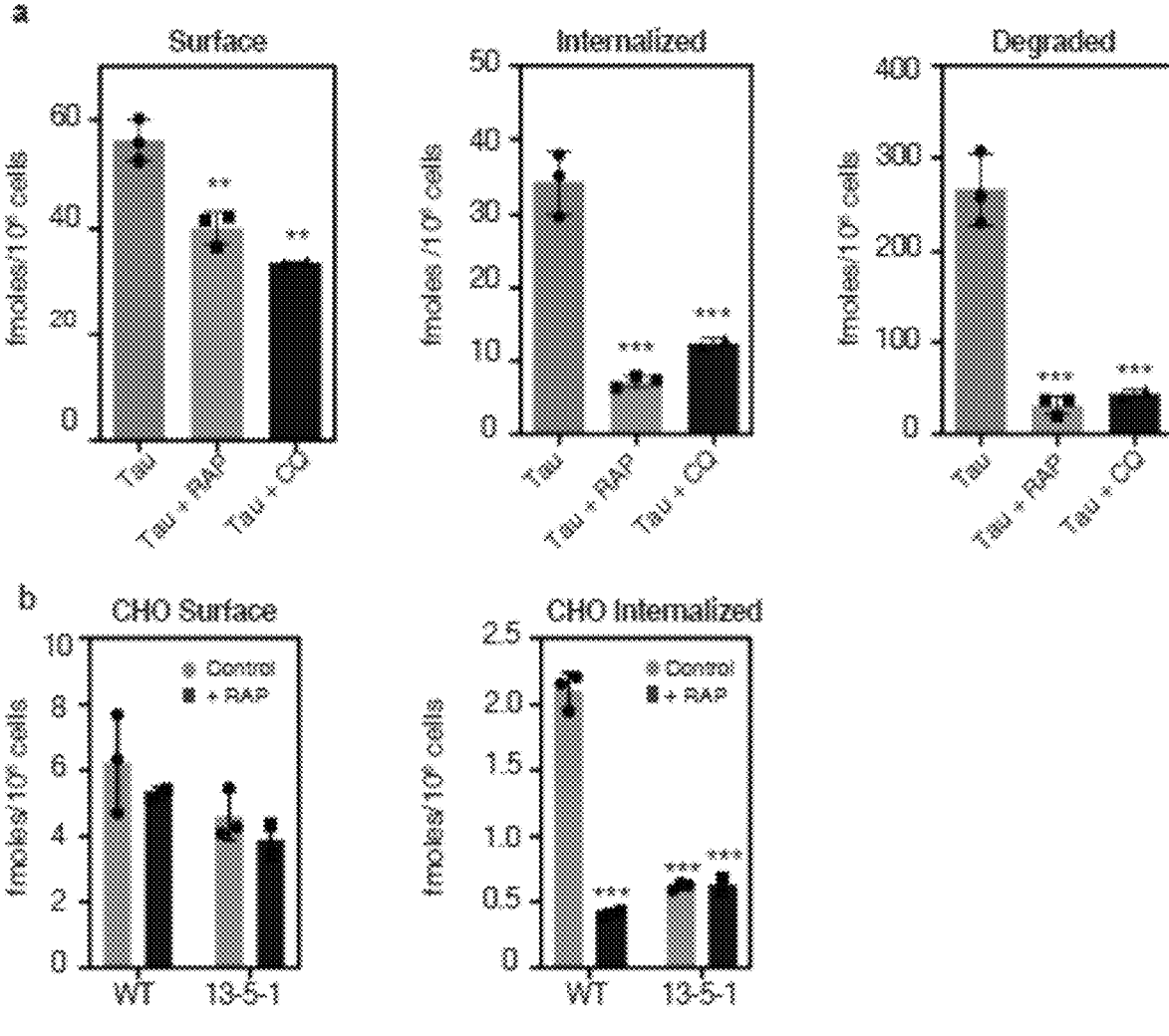
FIG. 1. LRP1 is an endocytic receptor for tau. a) WI-38 cells were incubated with 20 nM $^{125}$I-labeled tau in the absence or presence of 1 μM RAP or 100 μM chloroquine (CQ) for 2 hours at 37° C. The amounts of surface bound, internalized and degraded $^{125}$I-tau were quantified. b) Wild type (WT) or LRP1-deficient CHO 13-5-1 cells were incubated with $^{125}$I-tau in the absence or presence of 1 μM RAP for 2 hours at 37° C. The amount of surface bound and internalized $^{125}$I-tau was quantified. (*P<0.0001, P<0.003). c) WT and LRP1 deficient CHO 13-5-1 cells were incubated at 37° C. at the indicated times with $^{125}$I-tau in the absence or presence of 1 μM RAP or 20 μg/mL heparin. The amounts of surface bound and internalized $^{125}$I-tau were quantified. d) WT, LRP1-deficient CHO 13-5-1, or HSPG-deficient CHO K1 cells were incubated with $^{125}$I-tau in the absence or presence of 1 μM RAP or 20 μg/mL heparin for 2 hours at 37° C. and the amounts of surface bound and internalized $^{125}$I-tau was quantified. All data are expressed as mean±SEM from three independent replicates. Each experiment was performed multiple times. (*P<0.0007, P<0.003, *P<0.05; statistical analysis was performed using one-way analysis of variance (ANOVA) and Tukey post-hoc test (a), two-way ANOVA with Sidak post-hoc test (b,d).
Figure 1:
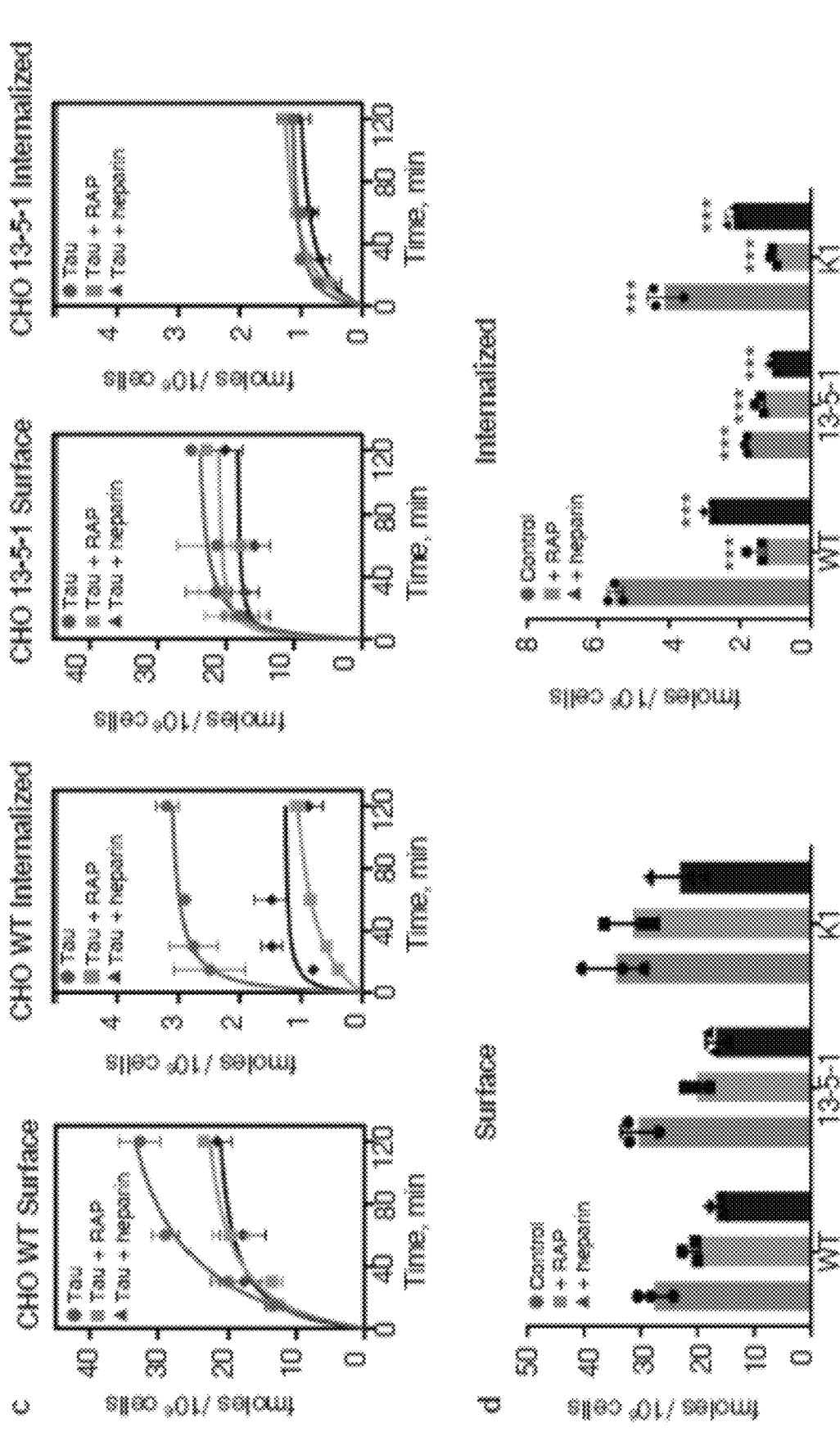

7 used to assess LRP1 binding. Data were y-transformed using CT HMW as control because there is no discernable HMW tau in the CT HMW sample.

DETAILED DESCRIPTION OF THE INVENTION

Tau is an intracellular microtubule-associated protein that is hyperphosphorylated and forms "tangles" in neurons of AD patients. Some investigators have suggested that the cognitive symptoms of this disease correlate with intraneu-ronal aggregation of tau. Experiments have shown that aggregated tau can spread from cell to cell and from one region of the brain to other regions. Tau is secreted by neurons and is taken up by receptor-mediated endocytosis. The receptors involved in this process have previously been unknown. The present inventors have discovered that tau binds avidly to LRP1, an endocytic receptor. Curiously, hyperphosphorylated forms of tau bind LRP1 with much lower affinity. The present disclosure provides that tau internalization in cells is attenuated by the LRP1 antagonist known as receptor associated protein ("RAP") and is reduced in LRP1-deficient cells. Confocal microscopy revealed that internalized tau colocalizes with LRP1 in endocytic vesicles. Most of the LRP1-mediated uptake of tau leads to its lysosomal degradation. The data herein further demonstrate that apolipoprotein E ("ApoE") inhibits LRP1-mediated tau internalization, with the ApoE4 isoform being a more potent inhibitor than other ApoE isoforms.

The studies herein provide that LRP1 functions as an endocytic receptor for tau, mediating the uptake of mono-meric forms of tau and resulting in its degradation. The ability of ApoE4 to modulate the LRP1-mediated uptake of tau may disrupt the normal physiological process of tau catabolism, leading to tau uptake by other mechanisms, causing the spreading of neurofibrillary tangles and exacer-bating the progression of tau-mediated cognitive loss. Of interest in this regard, the present studies in LRP1-deficient cell lines confirm that a RAP-insensitive second internal-ization mechanism occurs for tau, suggesting the existence of an LRP1-independent receptor-mediated process for tau uptake.

The studies herein also provide that SorLA plays a role in trafficking of pathological forms of tau to the cell cytoplasm, supporting aggregation of cytoplasmic tau. It is shown herein that tau binds with high affinity to SorLA. Further, expression of SorLA increases the internalization of tau and promotes cytosolic tau seeding induced by pathogenic forms of tau. It is also shown herein that siRNA knockdown of SorLA in H4 cells, increases tau degradation and decreases tau seeding, without altering the amount of tau internalized. The data herein reveal that endogenous SorLA directs tau away from lysosomal degradative pathways. Two mutations in the SorLA gene (G511R and N1358S) associated with increased risk of AD showed no difference in tau internal-ization. However, the N1358S mutant demonstrated a sig-nificant increase in tau seeding, revealing that the N1358S mutation may impact AD by mediating aberrant endolyso-somal escape of tau. The studies herein identify SorLA as a sorting receptor that contributes to seeding of pathogenic tau.

Thus, the interaction of tau with either LRP1 or SorLA has important implications for the progression of AD, and the identification of agents capable of blocking the interac-tion between tau and either LRP1 or SorLA could be beneficial for the treatment or prevention of AD.

Reference will now be made in detail to embodiments of the invention which, together with the drawings and the following examples, serve to explain the principles of the invention. These embodiments describe the invention in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the speci-fication may mean "one," but it is also consistent with the meaning of "one or more," "at least one" and "one or more than one." The use of the term "or" in the claims is used to mean "and/or" unless explicitly indicated to refer to alter-natives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alterna-tively described using the language "consisting essentially of" and/or "consisting of." As used herein, the term "about" means at most plus or minus 10% of the numerical value of the number with which it is being used.

It is contemplated that any method or composition described herein can be implemented with respect to any other method or composition described herein.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

The invention is based partly on the surprising discovery that LRP1 and SorLA function as endocytic receptors and/or mediate cellular trafficking for tau. The LRP1 and SorLA proteins are found in the plasma membrane of cells and are involved in receptor-mediated endocytosis or trafficking.

In one embodiment, the invention provides a method of reducing tau internalization and/or trafficking in neuronal cells comprising contacting the cells with an effective amount of an LRP1 antagonist.

In another embodiment, the invention provides a method of treating or preventing Alzheimer's disease in a subject in need thereof, comprising administering to the subject an effective amount of an LRP1 antagonist.

In another embodiment, the invention provides a method of reducing tau internalization and/or trafficking in neuronal cells comprising contacting the cells with an effective amount of a SorLA antagonist.

In another embodiment, the invention provides a method of treating or preventing Alzheimer's disease in a subject in need thereof, comprising administering to the subject an effective amount of an SorLA antagonist.

In another embodiment, the invention provides a method of reducing tau internalization and/or trafficking in neuronal cells comprising contacting the cells with i) an effective amount of an LRP1 antagonist; ii) an effective amount of a SorLA antagonist; or iii) an effective amount of an LRP1 antagonist and a SorLA antagonist.

In another embodiment, the invention provides a method of treating or preventing Alzheimer's disease in a subject in need thereof, comprising administering to the subject an effective amount of i) an LRP1 antagonist; ii) a SorLA antagonist; or iii) an LRP1 antagonist and a SorLA antagonist.

In another embodiment, the invention provides a method of screening for potential antagonists of LRP1 or SorLA that reduce internalization and/or trafficking of tau in cells, comprising i) providing a cell expressing LRP1 and/or SorLA or a functional equivalent of LRP1 and/or SorLA; ii) providing tau protein or a fragment or derivative thereof to the cell, wherein the tau protein or a fragment or derivative thereof is extracellular; iii) treating the cell with a potential LRP1 or SorLA antagonist; and iv) assaying the cellular uptake of tau or the fragment or derivative thereof.

LRP1 is a type-1 transmembrane receptor that binds over forty structurally and functionally distinct ligands, mediating their endocytosis and delivery to lysosomes. Strickland, et al., *Trends Endocrinol. Metab.* 2002, 13(2): 66-74.

The sortilin-related receptor SorLA is an endocytic receptor. It is encoded by the Sorl1 gene. The SORL1 gene encodes a 250 kDa type-1 transmembrane intracellular sorting receptor that shuttles between the trans-Golgi network (TGN), cell surface, and endosomes (Jacobsen et al., *J Biol Chem*, (1996), 271: 31379-31383; Yamazaki et al., *J Biol Chem*, (1996), 271: 24761-24768). SORL1 is expressed in neurons and several other cell types, and the SORLA protein is primarily localized to intracellular compartments, with ~10% of protein expressed on the cell surface (Zhang et al., *J Neurosci*, (2014), 34: 11929-11947; Jacobsen et al., *J Biol Chem*, (2001), 276: 22788-22796). It is a member of a family of VPS10P domain containing receptors and contains multiple functional domains, including a vacuolar protein sorting 10 protein (VPS10P) domain, a b-propeller domain, an EFG-type domain, a cluster of LDL ligand binding repeats similar to those found in LRP1, fibronectin type III domains, a leucine-rich domain, a transmembrane domain and an intracellular domain containing recognition sites for cytosolic adaptor proteins (Jacobsen et al., *J Biol Chem*, (1996), 271: 31379-31383; Willnow et al., *Nat Rev Neurosci*, (2008), 9: 899-909). SORLA is implicated in retromer function, which itself has been suggested to play a major role in Alzheimer pathogenesis (Fjorback et al., *J Neurosci*, (2012), 32: 1467-1480; Knupp et al., *Cell Rep*, (2020), 31: 107719).

SORLA is associated with both early and late onset forms of AD, and is a genetic risk factor for late-onset, sporadic AD (Rogaeva et al., *Nat Genet*, (2007), 39: 168-177; Scherzer et al., *Arch Neurol*, (2004), 61: 1200-1205; Reitz et al., *Arch Neurol*, (2011), 68: 99-106; Lambert et al., *Nat Genet*, (2013), 45: 1452-1458; Miyashita et al., *PLoS One*, (2013), 8: e58618). GWAS and whole exome sequencing studies have identified common and rare single nucleotide polymorphisms in SORL1 that are associated with early onset familial AD (Meng et al., *Neuroreport*, (2007), 18; Nicolas et al., *Mol Psychiatry*, (2016), 21: 831-836; Verheijen et al., *Acta Neuropathol*, (2016), 132: 213-224; Reitz et al., *Arch Neurol*, (2011), 68: 99-106; Pottier et al., *Mol Psychiatry*, (2012), 17: 875-879). Among these are the G511R mutant, which is located in the VPS10P domain and SORLA molecules harboring this missense mutation are deficient in AP binding (Caglayan et al., *Sci Transl Med*, (2014), 6: 223ra20). The N1358S mutation in the SORL1 gene was identified in an exome sequencing study of patients with early onset AD, and until now the functional consequences of this mutation have not been identified (Pottier et al., *Mol Psychiatry*, (2012), 17: 875-879).

As used herein, the term "antagonist" refers to a biological or chemical agent that acts within the body to reduce the activity of another chemical or biological substance. In the present invention, the antagonist can block, inhibit, reduce and/or decrease the activity of LRP1 or SorLA of a cell. In some embodiments of the invention, without being bound by theory, the antagonist combines, binds, or associates with LRP1 or SorLA such that at least some portion of the receptor is blocked, meaning reduced biological activity with respect to the biological activity in the diseased state. In certain embodiments, the antagonist combines, binds and/or associates with a protein that cooperates with LRP1 or SorLA and is necessary for tau internalization into mammalian cells or trafficking, such as Apolipoprotein E. In some embodiments, the antagonist can combine, bind, and/or associate with another protein or material that is a necessary part of the pathway leading to internalization or trafficking of tau into mammalian cells. The terms antagonist or inhibitor can be used interchangeably. In some embodiments, the LRP1 or SorLA antagonist blocks the interaction of tau and LRP1 or SorLA, and thereby reduces tau cellular internalization or trafficking. In some embodiments, the LRP1 or SorLA antagonist inhibits the cellular expression of LRP1 or SorLA. In some embodiments, the antagonist inhibits transcription of LRP1 or SorLA. In some embodiments, the antagonist inhibits translation of LRP1 or SorLA. In some embodiments, the antagonist reduces the stability, half-life, or cellular localization of LRP1 or SorLA.

As used herein, the term "subject" is not limiting and is used interchangeably with patient. In some embodiments, the term subject refers to animals, such as mammals and the like. For example, mammals contemplated include humans, primates, dogs, cats, sheep, cattle, goats, pigs, horses, chickens, mice, rats, rabbits, guinea pigs, and the like.

As used herein, the terms "effective amount" or "therapeutically effective amount" are interchangeable and refer to an amount that results in an improvement or remediation of at least one symptom of the disease or condition. Those of skill in the art understand that the effective amount may improve the patient's or subject's condition, but may not be a complete cure of the disease and/or condition. In some embodiments, the term "effective amount" corresponds to an amount administered that reduces the internalization or trafficking of tau in cells, mediated by LRP1 or SorLA. The "effective amount" can correspond to an amount administered to subjects or to cells directly.

As used herein, the term "inhibit" refers to the ability of the compound to block, partially block, interfere, decrease, reduce or deactivate a receptor such as LRP1 or SorLA. Thus, one of skill in the art understands that the term inhibit encompasses a complete and/or partial loss of activity of the receptor. Receptor activity may be inhibited by blockage of ligand binding sites on the receptor, by interference with the mechanism of expression of the receptor protein, or by other means. For example, a complete and/or partial loss of activity of the receptor may be indicated by a reduction in the extent of tau internalization or trafficking into neurons or other mammalian cells or a reduction in NFTs or senile plaques in the brain of a subject.

The term "preventing" as used herein refers to minimizing, reducing or suppressing the risk of developing a disease state or parameters relating to the disease state or progression of other abnormal or deleterious conditions.

The terms "treating" and "treatment" as used herein refer to administering to a subject a therapeutically effective amount of a composition so that the subject has an improvement in the disease or condition. The improvement is any observable or measurable improvement. Thus, one of skill in the art realizes that a treatment may improve the patient's condition but may not be a complete cure of the disease. Treating may also comprise treating subjects at risk of developing a disease and/or condition.

In some embodiments, the present invention provides a method of reducing the cellular uptake or trafficking of tau and thereby preventing and/or treating AD, the method comprising administering to the subject an effective amount of an agent that inhibits the activity of LRP1 receptor or SorLA.

Most notably, the present inventors have found that RAP, which antagonizes the binding of ligands to the LDL receptor class of receptors as well as to SorLA, dramatically reduces the extent of both tau internalization in cells and cellular-mediated degradation of tau (see Example 1). These results indicate that RAP could be an effective therapeutic agent against AD. As appropriate, RAP can be delivered to neuronal cells as a polypeptide (or variants or fragments thereof), or as a polynucleotide encoding RAP (e.g., in a plasmid or viral vector). In some embodiments, the antagonist comprises a fragment of RAP that comprises the D3 domain or RAP.

The present invention also provides for methods of treating or preventing Alzheimer's disease in subjects or for reducing tau internalization or trafficking in neuronal cells by administering an effective amount of LRP1 and/or SorLA antagonists, even those that are not known to interact directly with tau. See, e.g., Gonias, et al., U.S. Pat. Nos. 9,376,481, 10,308,718, 8,703,125; and U.S. Patent Appl. Publication No. 2015/0239973. In some embodiments, materials or methods for inhibiting any function of LRP1 or SorLA can be used in the present invention to treat or prevent AD or reduce internalization or trafficking of tau in neuronal cells.

For example, in various embodiments, the LRP1 inhibitor or antagonist competitively displaces, reduces, inhibits and/ or prevents binding of myelin-associated inhibitory proteins (e.g., myelin associated glycoprotein (MAG), oligodendrocyte myelin glycoprotein (OMgp), Nogo-A, Nogo-B, Nogo-C and/or fragments thereof) to LRP1.

One potentially useful approach is to raise an antibody to the LRP1 or SorLA protein, then administer an effective amount of the antibody to a subject. Methods of growing and manipulating antibodies are known in the art. See, e.g., Dayev, et al., *Modern technologies for creating synthetic antibodies for clinical application*, ActaNaturae 2009, 1(1): 32-50. In some embodiments, the antibody can be a monoclonal antibody. Useful antibodies can include but are not limited to polyclonal antibodies, raised against an immunogen comprising an amino acid sequence of a LRP1 or SorLA polypeptide or against an amino acid sequence encoded by a LRP1 or SORL1 nucleic acid.

The term "antibody" as used herein refers to polyclonal and monoclonal antibodies and fragments thereof, and immunologic binding equivalents thereof. The term "antibody" refers to a homogeneous molecular entity, or a mixture such as a polyclonal serum product made up of a plurality of different molecular entities, and broadly encompasses naturally-occurring forms of antibodies (for example, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatised variants thereof that retains the ability to specifically bind an epitope. Antibody derivatives may comprise a protein or chemical moiety conjugated to an antibody. A monoclonal antibody is capable of selectively binding to a target antigen or epitope. Antibodies may include, but are not limited to polyclonal antibodies, monoclonal antibodies (mAbs), humanized or chimeric antibodies, camelized antibodies, single chain antibodies (scFvs), Fab fragments, F(ab').sub.2 fragments, disulfide-linked Fvs (sdFv) fragments, for example, as produced by a Fab expression library, anti-idiotypic (anti-Id) antibodies, intrabodies, nanobodies, synthetic antibodies, and epitope-binding fragments of any of the above.

In some embodiments, the antagonist of LRP1 or SorLA is an inhibitory nucleic acid that inhibits the expression of LRP1 or SorLA. The nucleic acid can be an RNA, a DNA, or a combination thereof. For example, the inhibitory nucleic acid that inhibits the expression of LRP1 or SorLA can be a small interfering RNA ("siRNA"), a short hairpin RNA ("shRNA"), an antisense RNA, or a ribozyme. The siRNA, shRNA, or other inhibitory RNA can be designed with the aid of a computer program specifically prepared therefor. As appropriate, the inhibitory nucleic acid can be delivered in a viral vector, for example, a neurotropic viral vector. In some embodiments, the inhibitor of LRP1 is a siRNA or shRNA that specifically inhibits the expression of LRP1 or SorLA. In some embodiments, the siRNA or shRNA can be delivered in a lentiviral vector, a herpesvirus vector or an adenoviral vector. In some embodiments, the siRNA or shRNA can be delivered in pharmaceutical compositions comprising particles (e.g., nanoparticles) comprising one or more lipids, such as cationic lipids, such as ionizable amino lipids, or lipid-like molecules. See, e.g., U.S. Pat. No. 10,646,549, which is incorporated by reference herein.

In some embodiments, the LRP1 or SorLA antagonist comprises a nucleic acid molecule that comprises a nucleotide sequence that binds to at least a portion of a nucleotide sequence of LRP1 or SorLA. The nucleic acid molecule can be of any length, so long as at least part of the molecule hybridizes sufficiently to LRP1 or SorLA nucleic acid such as mRNA. The nucleic acid molecule can bind to any region of LRP1 or SorLA mRNA. In some embodiments, the nucleic acid molecule binds to a particular domain of LRP1 or SorLA mRNA.

In some embodiments, the nucleic acid sequence for LRP1 can be found in GenBank Accession No. NM_002332.3, which is incorporated herein by reference in its entirety, and corresponding to SEQ ID NO:1.

In some embodiments, the nucleic acid sequence for Sorl1 can be found in GenBank Accession No. NM_003105.6, which is incorporated herein by reference in its entirety, and corresponding to SEQ ID NO:2.

In some embodiments, a region of the nucleic acid molecule is at least 70%, 75%, 80%, 85%, 90%, 91%, 92%, 93%, 94%, 95%, 96%, 97%, 98% or 99% complementary to at least a portion of SEQ ID NOS:1 or 2. In some embodiments, the portion of SEQ ID NO:1 comprises a nucleic acid sequence corresponding to a portion of *Homo sapiens* LRP1. In some embodiments, the portion of SEQ ID NO:2 comprises a nucleic acid sequence corresponding to a portion of *Homo sapiens* SorLA.

In some embodiments, the composition can comprise a DNA molecule, such as an antisense DNA molecule. In some embodiments, the composition can comprise an RNA molecule, such as an anti-sense RNA molecule, a small interfering RNA (siRNA) molecule, or small hairpin RNA (shRNA) molecule, which may or may not be comprised on a vector, including a viral vector (such as an adeno-associated viral vector, an adenoviral vector, a retroviral vector, or a lentiviral vector) or a non-viral vector.

A target sequence on a target mRNA can be selected from a given cDNA sequence corresponding to the LRP1 or SorLA, in some embodiments, beginning 50 to 100 nt downstream (i.e., in the 3' direction) from the start codon. The target sequence can, however, be located in the 5' or 3' untranslated regions, or in the region nearby the start codon.

In one embodiment, the LRP1 or SorLA inhibitory agent comprises a nucleic acid molecule that comprises a nucleotide sequence that binds to at least a portion of a nucleotide sequence of LRP1 or SorLA mRNA. In some embodiments, the nucleic acid molecule is a DNA. In some embodiments, the nucleic acid molecule is an RNA.

In some embodiments, the composition comprises an anti-sense DNA. Anti-sense DNA binds with mRNA and prevents translation of the mRNA. The anti-sense DNA can be complementary to a portion of LRP1 or SorLA mRNA. In some embodiments, the anti-sense DNA is complementary to the entire reading frame of LRP1 or SorLA. In some embodiments, the anti-sense DNA is complementary to the entire reading frame of SEQ ID NOS:1 or 2. In some embodiments, the antisense DNA is complementary to a portion of SEQ ID NOS:1 or 2. In some embodiments, the antisense DNA is at least about 15 nucleotides, at least about 20 nucleotides, at least about 25 nucleotides, at least about 30 nucleotides, at least about 35 nucleotides, at least about 40 nucleotides, at least about 50 nucleotides, at least about 75 nucleotides, at least about 100 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1500 nucleotides, at least about 2000 nucleotides, at least about 2500 nucleotides, at least about 3000 nucleotides, at least about 3500 nucleotides, or at least about 4000 nucleotides.

In some embodiments, the composition comprises an anti-sense RNA. Anti-sense RNA binds with mRNA and prevents translation of the mRNA. The anti-sense RNA can be complementary to a portion of LRP1 or SorLA mRNA. In some embodiments, the anti-sense RNA is complementary to the entire reading frame of LRP1 or SorLA. In some embodiments, the anti-sense RNA is complementary to the entire reading frame of SEQ ID NOS:1 or 2. In some embodiments, the antisense RNA is complementary to a portion of SEQ ID NOS:1 or 2. In some embodiments, the antisense RNA is at least about 15 nucleotides, at least about 20 nucleotides, at least about 25 nucleotides, at least about 30 nucleotides, at least about 35 nucleotides, at least about 40 nucleotides, at least about 50 nucleotides, at least about 75 nucleotides, at least about 100 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1500 nucleotides, at least about 2000 nucleotides, at least about 2500 nucleotides, at least about 3000 nucleotides, at least about 3500 nucleotides, or at least about 4000 nucleotides.

In some embodiments, the antisense is complementary to a portion of the mRNA corresponding to SEQ ID NO:2, wherein the portion of mRNA comprises any of SEQ ID NOS:5-8.

It is also contemplated in the present invention that double-stranded RNA is used as an interference molecule, e.g., RNA interference (RNAi). In some embodiments, RNA interference is used to "knock down" or inhibit a particular gene of interest by simply injecting, bathing or feeding to the organism of interest the double-stranded RNA molecule. This technique selectively "knock downs" gene function without requiring transfection or recombinant techniques.

Another type of RNAi is often referred to as small interfering RNA (siRNA), which may also be utilized to inhibit LRP1 or SorLA. A siRNA may comprise a double stranded structure or a single stranded structure, the sequence of which is "substantially identical" to at least a portion of the target gene (see WO 04/046320, which is incorporated herein by reference in its entirety). "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ea., Academic Press, New York, 1993, and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA and CLUSTAL are applicable.

Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

One of skill in the art will appreciate that two polynucle- otides of different lengths may be compared over the entire length of the longer fragment. Alternatively, small regions may be compared. Normally sequences of the same length are compared for a final estimation of their utility in the practice of the present invention. It is preferred that there be 100% sequence identity between the double-stranded RNA ("dsRNA") for use as siRNA and at least 15 contiguous nucleotides of the target gene (e.g., LRP1 or SORL1), although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-comple- mentary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

There are several methods for preparing siRNA, such as chemical synthesis, in vitro transcription, siRNA expression vectors, and PCR expression cassettes. Irrespective of which method one uses, the first step in designing an siRNA molecule is to choose the siRNA target site, which can be any site in the target gene. In certain embodiments, one of skill in the art may manually select the target selecting region of the gene, which may be an ORF (open reading frame) as the target selecting region and may preferably be 50-100 nucleotides downstream of the "ATG" start codon. However, there are several readily available programs avail- able to assist with the design of siRNA molecules, for example siRNA Target Designer by Promega, siRNA Target Finder by GenScript Corp., siRNA Retriever Program by Imgenex Corp., EMBOSS siRNA algorithm, siRNA pro- gram by Qiagen, Ambion siRNA predictor, Ambion siRNA predictor, Whitehead siRNA prediction, and Sfold. Thus, it is envisioned that any of the above programs may be utilized to produce siRNA molecules that can be used in the present invention.

In some embodiments, the composition is an siRNA targeting LRP1 or SorLA. SiRNAs are small single or dsRNAs that do not significantly induce the antiviral response common among vertebrate cells but that do induce target mRNA degradation via the RNAi pathway. The term siRNA refers to RNA molecules that have either at least one double stranded region or at least one single stranded region and possess the ability to effect RNA interference (RNAi). It is specifically contemplated that siRNA can refer to RNA molecules that have at least one double stranded region and possess the ability to effect RNAi. The dsRNAs (siRNAs) may be generated by various methods including chemical synthesis, enzymatic synthesis of multiple templates, diges- tion of long dsRNAs by a nuclease with RNAse III domains, and the like. An "siRNA directed to" at least a particular region of LRP1 or SorLA means that a particular LRP1 or SorLA siRNA includes sequences that result in the reduction or elimination of expression of the target gene, i.e., the siRNA is targeted to the region or gene.

The nucleotide sequence of the siRNA is defined by the nucleotide sequence of its target gene. The LRP1 or SorLA siRNA contains a nucleotide sequence that is essentially identical to at least a portion of the target gene. In some embodiments, the siRNA contains a nucleotide sequence that is completely identical to at least a portion of the LRP1 or SorLA gene. Of course, when comparing an RNA sequence to a DNA sequence, an "identical" RNA sequence will contain ribonucleotides where the DNA sequence con- tains deoxyribonucleotides, and further that the RNA sequence will typically contain a uracil at positions where the DNA sequence contains thymidine.

In some embodiments, a LRP1 or SorLA siRNA com- prises a double stranded structure, the sequence of which is "substantially identical" to at least a portion of the target gene. "Identity," as known in the art, is the relationship between two or more polynucleotide (or polypeptide) sequences, as determined by comparing the sequences. In the art, identity also means the degree of sequence related- ness between polynucleotide sequences, as determined by the match of the order of nucleotides between such sequences. Identity can be readily calculated by standard practices in the art.

In some embodiments, the SorLA siRNA targets a portion of the mRNA corresponding to SEQ ID NO:2. In some embodiments, the target RNA sequence of the siRNA com- prises any of SEQ ID NOS:5-8.

One of skill in the art will appreciate that two polynucle- otides of different lengths may be compared over the entire length of the longer fragment. Alternatively, small regions may be compared. Normally sequences of the same length are compared for a final estimation of their utility in the practice of the present invention. In some embodiments, there is 100% sequence identity between the dsRNA for use as siRNA and at least 15 contiguous nucleotides of the target gene, although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-comple- mentary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

In some embodiments, the invention provides an LRP1 or SorLA siRNA that is capable of triggering RNA interfer- ence, a process by which a particular RNA sequence is destroyed (also referred to as gene silencing). In specific embodiments, LRP1 or SorLA siRNA are dsRNA molecules that are 100 bases or fewer in length (or have 100 base pairs or fewer in its complementarity region). In some embodi- ments, a dsRNA may be 15, 16, 17, 18, 19, 20, 21, 22, 23, 24, 25, 26, 27, 28, 29, 30, 40, 50, 60, 70, 80, 90, 100 110, 120, 130, 140, 150, 160, 170, 180, 190, 200, 225, 250, 275, 300, 325, 350, 375, 400, 450, 500, 550, 600, 650, 700, 750, 800, 850, 900, 950, or 1000 nucleotides or more in length. In certain embodiments, LRP1 or SorLA siRNA may be approximately 21 to 25 nucleotides in length. In some cases, it has a two nucleotide 3' overhang and a 5' phosphate. The particular LRP1 or SorLA RNA sequence is targeted as a result of the complementarity between the dsRNA and the particular LRP1 or SorLA RNA sequence. It will be under- stood that dsRNA or siRNA of the disclosure can effect at least a 20, 30, 40, 50, 60, 70, 80, 90 percent or more reduction of expression of a targeted LRP1 or SorLA RNA in a cell. dsRNA of the invention (the term "dsRNA" will be understood to include "siRNA" and/or "candidate siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule. In some embodiments, the complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous bases. In some embodiments, long dsRNA are employed in which "long" refers to dsRNA that are 1000 bases or longer (or 1000 base pairs or longer in complementarity region). The term "dsRNA" includes "long dsRNA", "intermediate dsRNA" or "small dsRNA" (lengths of 2 to 100 bases or base pairs in complementarity region) unless otherwise indicated. In some embodiments of the disclosure, dsRNA can exclude the use of siRNA, long dsRNA, and/or "intermediate" dsRNA (lengths of 100 to 1000 bases or base pairs in complementarity region).

It is specifically contemplated that a dsRNA may be a molecule comprising two separate RNA strands in which one strand has at least one region complementary to a region on the other strand. Alternatively, a dsRNA includes a molecule that is single stranded yet has at least one complementarity region as described above (such as when a single strand with a hairpin loop is used as a dsRNA for RNAi). For convenience, lengths of dsRNA may be referred to in terms of bases, which simply refers to the length of a single strand or in terms of base pairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

Strands or regions that are complementary may or may not be 100% complementary ("completely or fully complementary"). It is contemplated that sequences that are "complementary" include sequences that are at least 50% complementary, and may be at least 50%, 60%, 70%, 80%, or 90% complementary. In some embodiments, siRNA generated from sequence based on one organism may be used in a different organism to achieve RNAi of the cognate target gene. In other words, siRNA generated from a dsRNA that corresponds to a human gene may be used in a mouse cell if there is the requisite complementarity, as described above. Ultimately, the requisite threshold level of complementarity to achieve RNAi is dictated by functional capability. It is specifically contemplated that there may be mismatches in the complementary strands or regions. Mismatches may number at most or at least 1, 2, 3, 4, 5, 6, 7, 8, 9, 10, 11, 12, 13, 14, 15, 16, 17, 18, 19, 20, 21, 22, 23, 24, 25 residues or more, depending on the length of the complementarity region.

In some embodiments, the single RNA strand or each of two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or more (including the full-length of a particular's gene's mRNA without the poly-A tail) bases or base pairs. If the dsRNA is composed of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more bases on either or both ends (5' and/or 3') or as forming a hairpin loop between the complementarity regions.

In some embodiments, the strand or strands of dsRNA are 100 bases (or base pairs) or less. In specific embodiments, the strand or strands of the dsRNA are less than 70 bases in length. With respect to those embodiments, the dsRNA strand or strands may be from 5-70, 10-65, 20-60, 30-55, 40-50 bases or base pairs in length. A dsRNA that has a complementarity region equal to or less than 30 base pairs (such as a single stranded hairpin RNA in which the stem or complementary portion is less than or equal to 30 base pairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 base pairs or fewer. In some cases, a dsRNA may be processed in the cell into siRNA.

In some embodiments, the siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the disclosure can comprise a 3' overhang. As used herein, a "3' overhang" refers to at least one unpaired nucleotide extending from the 3'-end of a duplexed RNA strand.

Thus, in some embodiments, the LRP1 or SorLA siRNA of the invention comprises at least one 3' overhang of from 1 to about 6 nucleotides (which includes ribonucleotides or deoxynucleotides) in length, from 1 to about 5 nucleotides in length, from 1 to about 4 nucleotides in length, or from about 2 to about 4 nucleotides in length.

In some embodiments in which both strands of the LRP1 or SorLA siRNA molecule comprise a 3' overhang, the length of the overhangs can be the same or different for each strand. In some embodiments, the 3' overhang is present on both strands of the siRNA, and is 2 nucleotides in length. For example, each strand of the LRP1 or SorLA siRNA of the invention can comprise 3' overhangs of dithymidylic acid ("TT") or diuridylic acid ("uu").

In order to enhance the stability of the present LRP1 or SorLA siRNA, the 3' overhangs can be also stabilized against degradation. In some embodiments, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In some embodiments, the LRP1 or SorLA siRNA of the invention comprises the sequence AA(N19)TT or NA(N21), where N is any nucleotide. These LRP1 or SorLA siRNA comprise approximately 30-70% GC, and in some embodiments comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the LRP1 or SorLA siRNA of the invention comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In some embodiments, the LRP1 or SorLA siRNA of the disclosure can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the worldwide web at a website maintained by Dr. Thomas Tuschl, Department of Cellular Biochemistry, AG 105, Max-Planck-Institute for Biophysical Chemistry, 37077 Gottingen, Germany, and can be found by accessing the website of the Max Planck Institute and searching with the keyword "siRNA." Thus, in some embodiments, the sense strand of the present siRNA comprises a nucleotide sequence identical to any contiguous stretch of about 19 to about 25 nucleotides in the target mRNA.

Transcription factors are regulatory proteins that bind to a specific DNA sequence (e.g., promoters and enhancers) and regulate transcription of an encoding DNA region. Thus, transcription factors can be used to modulate the expression of LRP1 or SorLA. Typically, a transcription factor comprises a binding domain that binds to DNA (a DNA-binding domain) and a regulatory domain that controls transcription. Where a regulatory domain activates transcription, that regulatory domain is designated an activation domain. Where that regulatory domain inhibits transcription, that regulatory domain is designated a repression domain. More specifically, transcription factors such as Sp1/Sp3 can be used to modulate expression of LRP1 or SorLA.

In some embodiments, a transcription factor may be targeted by a composition of the invention. The transcription factor may be one that is associated with a pathway in which LRP1 or SorLA is involved. The transcription factor may be targeted with an antagonist of the invention, including siRNA to downregulate the transcription factor. Such antagonists can be identified by standard methods in the art, and in particular embodiments the antagonist is employed for treatment and or prevention of an individual in need thereof. In an additional embodiment, the antagonist is employed in conjunction with an additional compound, such as a composition that modulates ApoE. For example, the LRP1 antagonist or SorLA antagonist may be used in combination with an inhibitor of ApoE. When employed in combination, the antagonist of a transcription factor of a LRP1-related pathway or SorLA-related pathway may be administered prior to, during, and/or subsequent to the additional compound.

In some embodiments, an antisense molecule that binds to a translational or transcriptional start site, or splice junctions, can be used as an inhibitor. Antisense, ribozyme, and double-stranded RNA molecules target a particular sequence to achieve a reduction or elimination of a particular polypeptide, such as LRP1 or SorLA. Thus, it is contemplated that antisense, ribozyme, and double-stranded RNA, and RNA interference molecules are constructed and can be used to modulate LRP1 expression or SorLA expression.

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases, such as inosine, 5-methylcytosine, 6-methyladenine, hypoxanthine and others, in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, in some embodiments, antisense constructs with complementarity to regions within 50-200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Ribozymes are RNA-protein complexes that cleave nucleic acids in a site-specific fashion. Ribozymes have specific catalytic domains that possess endonuclease activity. For example, a large number of ribozymes accelerate phosphoester transfer reactions with a high degree of specificity, often cleaving only one of several phosphoesters in an oligonucleotide substrate. This specificity has been attributed to the requirement that the substrate bind via specific base-pairing interactions to the internal guide sequence ("IGS") of the ribozyme prior to chemical reaction. Ribozyme catalysis has primarily been observed as part of sequence specific cleavage/ligation reactions involving nucleic acids. For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to the therapeutic applications. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Designing and testing ribozymes for efficient cleavage of a target RNA is a process well known to those skilled in the art. The identification of operative and preferred sequences for use in LRP1 or SorLA targeted ribozymes is simply a matter of preparing and testing a given sequence, and is a routinely practiced screening method known to those of skill in the art.

In some embodiments, a useful LRP1 or SorLA antagonist can be a protein, a peptide, a lipid, a carbohydrate, an organic molecule, or an inorganic molecule. Exemplary inhibitors of LRP1 or SorLA function include, without limitation, soluble LRP1 or SorLA receptor polypeptides. In some embodiments, the soluble SorLA receptor polypeptide comprises a fragment of SorLA that comprises the VPS10P domain, corresponding to amino acid residues 82-753 of SEQ ID NO:3. In some embodiments, the soluble LRP1 can comprise a fragment that comprises one or more of clusters II, III and IV of the polypeptide. In some embodiments, the full length LRP1 amino acid sequence is SEQ ID NO:4.

Useful inhibitors can reduce, inhibit or eliminate ligand binding function, such as binding to myelin-associated inhibitory proteins including but not limited to myelin associated glycoprotein (MAG), oligodendrocyte myelin glycoprotein (OMgp), Nogo-A, Nogo-B, Nogo-C and/or fragments thereof, signaling function and/or expression of LRP1. LRP1 antagonists that interfere with ligand binding to LRP1 include without limitation receptor associated protein (RAP), fragments of RAP that comprise the D3 domain or RAP, lactoferrin, suramin and $\alpha_2$-macroglobulin.

The LRP1 or SorLA antagonist can be administered in a variety of ways and is not particularly limiting. In some embodiments, the agent is administered directly (topically), intravenously, subcutaneously, transcutaneously, intrathecally, intramuscularly, intracutaneously, intragastrically, intranasally, rectally, intra-arterially, parenterally, or orally.

In some embodiments, an effective amount of the antagonist of LRP1 or SorLA that is administered includes a dose of about 0.0001 nM to about 2000 μM. In some embodiments, amount administered is from about 0.01 nM to about 2000 μM; about 0.01 μM to about 0.05 μM; about 0.05 μM to about 1.0 μM; about 1.0 μM to about 1.5 μM; about 1.5 μM to about 2.0 μM; about 2.0 μM to about 3.0 μM; about 3.0 μM to about 4.0 μM; about 4.0 μM to about 5.0 μM; about 5.0 μM to about 10 μM; about 10 μM to about 50 μM; about 50 μM to about 100 μM; about 100 μM to about 200 μM; about 200 μM to about 300 μM; about 300 μM to about 500 μM; about 500 μM to about 1000 μM; about 1000 μM to about 1500 μM; and about 1500 μM to about 2000 μM. Of course, all of these amounts are exemplary, and any amount in-between these points is also expected to be of use in the invention.

In some embodiments, the antagonist can be administered parenterally or alimentarily. Parenteral administrations include, but are not limited to intravenously, intradermally, transdermally, intramuscularly, intraarterially, intrathecally, subcutaneous, or intraperitoneally. See, e.g., U.S. Pat. Nos. 6,613,308, 5,466,468, 5,543,158; 5,641,515; and 5,399,363 (each specifically incorporated herein by reference in its entirety). Alimentary administrations include, but are not limited to orally, buccally, rectally, or sublingually.

In some embodiments, the administration of the therapeutic compounds and/or the therapies of the present invention may include systemic, local and/or regional administrations, for example, topically (dermally, transdermally), via catheters, implantable pumps, dermal patches, transdermal patches, etc. Alternatively, other routes of administration are also contemplated such as, for example, arterial perfusion, intracavitary, intraperitoneal, intrapleural, intraventricular and/or intrathecal. The skilled artisan is aware of determining the appropriate administration route using standard methods and procedures. Other routes of administration are discussed elsewhere in the specification and are incorporated herein by reference.

Treatment methods involve treating an individual with an effective amount of a composition comprising an effective amount of antagonist of LRP1 or SorLA, or a related compound thereof.

As is well known in the art, a specific dose level of active compounds such as an antagonist of LRP1 or SorLA, or related-compounds thereof for any particular patient depends upon a variety of factors including the activity of the specific compound employed, the age, body weight, general health, sex, diet, time of administration, route of administration, rate of excretion, drug combination, and the severity of the particular disease undergoing therapy.

In some embodiments, the compound(s) or composition(s) can be administered to the subject once, such as by a single injection or deposition at or near the site of interest. In some embodiments, the compound(s) or composition(s) can be administered to a subject over a period of days, weeks, months or even years. In some embodiments, the compound(s) or composition(s) is administered at least once a day to a subject. Where a dosage regimen comprises multiple administrations, it is understood that the effective amount of the compound(s) or composition(s) administered to the subject can comprise the total amount of the compound(s) or composition(s) administered over the entire dosage regimen.

The present invention also contemplates therapeutic methods employing compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, α-tocopherol and the like; and the metal chelating agents such as citric acid, ethylenediamine tetraacetic acid (EDTA), sorbitol, tartaric acid, phosphoric acid and the like.

In some embodiments, the total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

For example, in one embodiment of the present invention directed to a method of treating or preventing AD in a subject by administering to the subject a formulation containing an effective amount of an antagonist of LRP1 or SorLA and a pharmaceutically acceptable carrier.

The active agents of the present invention can be administered alone or in combination with one or more active pharmaceutical agents. In some embodiments, the one or more active pharmaceutical agents are other drugs that are useful for treating Alzheimer's disease in the subject, such as cholinesterase inhibitors or N-methyl-D-aspartic acid (NMDA) receptor antagonists.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In some embodiments, the active agents of the present invention can be administered as a nanoparticle formulation.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol, which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

In one embodiment, the therapeutic compound is delivered transdermally. The term "transdermal delivery" as used herein means administration of the pharmaceutical composition topically to the skin wherein the active ingredient or its pharmaceutically acceptable salts, will be percutaneously delivered in a therapeutically effective amount.

In some embodiments, the composition to be applied transdermally further comprises an absorption enhancer. The term "absorption enhancer" as used herein means a compound which enhance the percutaneous absorption of drugs. These substances are sometimes also referred to as skin-penetration enhancers, accelerants, adjuvants and sorption promoters. Various absorption enhancers are known to be useful in transdermal drug delivery. U.S. Pat. Nos. 5,230,897, 4,863,970, 4,722,941, and 4,931,283 disclose some representative absorption enhancers used in transdermal compositions and for topical administration. In some embodiments, the absorption enhancer is N-lauroyl sarcosine, sodium octyl sulfate, methyl laurate, isopropyl myristate, oleic acid, glyceryl oleate or sodium lauryl sulfoacetate, or a combination thereof. In some embodiments, the composition contains on a weight/volume (w/v) basis the absorption enhancer in an amount of about 1-20%, 1-15%, 1-10% or 1-5%. In some embodiments, to enhance further the ability of the therapeutic agent(s) to penetrate the skin or mucosa, the composition can also contain a surfactant, an azone-like compound, an alcohol, a fatty acid or ester, or an aliphatic thiol.

In one embodiment, the therapeutic compound is delivered via a transdermal patch.

In some embodiments, the invention provides a transdermal patch comprising an effective amount of the therapeutic compound for treating or preventing Alzheimer's disease. In some embodiments, the transdermal patch further comprises an absorption enhancer.

In some embodiments, the transdermal composition can further comprise one or more additional excipients. Suitable excipients include without limitation solubilizers (e.g., $C_2$-$C_8$ alcohols), moisturizers or humectants (e.g., glycerol [glycerin], propylene glycol, amino acids and derivatives thereof, polyamino acids and derivatives thereof, and pyrrolidone carboxylic acids and salts and derivatives thereof), surfactants (e.g., sodium laureth sulfate and sorbitan monolaurate), emulsifiers (e.g., cetyl alcohol and stearyl alcohol), thickeners (e.g., methyl cellulose, ethyl cellulose, hydroxymethyl cellulose, hydroxypropyl cellulose, polyvinylpyrrolidone, polyvinyl alcohol and acrylic polymers), and formulation bases or carriers (e.g., polyethylene glycol as an ointment base). As a non-limiting example, the base or carrier of the composition can contain ethanol, propylene glycol and polyethylene glycol (e.g., PEG 300), and optionally an aqueous liquid (e.g., isotonic phosphate-buffered saline).

The method of the present invention employs the compounds identified herein for both in vitro and in vivo applications. For in vivo applications, the invention compounds can be incorporated into a pharmaceutically acceptable formulation for administration. Those of skill in the art can readily determine suitable dosage levels when the invention compounds are so used.

In accordance with a particular embodiment of the present invention, compositions comprising at least one LRP1 antagonist compound (as described above) and/or at least one SorLA antagonist, and a pharmaceutically acceptable carrier are contemplated.

Exemplary pharmaceutically acceptable carriers include carriers suitable for oral, intravenous, intrathecal, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The treatments may include various "unit doses." Unit dose is defined as containing a predetermined quantity of the therapeutic composition (an antagonist of LRP1 or SorLA or its related-compounds thereof) calculated to produce the desired responses in association with its administration, e.g., the appropriate route and treatment regimen. The quantity to be administered, and the particular route and formulation, are within the skill of those in the clinical arts. Also of importance is the subject to be treated, in particular, the state of the subject and the protection desired. A unit dose need not be administered as a single injection but may comprise continuous infusion over a set period of time.

In some embodiments, pharmaceutical compositions of the present invention comprise an effective amount of one or more Alzheimer's disease drugs, such as cholinesterase inhibitors or NMDA receptor antagonists, e.g., memantine (or related compounds or additional agent), dissolved or dispersed in a pharmaceutically acceptable carrier. In some embodiments, the compositions can comprise one or more of donepezil (Aricept), rivastigmine (Exelon), galantamine (Razadyne, formerly Reminyl), and memantine (Namenda). The compositions can comprise antagonists of the invention or can be administered separately from the compositions comprising the antagonist.

The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one Alzheimer's disease drug or related compounds or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compounds and compositions of the invention such as Alzheimer's disease therapeutics can comprise different types of carriers depending on whether it is to be administered in solid, liquid or aerosol form, and whether it needs to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compounds and compositions of the invention such as Alzheimer's disease therapeutics can be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the compounds and composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition can be combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of pharmaceutical lipid vehicle compositions that include compounds or compositions of the invention such as Alzheimer's therapeutics, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the Alzheimer's therapeutics may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylactic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments of the present invention, the compounds and compositions of the invention, such as Alzheimer's therapeutics are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like. See, e.g., U.S. Pat. Nos. 5,641,515; 5,580,579 and 5,792,451, each specifically incorporated herein by reference in its entirety. The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations that are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

In further embodiments, the compounds and compositions of the invention, such as Alzheimer's therapeutics can be administered via a parenteral route. As used herein, the term "parenteral" includes routes that bypass the alimentary tract. Specifically, the pharmaceutical compositions disclosed herein may be administered for example, but not limited to intravenously, intradermally, transdermally, intramuscularly, intraarterially, intraventricularly, intrathecally, subcutaneous, or intraperitoneally. See, e.g., U.S. Pat. Nos. 6,753,514; 6,613,308; 5,466,468; 5,543,158; 5,641,515; and 5,399,363 (each specifically incorporated herein by reference in its entirety).

In some embodiments, the therapeutic compound is administered intrathecally. In some embodiments, the compound is administered intrathecally via an implantable pump. In one embodiment, the implantable pump comprises a SynchroMed™ II pump that stores and delivers medication into the intrathecal space (Medtronic).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, dimethyl sulfoxide (DMSO), polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compounds and compositions of the invention, such as Alzheimer's therapeutics may be formulated for administration via various miscellaneous routes, for example, topical (i.e., transdermal) administration, mucosal administration (intranasal, vaginal, etc.) and/ or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described, e.g., in U.S. Pat. Nos. 5,756,353 and 5,804,212 (each specifically incorporated herein by reference in its entirety). Likewise, the delivery of drugs using intranasal microparticle resins and lysophosphatidylglycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

In some embodiments, tau and LRP1 and/or SorLA or a functional equivalent thereof can be used in screening assays for compounds which bind one or more of the proteins and which inhibit their interaction. In some embodiments, the screening methods can be conducted in cells, cell-free preparations, cellular homogenates, animals, or on one or more substrates, for example on surface plasmon resonance sensor chips. In some embodiments any of a tau antibody, tau or a fragment or derivative thereof (including fractions from brain, including from Alzheimer's patients), LRP1 and/or SorLA, and the potential antagonist can be coupled to a solid surface to assay competitive binding. In some embodiments, one or more of clusters II, III and IV of LRP1 are assayed for competition binding of tau or a fragment or derivative thereof using a test compound. In some embodiments, SorLA or a fragment comprising the VPS10P domain are assayed for competition binding of tau or a fragment or derivative thereof using a test compound.

In some embodiments, a tau antibody is bound to a surface, such as a surface plasmon resonance chip, and a sample comprising tau or a fragment or derivative thereof is added to the surface. In some embodiments, the source of tau comprises a sample from brain, e.g., of an Alzheimer's patient, such as a homogenate, or size exclusion purified fraction, to bind tau to the antibody. Tau binding can be confirmed by a second tau antibody, in some embodiments. LRP1 or SorLA, or tau binding fragments or derivatives thereof are added to the immobilized tau, and can be added in combination with a test compound to be assayed for competitive binding to displace the bound LRP1 or SorLA from the surface or to prevent binding.

In some embodiments, the invention provides a screening assay to test for compounds that inhibit the interaction of tau with LRP1 or SorLA comprising i) providing a tau antibody bound to a substrate; ii) adding a sample to the substrate comprising tau or a fragment or derivative thereof; iii) adding LRP1 and/or SorLA and a test compound to the substrate; iv) detecting binding of LRP1 and/or SorLA to the substrate or detecting the absence or reduction of binding of LRP1 and/or SorLA to the substrate in the presence of the test compound.

In another embodiment, the invention provides a screening assay to test for compounds that inhibit the interaction of tau with LRP1 or SorLA comprising i) providing a LRP1 or SorLA antibody bound to a substrate; ii) adding a sample to the substrate comprising LRP1 or SorLA or a fragment or derivative thereof; iii) adding a source of tau or a fragment or derivative thereof and a test compound to the substrate; iv) detecting binding of tau or a fragment or derivative thereof to the substrate or detecting the absence or reduction of binding of tau or a fragment or derivative thereof to the substrate in the presence of the test compound.

In some embodiments, the substrate is a surface plasmon resonance sensor chip. In some embodiments, tau or LRP1 or SorLA binding can be confirmed by a second tau or LRP1 or SorLA antibody.

In some embodiments, the invention provides a method of screening for potential antagonists of LRP1 or SorLA that reduce internalization and/or trafficking of tau in cells. In some embodiments, the method comprises providing a cell expressing LRP1 and/or SorLA or a functional equivalent of LRP1 and/or SorLA; providing tau or a fragment or derivative thereof protein to the cell, wherein the tau protein or fragment or derivative thereof is extracellular; treating the cell a potential LRP1 or SorLA antagonist; and assaying the cellular uptake of tau or the fragment or derivative thereof. In some embodiments, the method comprises comparing the cellular uptake of tau or the fragment or derivative thereof in the cell with cells that have not been treated with the antagonist.

In some embodiments, the screening procedures involve producing appropriate cells, which can be neuronal cells which express LRP1 and/or SorLA or functional equivalents thereof. Such cells can include neuronal or non-neuronal cells from mammals, yeast, *Drosophila* or *E. coli*. In some embodiments, the cells express the polypeptide endogenously. In other embodiments, the cells have been transfected or engineered to express the polypeptide. In some embodiments, cells expressing the protein (or extracts or purified preparations from cells) are contacted with a test compound to observe stimulation or inhibition of a functional response. In some embodiments, for assaying compounds that inhibit expression of LRP1 or SorLA, the levels of LRP1 or SORL1 mRNA or protein can be assayed after contacting the cells with the test compound. In some embodiments, the expression level of an endogenous LRP1 or SorLA target gene is assayed. In some embodiments, the cells can comprise a reporter gene located downstream of one or more LRP1 or SORL1 promoter elements and inhibition of the reporter gene is assayed.

In some embodiments, assays test binding of a candidate compound to LRP1, SorLA, or tau or assays involving competition with a labeled competitor. In some embodiments, inhibitors of activation can be tested in the presence of an agonist and the effect on activation by the agonist in the presence of the candidate compound is observed.

Examples of antagonists can include antibodies, peptides, carbohydrates, lipids, or small molecules which bind to one or more of the proteins so that binding between tau and LRP1 or SorLA is inhibited. These agents can be selected and screened 1) at random, 2) by a rational selection or 3) by design using for example, protein or ligand modeling techniques (preferably, computer modeling).

All publications herein are incorporated by reference to the same extent as if each individual publication or patent application was specifically and individually indicated to be incorporated by reference.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

Example 1. LRP1 Regulates Tau Internalization in a Process Modulated by Apolipoprotein E The current study tested the hypothesis that the LDL receptor-related protein 1 (LRP1) functions as an endocytic receptor for tau. LRP1 is a large endocytic and signaling receptor that binds numerous ligands, including amyloid-precursor protein (APP) and β-amyloid, and is one of the major neuronal apolipoprotein E ("apoE") receptors that has been linked to AD (Kounnas et al. *Cell* 82, (1995), 331-340; Ulery et al. *J. Biol. Chem.*, (2000), 275, 7410-7415; Waldron et al. *Neurobiol. Dis.*, (2008), 31, 188-197; Shibata et al. *J. Clin. Invest.*, (2000), 106, 1489-1499; Storck et al. *J. Clin. Invest.*, (2016), 126, 123-136; Holtzman et al., *Cold Spring Harb. Perspect. Med.*, (2012), 2, 1-24). LRP1 is an endocytic receptor for tau.

To identify mechanisms by which monomeric forms of tau are internalized by cells, the surface binding, internalization and degradation of $^{125}$I-labeled tau in WI-38 fibroblasts was investigated. Alternative splicing of the MAPT gene gives rise to six variants of tau protein, with the 2N4R variant the largest. In the present experiments, the 2N4R variant was used, unless otherwise noted. To determine if a member of the LDL receptor family is involved in this process, the receptor associated protein (RAP), which antagonizes the binding of ligands to this class of receptors, was used (Herz et al., *J. Biol. Chem.*, (1991), 266, 21232-21236). The results of this experiment reveal that while excess RAP slightly impacts the binding of $^{125}$I-labeled tau to cell surfaces, it dramatically reduces the extent of tau internalization and cellular-mediated degradation (FIG. 1a). These experiments also revealed that internalized tau is degraded in lysosomal compartments, as evidenced by the ability of the lysosomal inhibitor, chloroquine, to block its degradation. While most LRP1 ligands are effectively trafficked to the lysosomes for degradation, it is conceivable that some tau may escape this pathway. As a precedent for this, the LRP1 ligand, *Pseudomonas* exotoxin A, is cleaved within endosomal compartments releasing a 37 kDa domain that is translocated to the cytosol where it ADP ribosylates elongation factor 2 (Kounnas et al., *J. Biol. Chem.*, (1992), 267, 12420-12423).

To test the hypothesis that LRP1 is responsible for mediating the cellular uptake of monomeric tau, the endocytosis of $^{125}$I-labeled tau in WT Chinese hamster ovary (CHO) cells and in CHO 13-5-1 cells, which are deficient in LRP1, was examined (FitzGerald et al., *J. Cell Biol.*, (1995), 129). The results (FIG. 1b) reveal that while both cell types bind $^{125}$I-labeled tau on the cell surface, the cellular uptake of $^{125}$I-labeled tau was significantly reduced in CHO cells lacking LRP1. The contribution of LRP1 to cellular-mediated uptake of tau was further confirmed by demonstrating that RAP prevented the uptake of tau in WT CHO cells.

The time course of $^{125}$I-tau internalization in CHO WT and 13-5-1 cells reveal that both RAP and heparin reduce the amount of $^{125}$I-tau bound to the cell surface and internalized in CHO-WT cells, but had no effect on surface binding and internalization of $^{125}$I-labeled tau in CHO 13-5-1 cells (FIG. 1c). The fact that CHO 13-5-1 cells appear to internalize small amounts of $^{125}$I-labeled tau that is not inhibited by either RAP or heparin confirm the existence of an LRP1-independent pathway for tau internalization.

Previous studies have revealed that heparan sulfate proteoglycans regulate the cellular uptake of tau (Storck et al. *J. Clin. Invest.*, (2016), 126, 123-136; Rauch et al., *Sci. Rep.*, (2018), 8, 1-10; Stopschinski et al., *J. Biol. Chem.*, (2018), 293, 10826-10840). Thus, we also examined the cellular uptake of $^{125}$I-labeled tau in CHO cells deficient in xylosyltransferase lacking heparan sulfate proteoglycan (HSPG) biosynthesis and compared this to the extent of $^{125}$I-labeled tau internalized in WT and LRP1 deficient CHO cells (Esko et al., *Proc. Natl. Acad. Sci. USA*, (1985), 82, 3197-3201).

The results of this experiment (FIG. 1d) reveal no significant difference in surface binding of tau to HSPG-deficient CHO cells (K1 cells), but do show a significant reduction in the amount $^{125}$I-tau internalized when compared to WT CHO cells. These results reveal that glycosaminoglycans participate in the LRP1-mediated uptake of tau, similar to what one of the present inventors observed for LRP1-mediated VLDL uptake induced by lipoprotein lipase (Chappell et al., *J. Biol. Chem.*, (1994), 269). This occurs because proteoglycan binding sites on cell surfaces have much higher capacity but weaker affinity than LRP1, which results in the concentration of ligands on the cell surface that are then available for LRP1 binding and rapidly internalized.

Figure 2:
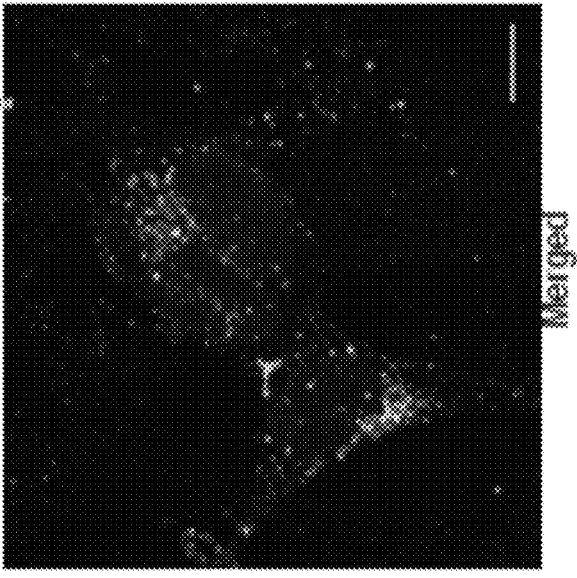
FIG. 2. Functional LRP1 colocalizes with tau in human neuroblastoma cells. Human neuroblastoma cells (SH-SY5Y) cells were grown on 8-chamber microscope slides until sub-confluent. The cells were serum starved by incubating with DMEM/F12 for 1 hour prior to experiment. The cells were then incubated at 37° C. for 2 hours with monoclonal antibody 5A6 conjugated with Alexa Fluor® 488 to label the endocytic pool of LRP1. After the cells were washed to remove unbound antibody, and they were incubated with 20 nM tau conjugated with Alexa Fluor®594 incubated at 37° C. for 2 hours. Fixed and permeabilized cells were then mounted using VECTASHIELD® mounting medium with DAPI. Colocalization of functional LRP1 and tau is displayed on merged panel. The scale bar is 10 μm.
Figure 2:
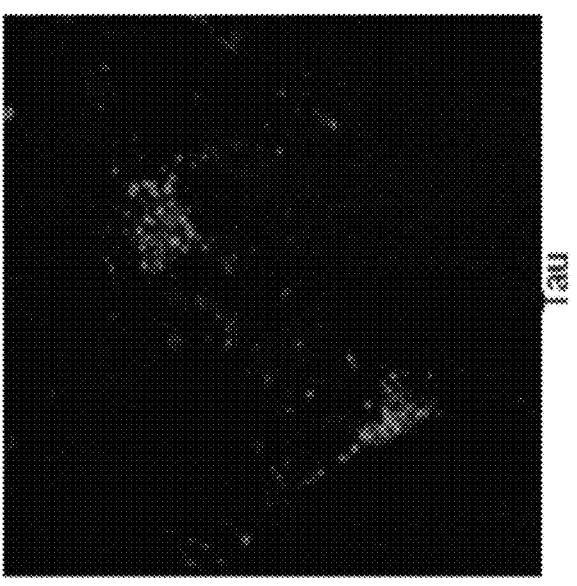
Figure 2:
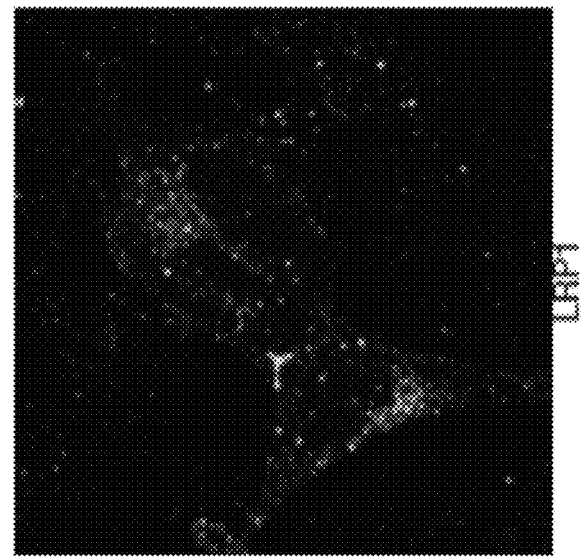

Next, the internalization of tau in the neuroblastoma cell line SH-SY5Y was examined, employing immunofluorescence with the goal of determining whether tau colocalizes with LRP1 during endocytosis. In these experiments, functional LRP1 was labeled with a monoclonal antibody that recognizes the LRP1 light chain and does not dissociate from the receptor during endosomal trafficking and receptor recycling (Muratoglu et al., *J. Biol. Chem.*, (2010), 285, 14308-14317). The live cells were then incubated with fluorescently labeled tau. The results demonstrate co-localization of LRP1 and tau within endosomal compartments (FIG. 2).

Tau binds to purified LRP1 with high affinity.

Figure 3:
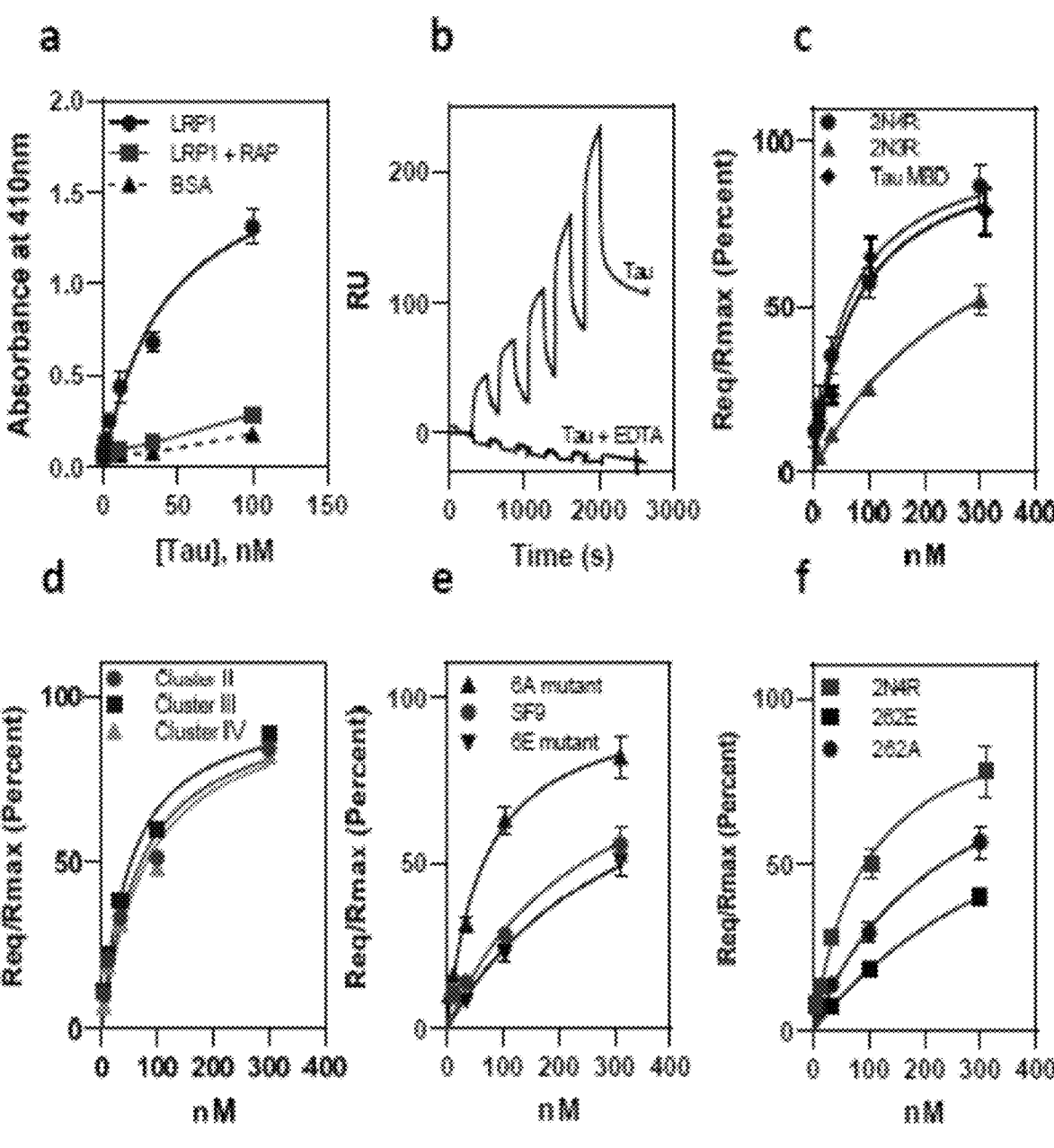
FIG. 3. Phosphorylated forms of tau bind full-length human LRP1 with weakened affinity. a) Microtiter wells were coated with 4 μg/mL purified human LRP1 or with BSA (triangles) and incubated with increasing concentrations of human recombinant tau (2N4R) (circles) in the absence or presence of 1 μM RAP. Tau binding was detected with anti-tau antibody. The mean±S.E. of increasing concentrations of optical densities (410 nm) in three independent replicates is shown. b) Binding of increasing concentrations of monomeric tau (3.8, 11.5, 34.4, 103.3, 310 nM nmol/L) to full-length human LRP1 immobilized on the surface of a surface plasmon resonance (SPR) sensor chip in the presence of 1 mM Ca$^{2+}$ or 3 mmol/L EDTA in a single cycle kinetic experiment. c) The binding of tau isoforms 2N4R, 2N3R, and tau MBD to full-length human LRP1 were measured by SPR. 2N4R, K$_D$=60±8 nM; 2N3R, K$_D$=278±8 nM; and tau MBD, K$_D$=73±18 nM. d) Binding of increasing concentrations of monomeric tau (3.7, 11.1, 33.3, 100, 300 nmol/L) to LRP1 clusters II, III, or IV immobilized on the surface of a SPR sensor chip in the presence of 1 mM Ca$^{2+}$. Cluster II, K$_D$=69±25; cluster III, K$_D$=52±14; cluster IV, K$_D$=81±29 nM. e) The binding of tau produced by Sf9 cells along with two mutant forms of tau to full-length human LRP1 were measured by SPR; 6A, (T181, S199, S202, S396, S400 and S404 are all converted to alanine), 6E, in which all of these residues are converted to glutamic acid. Sf9, K$_D$=243±17 nM; 6A K$_D$=65±8 nM; 6E K$_D$=494±154 nM. f) The binding of tau mutants 262A (serine 262 residue converted to alanine), and 262E (serine 262 residue converted to glutamic acid) to full-length human LRP1 were measured by SPR. S262A, $K_D$=230±49; S262E, $K_D$=450±90 nM. All SPR experiments were performed in triplicate. Response units at equilibrium (Req) were determined from fitting the association data (response units, RU) to a pseudo-first order process, and normalized to Rmax and expressed as a percentage. These values were then plotted against total ligand concentration and fit to a binding isotherm using nonlinear regression analysis in GraphPad Prism 8.

To extend our cell-based results, the binding of tau to purified LRP1 was investigated. Initial experiments utilized an ELISA in which purified LRP1 was immobilized on the surface of microtiter plates, and the ability of increasing concentrations of tau to bind to the LRP1 coated wells was measured. As a control, the binding of tau to LRP1 in the presence of RAP and to BSA-coated wells was also measured. The results of this experiment are shown in FIG. 3a and confirm RAP-dependent binding of tau to LRP1. Further, the results reveal that tau selectively binds to LRP1-coated wells, but not to BSA-coated wells. To quantify the interaction of tau with LRP1, surface plasmon resonance measurements in which increasing concentrations of tau were introduced over an LRP1-coupled SPR chip were utilized in a single cycle kinetic experiment (FIG. 3b). The specificity of the interaction was confirmed by demonstrating that the binding of tau to the LRP1-coated chip was ablated in the presence of EDTA, which chelates the essential $Ca^{2+}$ ions necessary to stabilize the LDL ligand binding repeats, which are critical for ligand binding by this class of receptors. To determine the $K_D$ of this interaction, the individual data was fitted to a pseudo-first-order process to obtain values of Req for each concentration of tau, and then the Req values were plotted as function of total concentration of tau (FIG. 3c). Nonlinear regression analysis of the plot revealed a $K_D$ value of 60±8 nM for the 2N4R tau isoform, a value comparable to other LRP1 ligands. Tau contains two major domains: an N-terminal "projection" domain containing the N1 and N2 regions and the C-terminal microtubule binding domain containing four highly conserved repeat regions, R1-R4, which binds to microtubules (Nizynski et al., *Protein Sci.*, (2017), 26, 2126-2150). Interestingly, the 2N3R isoform of tau, lacking the second microtubule binding repeat (R2) encoded by exon 10, bound to LRP1 with considerably weaker affinity ($K_D$=278±55 nM, FIG. 3c) suggesting that the R2 domain of tau contributes to the interaction of tau with LRP1. The interaction of the microtubule binding domain (R1-R4, leu243-glu372) with LRP1 was quantified using SPR measurements, and the results of these experiments reveal that this region of tau binds to LRP1 with an affinity similar to the intact molecule ($K_D$=73±18 nM) (FIG. 3c).

The ligand binding regions of LRP1 are mainly localized to clusters of LDLa repeats, termed clusters I, II, III and IV. Of these clusters, most ligands bind to clusters II or IV (Neels, et al. J. Biol. Chem., (1999), 274, 31305-31311). To determine which region of LRP1 is involved in tau binding, the binding of tau to clusters II, III and IV immobilized on SPR chips was investigated. The results of a single cycle kinetic experiment confirm that tau readily binds to clusters II, III and IV with $K_D$ values of 69±25, 52±14 and 81±29 nM, respectively (FIG. 3d). The binding of tau to all three clusters of LRP1 with similar affinity is unusual, and may indicate some cooperativity in the binding of tau to cellular LRP1 that is not detectable on immobilized LRP1.
Phosphorylation of tau reduces its affinity for LRP1.

The C-terminal microtubule binding domain of tau contains multiple serine, threonine and tyrosine phosphorylation sites which has been extensively studied as phosphorylation is a common post-translational modification of tau (Bramblett et al., Neuron, (1993), 10, 1089-1099; Mandelkow et al., Neurobiol. Aging, (1995), 16, 355-362; Hanger et al., J. Biol. Chem., (2007), 282, 23645-23654). Phosphorylated forms of tau are detected in neurofibrillary tangles which has connected these forms of tau to cognitive decline in AD as well as frontotemporal dementia (Grundke-Iqbal et al., Proc. Natl. Acad. Sci. U.S.A, (1986), 83, 44913-44917; Ihara et al., Biochem., (1986), 99, 1807-1810; Iqbal et al. Proc. Natl. Acad. Sci. U.S.A, (1989), 86, 5646-5650). In addition, tau phosphorylation at specific residues has differential effects on its function, regulates its subcellular localization and reduces its affinity for microtubules (Pooler et al., Neurobiol. Aging, (2012), 33, 431.e27-431.e38; Sultan et al., J. Biol. Chem., (2011), 286, 4566-4575; Tang et al., Biochim. Biophys. Acta—Mol. Cell Res., (2015), 1853, 1646-1657; Biernat et al., Neuron, (1993), 11, 153-163; Jameson et al., Biochemistry, (1980), 19, 2472-2479). Therefore, the hypothesis that phosphorylation of tau might alter its binding to LRP1 was tested by examining the binding of tau produced by Sf9 cells, which secrete well characterized hyperphosphorylated forms of tau (Tepper et al., J. Biol. Chem., (2014), 289, 34389-34407). These studies reveal that hyperphosphorylated tau produced by Sf9 cells bound LRP1 with a 4-fold weaker affinity ($K_D$=243±17 nM) (FIG. 3e). The binding of two mutant forms of tau to LRP1 was also examined: mutant 6A, in which T181, S199, S202, S396, S400 and S404 are all converted to alanine, and mutant, 6E, in which all of these residues are converted to the phospho-mimic glutamic acid. These residues have been found to be phosphorylated in both normal and AD brains (Šimić et al., Biomolecules, (2016), 6, 2-28). The results reveal that while the 6A mutant binds to LRP1 with a $K_D$ value similar to that of WT tau ($K_D$=65±4 nM), and the 6E mutant binds to LRP1 with 5-fold weaker affinity ($K_D$=321±17 nM) (FIG. 3e).

Phosphorylation of tau at serine 262 is of interest, as this residue is located within the tau microtubule binding domain and its phosphorylation strongly reduces the binding of tau to microtubules (Biernat et al., Neuron, (1993), 11, 153-163). Further, S262 is a critical modulator of tau toxicity in a transgenic Drosophila model of AD (Iijima et al., Hum. Mol. Genet., (2010), 19, 2947-2957). Next, the binding of S262A and S262E tau mutants to LRP1 was measured, and the results reveal that both mutants bind poorly to LRP1, with $K_D$ values of 230±49 and 450±90 nM, respectively (FIG. 3f). The weaker affinity of the S262A mutant for LRP1 is unexpected and suggests an important role for this residue in the interaction of tau with LRP1.

Together, the results of the present studies reveal that phosphorylated forms of tau bind to LRP1 with significantly lower affinity. Since phosphorylation of tau is generally associated with increased tau pathology, reduced binding of phosphorylated tau to LRP1 suggests that the LRP1-mediated pathway is less efficient in mediating the endocytosis of these pathological forms of tau.

ApoE4 blocks the LRP1-mediated internalization of tau.

Figure 4:
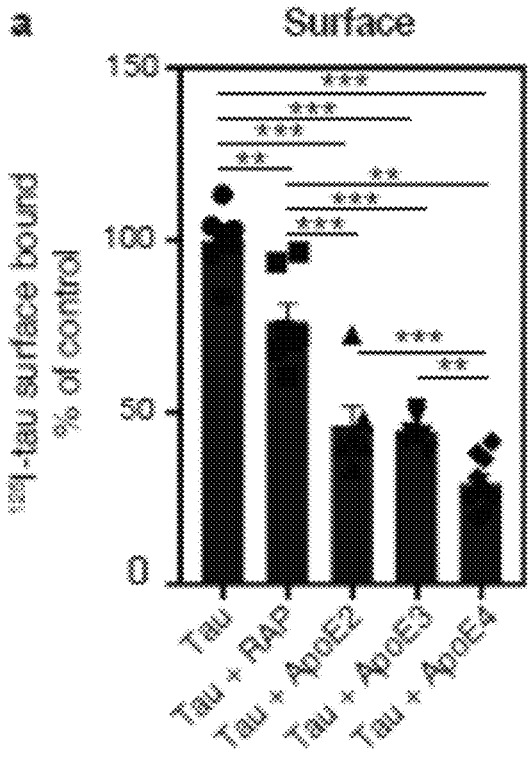
FIG. 4. ApoE inhibits surface binding and internalization of tau by LRP1. WT CHO cells were cultured overnight in the presence of 10 µg/mL apoE2, apoE3, or apoE4. The cells then incubated with 20 nM $^{125}$I-tau in the absence or presence of 10 µg/mL apoE isoforms at 37° C. for 2 hours. The amounts of surface bound (a) and internalized (b) $^{125}$I-tau were quantified. Statistical analysis was performed using one-way ANOVA and Tukey post-hoc test (*P<0.05, P<0.0006, and *P<0.0001).
Figure 4:
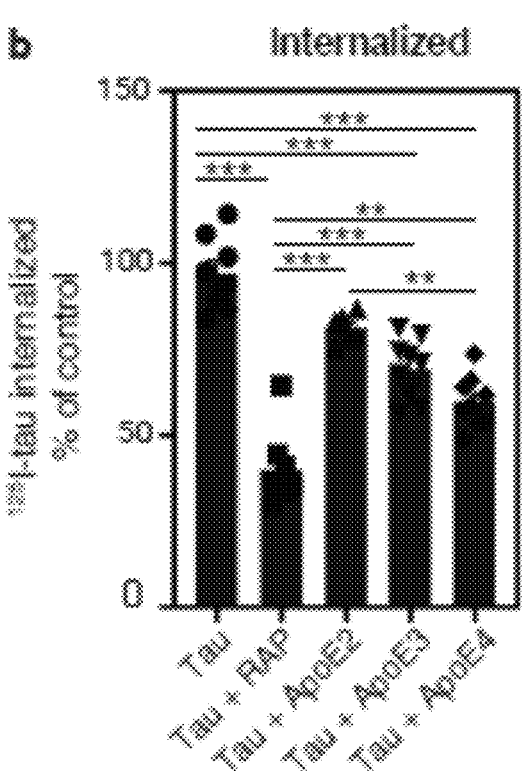
Figure 5:
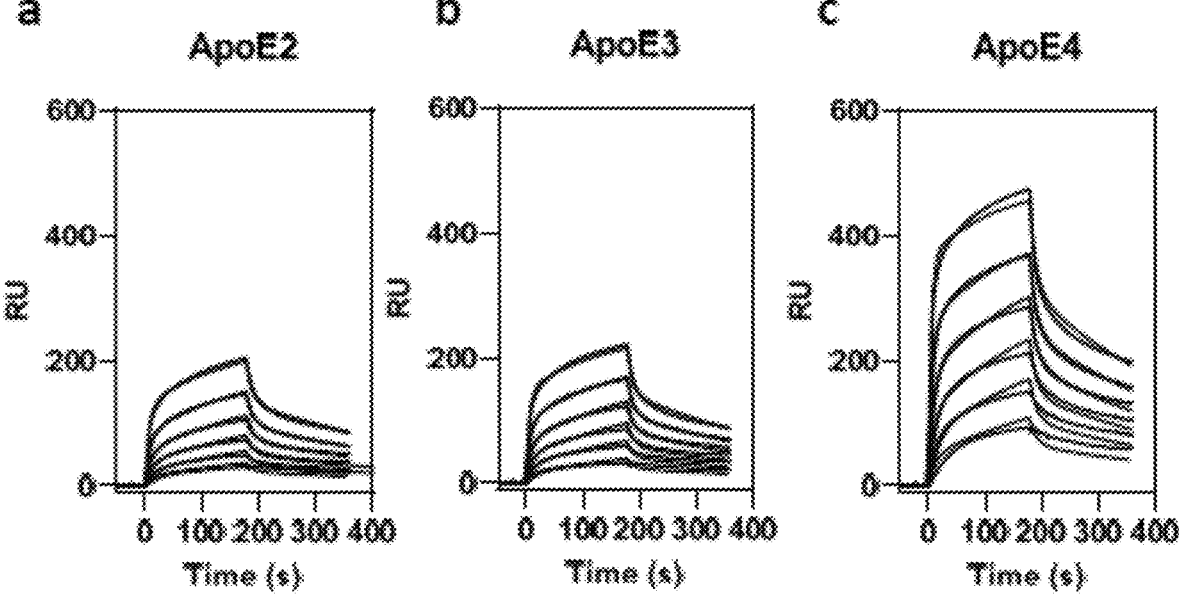
FIG. 5. Binding of apoE isoforms to LRP1 analyzed by SPR. Increasing concentrations (52, 104, 208, 417, 834, 1668 nM) of apoE2 (a), apoE3 (b) or apoE4 (c) were flowed over an LRP1-coupled SPR surface. Data were analyzed by fitting to a bivalent model (blue curves) which yielded $K_D$ values of 416, 363, and 191 nM for apoE2, apoE3 and apoE4, respectively.

A strong risk factor for late-onset AD is apolipoprotein E (APOE), with the ε4 allele representing a risk factor and the ε2 allele being protective (Corder et al., Adv. Sci., (2008), 261, 921-923; Strittmatter et al., Proc. Natl. Acad. Sci. U.S.A, (1993), 90, 1977-1981). Mouse models have shown that the ApoE ε4 allele impacts Aβ metabolism, and exacerbates tau-mediated neurodegeneration (Verghese et al., Proc. Natl. Acad. Sci., (2013), 110, E1807-E1816; Castellano et al., Sci. Transl. Med., (2011), 3; Shi et al., Nature, (2017), 549, 523-527). LRP1 is a major apoE receptor expressed in the brain, and the present inventors hypothesized that apoE may modulate LRP1-mediated tau catabolism. To test this hypothesis, the effect of apoE2, apoE3 and apoE4 on the LRP1-mediated internalization of tau was examined. In our experiments, apoE2, apoE3 or apoE4 were preincubated overnight with WT CHO cells, and, following incubation, the uptake of $^{125}$I-labeled tau was measured. The results of this experiment reveal that all apoE isoforms block the surface binding and significantly reduce the amount of $^{125}$I-labeled tau that is internalized (FIG. 4). Of interest, apoE4 is more effective in inhibiting LRP1-mediated tau internalization than the apoE2 isoform. The effect of apoE isoforms on LRP1-mediated tau catabolism correlates with the affinity of these isoforms for LRP1, as quantified by SPR experiments (Extended data, FIG. 1, Table I), with the affinity for LRP1 found to be in the order apoE4>apoE3>apoE2. While the effect of apoE could be direct competition, it is interesting to highlight the finding that apoE4 traps LRP1 within intracellular compartments reducing surface levels and selectively impairs the recycling and surface expression of apoER2, another LDL receptor family member (Prasad et al., Proc. Natl. Acad. Sci. U.S.A, (2018), 115, E6640-E6649; Chen et al., Proc. Natl. Acad. Sci. U.S.A, (2010), 107, 12011-12016).

The present inventors hypothesize that the ability of ApoE4 to inhibit the LRP1-mediated uptake of tau may disrupt the normal physiological process of tau catabolism, leading to tau uptake by other receptors and exacerbating the progression of tau-mediated cognitive loss. This is likely to be especially true for hyperphosphorylated forms of tau that only bind weakly to LRP1. In support of this hypothesis, P301S tau transgenic mice were generated on an ApoE knock-out background or on human ApoE2, ApoE3 or ApoE4 backgrounds and it is noted that the P301S/E4 mice exacerbate tau-mediated neurodegeneration compared to P301S/E3, P301S/E2, or P301S/KO mice (Shi et al., Nature, (2017), 549, 523-527). At three months of age, the P301S/E4 mice contained significantly higher tau levels in the brain and displayed a greater extent of somatodendritic tau distribution.

In further support of the hypothesis that apoE disrupts normal LRP1-mediated tau catabolism is the recent identification of a patient who inherited an autosomal-dominant E280A mutation in presenilin 1 (PSEN1) and remained disease free due to homozygosity of APOE3ch gene variant (Arboleda-Velasquez et al., Nat. Med., (2019), 25). Interestingly, the study concluded that the APOE3ch homozygote conferred resistance to the clinical onset of AD by limiting tau pathology even in the face of high amyloid-β plaque burden (Arboleda-Velasquez et al., *Nat. Med.*, (2019), 25). This mutant of ApoE is impaired in its ability to bind to LDL receptor family members, and the present inventors hypothesize that the protective role of ApoE3ch results from its inability to inhibit LRP1-mediated tau catabolism, resulting in a switch to a second receptor mediated process that bypasses lysosomal degradation (Lalazar al., *J. Biol. Chem.*, (1988), 263, 3542-3545).

In summary, these results demonstrate that LRP1 is a central receptor that regulates trafficking and metabolism of several important molecules linked to AD which include APP and β-amyloid, tau, and apoE (Holtzman et al., *Cold Spring Harb. Perspect. Med.*, (2012), 2, 1-24; Hyman et al., Science (80-), (1984), 225, 1168-1170; Serrano-Pozo et al., *J. Neuropathol. Exp. Neurol.*, (2013), 72, 1182-1192; Medina et al., *Cell. Neurosci.* (2014) 8, 1-7; Wegmann et al., *Sci. Adv.*, (2019), 5; Beisiegel al., *Nature*, (1989), 341, 162-164; Kowal al., *Proc. Natl. Acad. Sci. U.S.A*, (1989), 86, 5810-5814). This positions LRP1 as an unprecedented molecular point of convergence for the pathological hallmarks of AD, and an understanding the individual pathways of each molecule and how they interconnect to LRP1 is key to the development of potential therapeutic intervention in this disease.

Example 2. Tau Binds the Receptor SorLA

Figure 6:
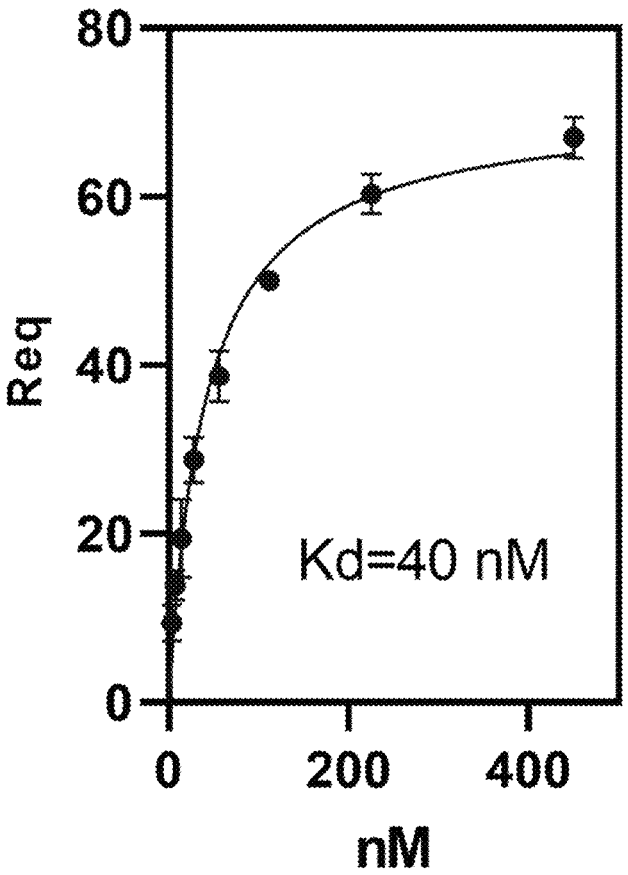
FIG. 6. Binding of tau to SorLA by SPR. This data was collected from a tau fragment immobilized on a SPR chip.

Experiments examining the potential of the SorLA receptor to bind with and mediate the uptake of tau by cells were conducted. A fragment of SorLA that is commercially available and comprises residues 82-181 was immobilized on an SPR chip, and the binding of tau to the SorLA receptor was examined by injecting increasing concentrations of tau over the surface of the immobilized SorLA. Binding strength was measured, and a $K_D$ value of 40 nM was found (FIG. 6).

Figure 7:
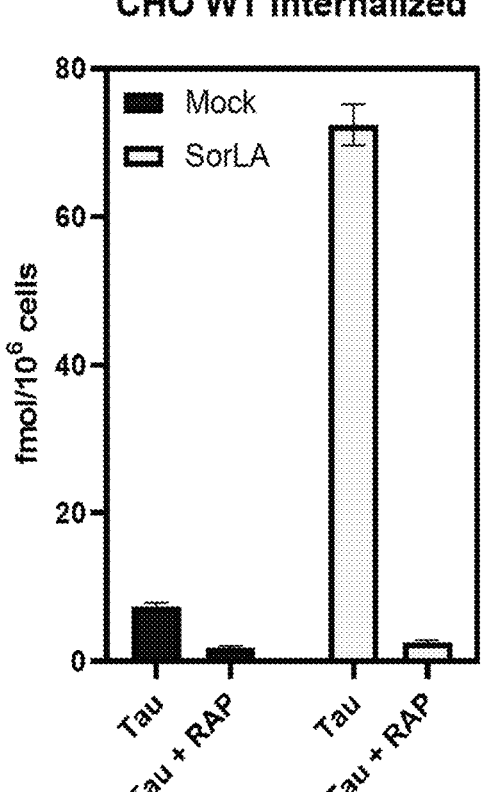
FIG. 7. Internalization of $^{125}$I-labeled tau in (A) CHO WT (A) and (B) CHO 13-5-1 (LRP1 deficient) cells. Tau was incubated with the cells for 2 h and the amount of internalized radioactivity was quantified.
Figure 7:
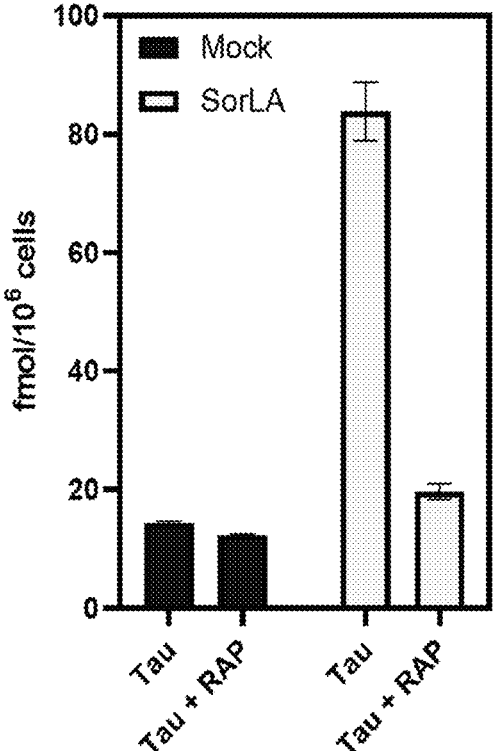

Example 3. Transfection of Cells with SorLA Results in Increased Tau Internalization LRP1 expressing CHO cells and LRP1-deficient CHO cells (13-5-1) were transfected with SorLA receptor protein, and these cells were examined to determine the extent of internalization of $^{125}$I-labeled tau that occurred after 2 h of incubation. The results of this experiment revealed that transfection of either cell with tau resulted in a substantial increase in tau internalization (FIG. 7).

These results indicate that SorLA can substitute for LRP1 in supporting the internalization of tau into mammalian cells.

Example 4. LRP1 Promotes Tau Seeding in Cells

Seeding Assay

Figure 8:
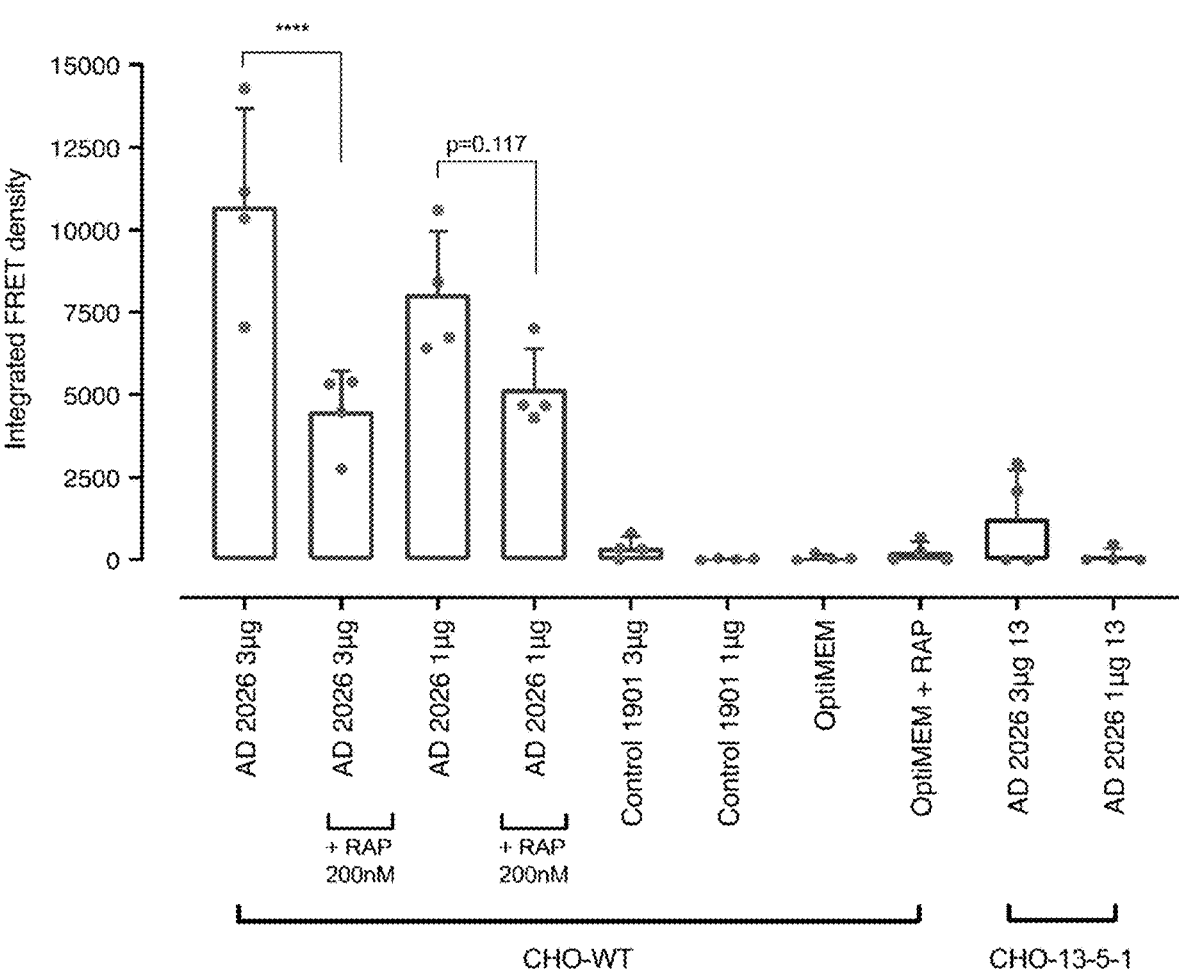
FIG. 8. 200 nM RAP was mixed with the brain lysate immediately before incubation with the cells. When lipofectamine was added with the lysate, both CHO-WT and 13-5-1 had high amount of FRET signal detected (positive control, >10× stronger signal).
Figure 9:
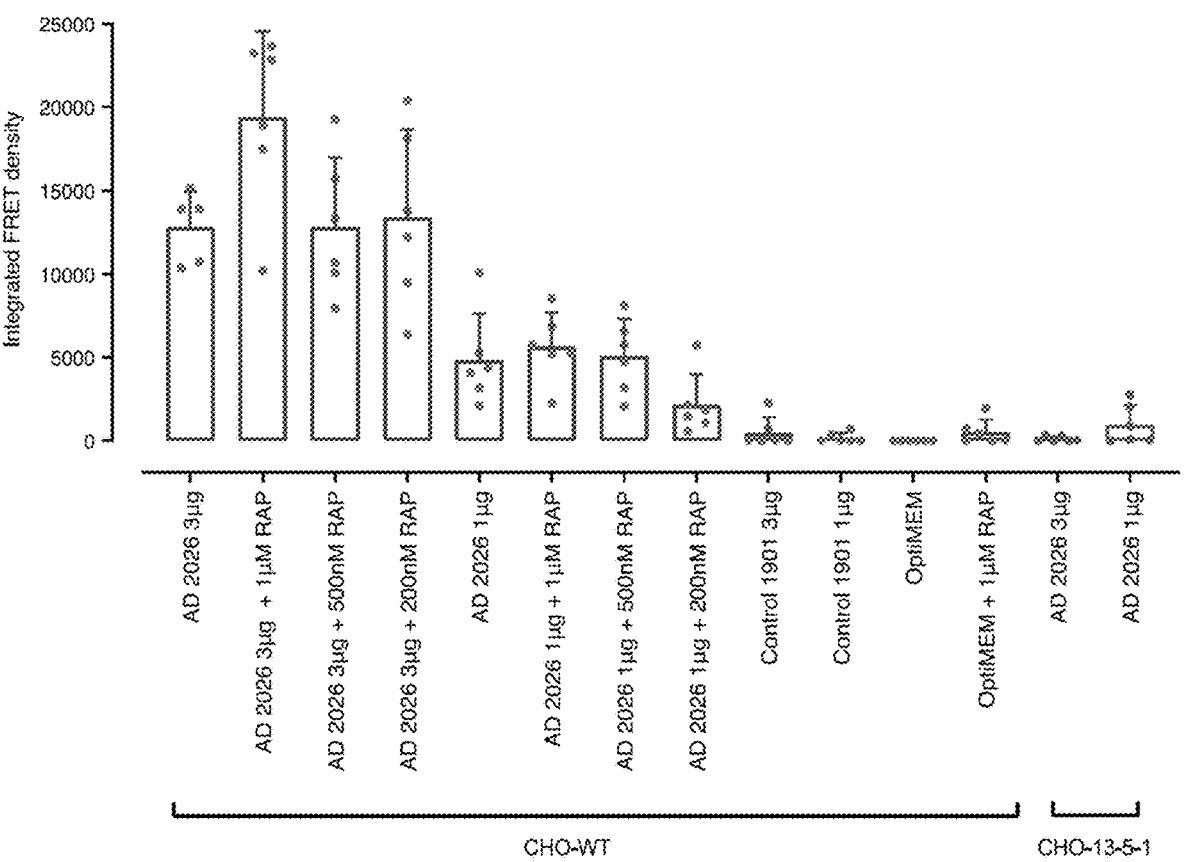
FIG. 9. Three concentrations (1 µM, 500 nM and 200 nM) of RAP were tested. RAP was preincubated on the cells for 1 hour before adding brain lysate diluted in OptiMEM+RAP.

The tau seeding in vitro assay that had been previously described was adapted for the present study (Holmes el al., *Proc. Natl. Acad. Sci. U.S.A*, (2014), 111, E4376-4385, 10.1073/pnas.1411649111; Furman el al., *J Vis Exp*, (2015), e53205, 10.3791/53205). CHO WT and CHO 13-5-1 cells were plated in Costar Black (Corning), clear bottom 96-well plates at 16,000 cells/well. The next day, cells were transduced with a pcDNA3 plasmid containing a construct that encoded the 344-378 residues of human P301L mutant tau fused to mTurquoise2, a self cleaving 2A peptide, and 344-378 of human P301L mutant tau fused to Neon Green. Cells were transfected with 100 ng DNA/well diluted in OptiMEM, using lipofectamine 3000 (final volume of 50 μl/well). The following day, transfection medium was replaced with 50 μl of OptiMEM containing 1-3 μg of human brain homogenate in the presence/absence of RAP. For positive controls, 1% lipofectamine 2000 was added to the wells. Each condition was tested at least in quadruplicate. Cells were incubated with lysates for 24 to 28 hours. Cells were then collected using trypsin and transferred into 96-well U-bottom plates (Corning) using 10% FBS culture medium to neutralize trypsin. Cells were pelleted at 1200×g for 10 minutes, resuspended in cold 2% paraformaldehyde for 10 minutes, pelleted at 1200×g and resuspended in 200 μl of PBS. Samples were ran on the MACSQuant VYB (Miltenyi) flow cytometer for the quantification of Turquoise fluorescence and Forster resonance energy transfer (FRET). Tau seeding was quantified by multiplying the percent of FRET-positive cells by the median fluorescence intensity of those cells, as described previously (DeVos et al., *Front Neurosci*, (2018), 12, 267, 10.3389/fnins.2018.00267). 40,000 cells per well were analyzed. Data was analyzed using FlowJo software. Results are shown in FIGS. 8 and 9.

Methods

Tau Seeding FRET Biosensor Assay

Human Brain Homogenates

Brain samples from one AD Braak VI and one healthy control brain from the Massachusetts Alzheimer's Disease Research Center Brain Bank were used in this study. Briefly, 100 mg of frontal cortex tissue (Brodman area 8/9) were thawed and homogenized in 500 μl of PBS with protease inhibitor (Roche) by 30 up and down strokes in a glass Dounce homogenizer. The homogenate was centrifuged at 10,000×g for 10 min at 4° C. The supernatant was aliquoted and a bicinchoninic acid assay (BCA, Thermo Scientific Pierce) was performed according to manufacturer's instructions to quantify total protein concentration.

Example 5. SORLA Regulates the Cellular Trafficking of Tau and Supports Tau Seeding The interneuron transfer of pathological forms of tau has been proposed as a mechanism of Alzheimer disease (AD) progression, as the accumulation of misfolded tau aggregates initiates in the entorhinal cortex and spreads across connected neural pathways (Hyman et al., *Science*, (1984), (80-) 225: 1168-1170; Serrano-Pozo et al., *J Neuropathol Exp Neurol*, (2013), 72: 1182-1192; Braak H & Braak E, *Acta Neuropathol*, (1991) 82: 239-259; Polydoro et al., *J Neurosci*, (2013), 33: 13300-13311; De Calignon et al., *Neuron*, (2012), 73: 685-697; Liu et al., *PLoS One*, (2012), 7: e31302; Harris et al., *PLoS One*, (2012), 7: e45881). How proteopathic seed-competent tau is taken up and delivered to the cytoplasm of the recipient cells remain a central question in understanding this process, but likely involves cellular receptors that internalize tau (Takeda et al., *Nat Commun*, (2015) 6: 8490; Dujardin et al., *Nat Med*, (2020), 26: 1256-1263). Recent studies have demonstrated that the LDL receptor-related protein 1 (LRP1) is a key receptor in tau uptake across neural systems (Rauch et al., *Nature*, (2020), 580: 381-385; Cooper et al., *J Biol Chem*, (2021), 296: 100715). Interestingly, in addition to confirming the role of LRP1 in tau uptake, we observed residual uptake of $^{125}$I-labeled tau in cells genetically deficient in LRP1, confirming the existence of additional receptors capable of mediating tau uptake (Cooper et al., *J Biol Chem*, (2021), 296: 100715). The studies of Rauch et al. eliminated several other LDL-receptor family members as candidate receptors for tau, including LRP1B, LRP2, LRP5, LRP8, LDLR and VLDLR (Rauch et al., *Nature*, (2020), 580: 381-385).

The present inventors hypothesized that sortilin-related receptor 1 (SORLA, also known as SORL1 or LR11), itself a molecule that is genetically linked to AD, might participate in tau trafficking (Holstege et al., *Eur J Hum Genet*, (2017), 25: 973-981; Pottier et al., *Mol Psychiatry*, (2012), 17: 875-879; Rogaeva et al., *Nat Genet*, (2007), 39: 168-177).

It is shown herein that SORLA is an endocytic and intracellular sorting receptor that recognizes numerous ligands, regulates APP trafficking, and is genetically associated with AD. Here, we investigated the hypothesis that SORLA functions as a receptor that modulates tau trafficking in cells and can promote tau seeding. Our data reveal that the VPS10P domain of SORLA binds tightly to tau, and that overexpression of SORLA in WT and LRP1 deficient CHO cells increases tau uptake. Further, like LRP1, SORLA is capable of mediating tau seeding resulting in intracellular tau aggregation when exposed to pathogenic forms of tau.

To investigate the hypothesis that SORLA is involved in the cellular trafficking of tau, human SORLA was expressed in cell lines deficient in LRP1 or SORLA was knocked down using siRNA in H4 neuroglioma cells and then the cellular uptake was examined of tau and potential of pathogenic forms of tau to promote tau seeding. The studies reveal that SORLA modulates tau trafficking, endocytosis, degradation, and release into the cytoplasm of seed competent species. Surface plasmon resonance experiments confirm high-affinthat both CHO WT (FIG. 10*b*) and CHO 13-5-1 cells (FIG. 10*c*) expressing SORLA bound more $^{125}$I-labeled tau on their cell surface and demonstrated a dramatic increase in the amount of tau internalized when compared to cells incubated with transfection reagent only ("mock"). Both the binding and internalization of tau was inhibited by receptor associated protein (RAP, FIG. 10*b,c*), which is known to bind tightly to SORLA and antagonize certain ligands from interacting with this receptor (Gliemann et al., *Biochem J*, (2004), 381: 203-212).

The VPS10P domain of SORLA binds tau with high affinity. To determine if SORLA is capable of directly binding tau, surface plasmon resonance (SPR) experiments were employed. In these experiments, the recombinant VPS10P domain of SORLA (residues 82-753) was coupled to an SPR chip and increasing concentrations of various forms of tau were flowed over the surface in a single cycle kinetic experiment. The data were quantified by fitting the kinetic titration to a 1:1 interaction model (FIG. 11*a*) or by an equilibrium fit of the individual data to a pseudo-first-order process to obtain values of Req for each concentration which were then plotted as a function of the total concentration of tau (FIG. 11*b-e*) (Karlsson et al., *Anal Biochem*, (2006), 349: 136-147). The kinetic and equilibrium data are summarized in Table I, along with the various forms of tau used.

TABLE I

Kinetic and equilibrium binding constants for the interaction of various forms of tau with the VPS10P domain of SORLA.

| Tau | Mutants | $k_a$ $(M^{-1}s^{-1})$ | $k_d$ $(s^{-1})$ | $^1K_D$ (nM) | $^2K_{D\ eq}$ (nM) |
|---|---|---|---|---|---|
| 2N4R | WT | $5.0 \pm 7.0 \times 10^7$ | $4.1 \pm 5.5 \times 10^{-1}$ | $15 \pm 9$ | $17 \pm 1$ |
| 0N3R | Tau lacking N1 & N2 | $1.3 \pm 0.3 \times 10^5$ | $1.3 \pm 0.4 \times 10^{-2}$ | $10 \pm 1$ | $5 \pm 1$ |
| 2N3R | Tau lacking R2 | $1.9 \pm 0.4 \times 10^6$ | $1.1 \pm 0.6 \times 10^{-2}$ | $18 \pm 3$ | $11 \pm 2$ |
| MBD | L243-E372 | $2.8 \pm 0.5 \times 10^5$ | $2.4 \pm 0.6 \times 10^{-3}$ | $93 \pm 40$ | $341 \pm 14$ |
| 2N4R SF9 | Tau produced in SF9 cells | $8.5 \pm 2.5 \times 10^4$ | $6.1 \pm 2.9 \times 10^{-3}$ | $78 \pm 13$ | $95 \pm 28$ |
| 2N4R 6A | T181/S199/ S202/S396/ S400/S404 to A | $1.1 \pm 0.5 \times 10^6$ | $1.1 \pm 0.7 \times 10^{-2}$ | $10 \pm 1$ | $9 \pm 2$ |
| 2N4R 6E | T181/S199/ S202/S396/ S400/S404 to E | $8.3 \pm 1.8 \times 10^5$ | $1.5 \pm 0.5 \times 10^{-2}$ | $1.8 \pm 3$ | $11 \pm 2$ |
| 2N4R 3xKQ | K311/317/321 to A | $1.5 \pm 0.6 \times 10^6$ | $2.0 \pm 0.6 \times 10^{-2}$ | $14 \pm 2$ | $17 \pm 12$ |
| 2N4R 9xKQ | K311/317/321/ 340/343/347/ 353/369/375 to E | $7.0 \pm 2.0 \times 10^5$ | $1.5 \pm 0.3 \times 10^{-2}$ | $22 \pm 6$ | $32 \pm 2$ |

Figure 10:
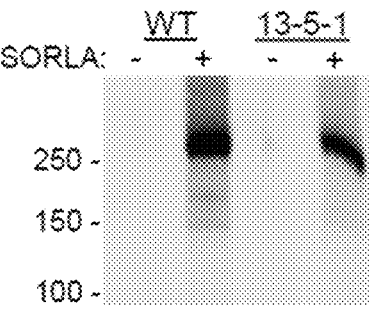
FIG. 10. SORL1 mediates the internalization of tau. (a) WT and LRP1-deficient CHO 13-5-1 cells were transfected with SORL1 plasmid, and transfection efficiency was validated via immunoblot analysis. (b) WT and (c) LRP1-deficient CHO 13-5-1 cells transfected with SORL1 plasmid or empty vector "Mock" were incubated with 20 nM $^{125}$I-labelled tau±1 µM RAP for 2 hours. Surface levels and internalized tau was quantified. (Means±SEM, two-way ANOVA followed by Tukey multiple comparisons test).
Figure 10:
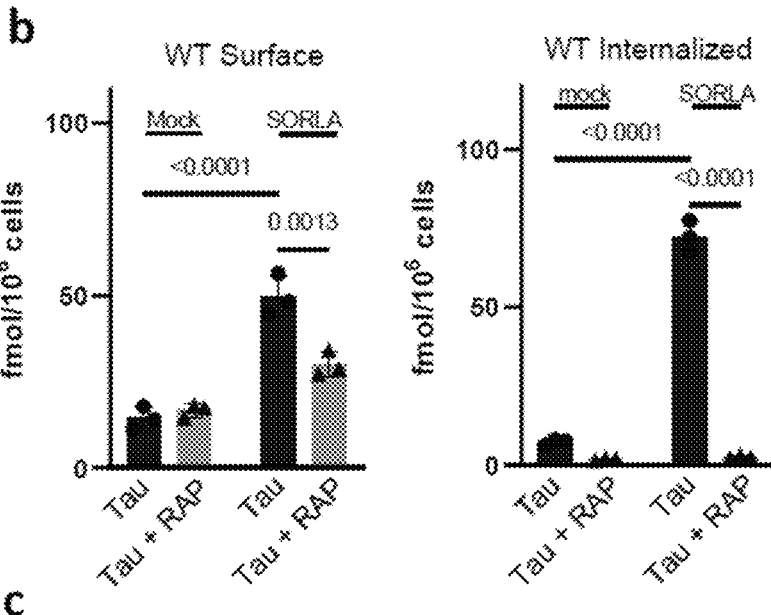
Figure 10:
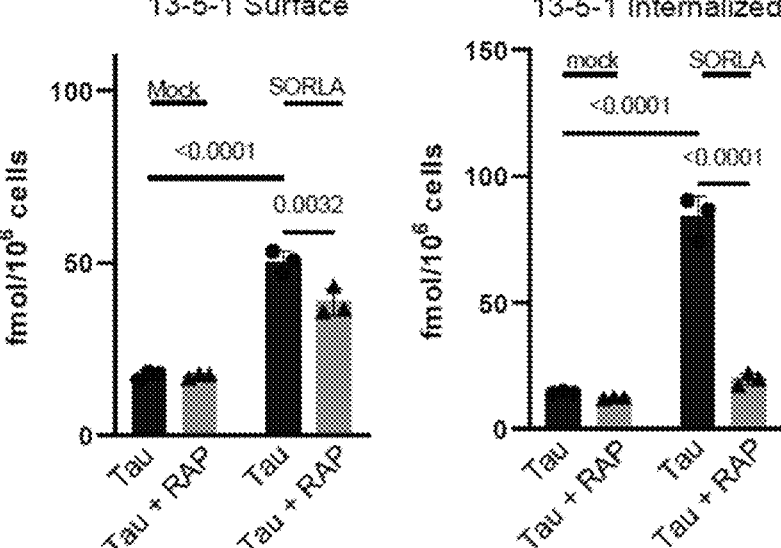
Figure 11:
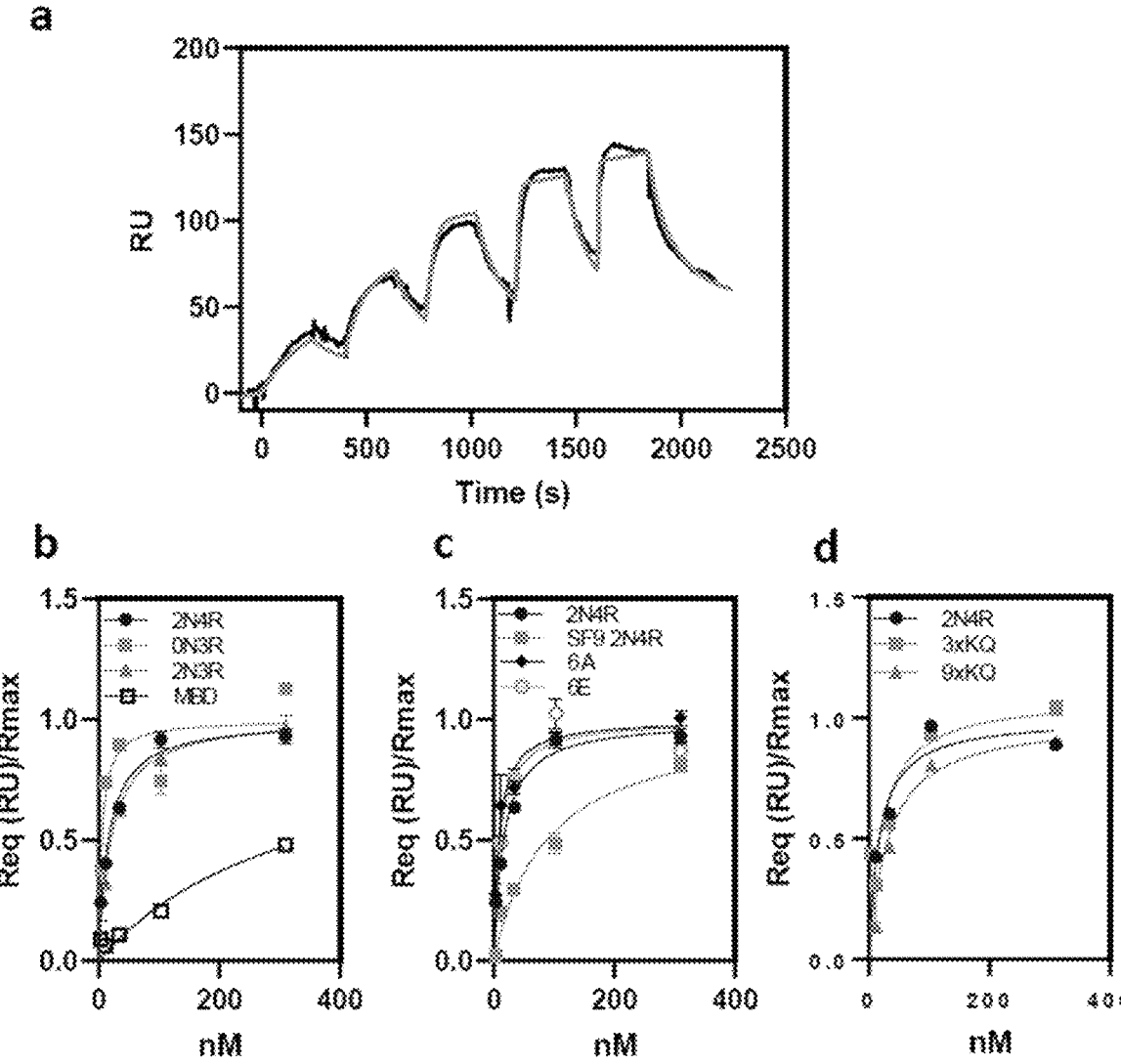
FIG. 11. Recombinant monomeric tau binds to VPS10P domain of SORLA. (a) Binding of increasing concentrations of recombinant 2N4R tau to SORL1 VPS10 domain coupled to a Biacore CM5 sensor chip in a single cycle kinetic experiment. Data were fit to a 1:1 binding model. (b) Binding of tau isoforms 2N4R, 0N3R, 2N3R and tau MBD to SORLA VPS10P domain assessed by SPR equilibrium analysis. (c) The binding of tau produced by Sf9 cells along with two mutant forms of tau to SORLA VPS10P domain was measured by SPR; 6A (T181, S199, S202, S396, S400, and S404 are all converted to alanine) and 6E, in which all these residues are converted to glutamic acid. (d) Binding of mutant forms of tau to SORLA VPS10P domain: 3XKQ in which lysine residues 311, 317, and 321 were converted to glutamine residues and 9XKQ tau in which lysine residues 311, 217, 321, 340, 343, 347, 353, 369, and 375 are all converted to glutamine residues. For all experiments, n=3 (biological replicates), (a) shows representative data, (b, c, d, and e) show means±SEM. MBD, microtubule-binding domain; SPR, surface plasmon resonance.

[1]The equilibrium dissociation constant $K_D$ was calculated front the kinetic parameters for a 1:1 fit
[2]$K_D$ eq was calculated from SPR equilibrium measurements, in which Req was determine by fitting the association data to a pseudo-first order process.

ity binding of tau to the SORLA VPS10 domain. Additionally, we find that the N1358S mutant of this receptor increases tau seeding, identifying for the first time a potential mechanism that connects this mutation in SORLA to Alzheimer's disease.
Results SORLA mediates the endocytosis of tau. To test the hypothesis that SORLA can bind tau and mediate its cellular uptake, WT Chinese hamster ovary (CHO) cells or LRP1-deficient CHO 13-5-1 cells, neither which express detectable levels of SORLA, were transfected with a plasmid containing a construct that encoded SORLA (FIG. 10*a*). The cells were incubated with $^{125}$I-labelled tau for 2 hours at 37° C., and the amount of $^{125}$I-labeled tau associated with the cell surface and internalized was quantified. The results revealed Binding experiments revealed that recombinant 2N4R tau bound tightly to this domain of SORLA with a $K_D$ value of 17±1 nM (FIG. 11*b*). Tau consists of an N-terminal "projection" domain that contains alternatively spliced regions denoted as "N1" and "N2" regions, along with a C-terminal microtubule binding domain (MBD) composed of four highly conserved repeat regions, "R1"-"R4" (Nizynski et al., *Protein Sci*, (2017), 26: 2126-2150). The MBD is the site of interaction for tau with microtubules, and also a primary site of interaction with LRP1 (Cooper et al., *J Biol Chem*, (2021), 296: 100715). To identify domains in tau responsible for its interaction with the SORLA VPS10P domain, we investigated the binding of ON3R (lacking the projection domain), 2N3R (lacking the second R domain and which has reduced affinity for LRP1), and the MBD (R1-R4, leu243- glu372) to the SORLA VPS10P domain, and obtained $K_D$ values of 5±1, 11±2, and 341±14 nM, respectively (FIG. 11$b$). These results reveal that, unlike LRP1, tau binding to SORLA VPS10 domain is not primarily through the MBD, and unlike LRP1, is not impacted by removal of the second R domain.

Tau is a highly post-translationally modified protein, containing multiple serine, threonine, and tyrosine phosphorylation sites that have been extensively studied and that are detected in tau aggregates in AD and other tauopathies. In our previous study, we found that hyperphosphorylation of tau reduces its affinity for LRP1 4-fold (Cooper et al., *J Biol Chem*, (2021), 296: 100715). To investigate if phosphorylation of tau impacts tau binding to SORLA VPS10 domain, we examined the binding of recombinant tau produced in Sf9 insect cells, which produce well-characterized hyperphosphorylated forms of tau (Mair et al., *Anal Chem*, (2016), 88: 3704-3714; Tepper et al., *J Biol Chem*, (2014), 289: 34389-34407). We found SF9 tau binds SORLA VPS10 with a $K_D$ of 95±28 nM (FIG. 11$c$). We also examined the binding of two mutant forms of tau to SORLA VPS10: mutant 6A, in which T181, 5199, 5202, 5396, 5400, and 5404 are all converted to alanine, and mutant 6E, in which all these residues are converted to the phosphomimetic glutamic acid. These specific residues have been found to be phosphorylated to a greater extent in AD brains, and we previously found the 6E mutant binds LRP1 with weaker affinity, while 6A binds LRP1 similar to WT tau (Šimić et al., *Biomolecules*, (2016), 6: 2-28; Cooper et al., *J Biol Chem*, (2021), 296: 100715). Our results reveal that the affinity of either mutant for the SORLA VPS10P domain is similar to that of the 2NR4 tau ($K_D$ 6A mutant=9±2 nM; $K_D$ 6 E mutant=11±2 nM) (FIG. 11$c$).

Lysine residues are important for the binding of tau to LRP1, and to further investigate tau-SORLA binding we examined the binding of mutated forms of tau in which lysine residues 311, 317, and 321 were all converted to glutamine residues (3XKQ) and a form of tau in which lysine residues 311, 217, 321, 340, 343, 347, 353, 369, and 375 are all converted to glutamine residues (9XKQ) (Cooper et al., *J Biol Chem*, (2021), 296: 100715; Rauch et al., *Nature*, (2020), 580: 381-385). Both of these mutant tau molecules displayed weaker binding to LRP1 (Cooper et al., *J Biol Chem*, (2021), 296: 100715). In contrast, the binding of these mutated tau proteins to the SORLA VPS10P domain was only slightly impaired ($K_D$ 3 XKQ mutant=17±12 nM; $K_D$ 9 XKQ mutant=32±2 nM) (FIG. 11$d$).

Collectively, our binding studies show that tau binds the VPS10P domain of SORLA with high affinity, and in contrast to LRP1 the MTB is not the primary binding site for this interaction. Furthermore, modification of lysine residues do not significantly impact this binding interaction.

Figure 12:
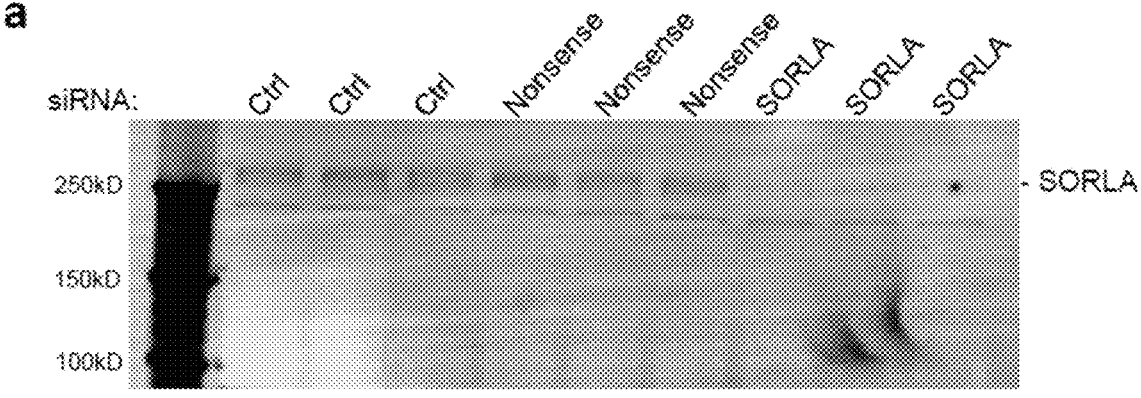
FIG. 12. SORLA knockdown increases tau degradation in H4 cells. H4 cells were treated with siRNA targeting SORL1, then incubated with 20 nM $^{125}$I-labeled tau±1 µM RAP or R2629 for 2 hours. (a) SORLA knockdown confirmed by immunoblot analysis. (b) Internalized and (c) degraded tau was quantified. (Means±SEM; 2-way ANOVA, Tukey's multiple comparison test.
Figure 12:
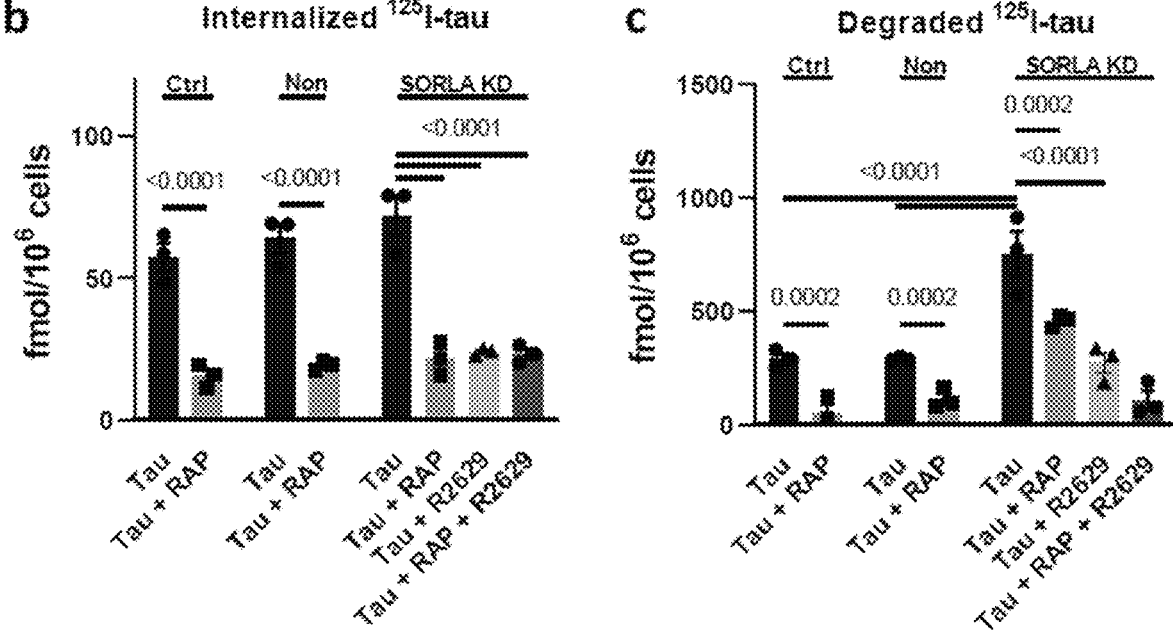

SORLA knockdown in H4 cells results in increased degradation of $^{125}$I-tau. To further investigate the role of endogenously expressed SORLA in a neuronal relevant model, we used siRNA to knock down SORLA in H4 neuroglioma cells and then assessed the internalization and degradation of $^{125}$I-labeled tau. Since these cells also express LRP1, we used an anti-LRP1 IgG to block LRP1 function. Although we observed effective knockdown of SORLA (FIG. 12$a$), we noted no impact on $^{125}$I-tau internalization in the cells lacking SORLA (FIG. 12$b$). Interestingly, cells treated with siRNA targeted to SORLA exhibited a significant increase in the amount of $^{125}$I-labeled tau that was degraded after uptake (FIG. 12$c$). These results reveal that in H4 cells, SORLA functions to sort tau away from the lysosomal degradative pathway.

SORLA provides a mechanism of uptake that supports tau proteopathic seeding in the cytoplasm. SORLA binds tau tightly, and when over-expressed SORLA efficiently mediates tau uptake. A key to understanding SORLA's role in the propagation of tau pathology is the question of whether SORLA-mediated uptake is permissive for tau seeding. To determine if the SORLA-mediated uptake of pathological forms of tau results in tau seeding, we utilized HEK293T FRET biosensor cells that stably express the P301S FRET biosensor and are commonly used to assay tau seeding activity (Holmes et al., *Proc Natl Acad Sci USA*, (2014), 111: E4376-E4385). We conducted experiments in which these cells were transfected with SORLA and incubated with brain lysate from AD patients (FIG. 13$a$) or with HMW SEC fractions isolated from brains of AD patients or healthy age-matched control (FIG. 13$b$) (Dujardin et al., *Nat Med*, (2020), 26: 1256-1263; Takeda et al., *Nat Commun*, (2015) 6: 8490). We found that expression of SORLA in transfected HEK293T biosensor cells results in a significant increase in tau seeding induced by brain lysates or HMW SEC fractions from AD brains.

Figure 13:
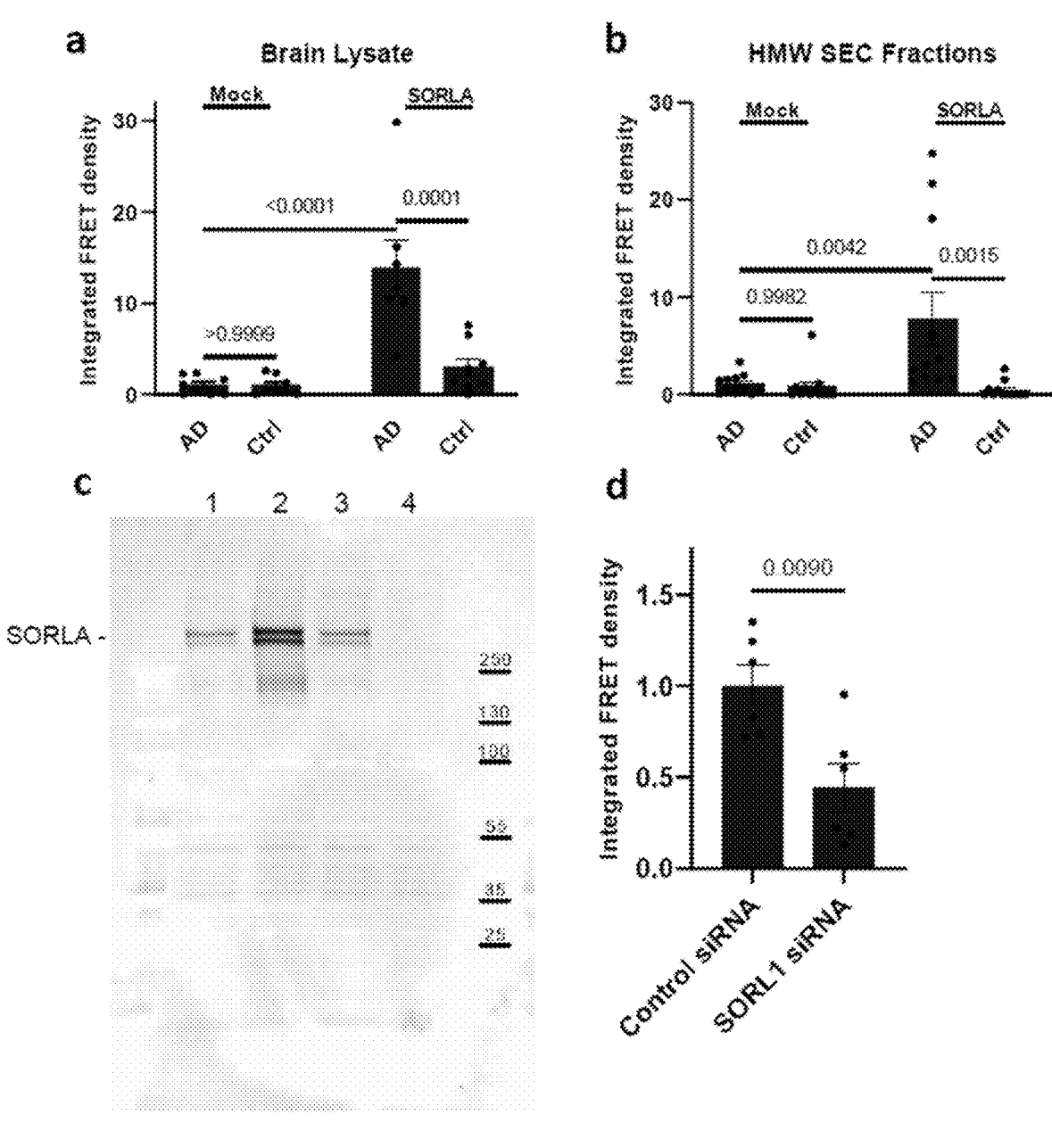
FIG. 13. SORLA transfection reconstitutes pathogenic internalization and seeding in HEK293T reporter cells. HEK293T FRET reporter cells were transfected with SORLA, then incubated with (a) human brain homogenate from an Alzheimer's patient (AD) or age-match healthy control (Ctrl) fraction or (b) HMW SEC fractions from AD patient brain (AD) or healthy control (Ctrl) and tau seeding quantified. (c) siRNA was used to knockdown SORLA in H4 cells and was confirmed by immunoblot analysis, arrow pointing to SORLA band. Lanes: 1) non-transfected, 2) transfected with pcDNA SORLA as positive control, 3) control siRNA, and 4) SORLA siRNA (d) H4 cells stably expressing the FRET reporter system with SORLA knockdown were incubated with 300 ng/well AD brain derived HMW tau seeding material and tau seeding was quantified. (Means±SEM; 2-way ANOVA, Tukey's multiple comparison test).

To determine if SORLA impacts tau seeding when endogenously expressed in a central nervous system relevant model, we used siRNA to knockdown SORLA in H4 neuroglioma cells that stably express the P301S FRET biosensor (FIG. 13$c$). We found that deletion of SORLA in H4 cells significantly reduced tau seeding induced by AD homogenates when compared with cells expressing SORLA. These experiments reveal that SORLA supports the endolysosomal escape of pathological forms of tau resulting in tau seeding.

Figure 14:
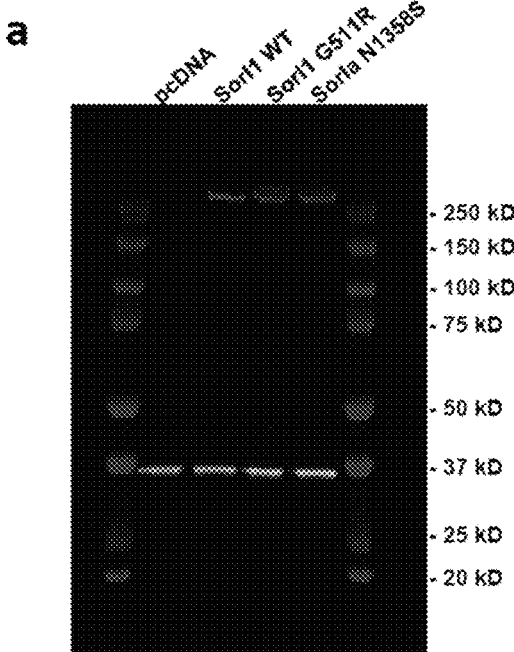
FIG. 14. SORL1 harboring the N1358S mutation exhibits increased seeding capacity in HEK293T cells. HEK293T FRET reporter cells were transfected with plasmid containing WT SORL1 or SORL1 harboring the G511R or N1358S mutations. (a) Expression level of different variants was measured by western blot (GAPDH was used as a loading control). These cells were incubated with (b) HMW or LMW SEC fractions from human AD patient brain or vehicle control and tau seeding was quantified or (c) with 20 nM $^{125}$I-labeled tau in the presence or absence of 1 uM RAP for 2 hours and then internalized tau was quantified. (Means±SEM; 2-way ANOVA, Tukey's multiple comparison test). (c) Transfection efficiency was validated via western blot.
Figure 14:
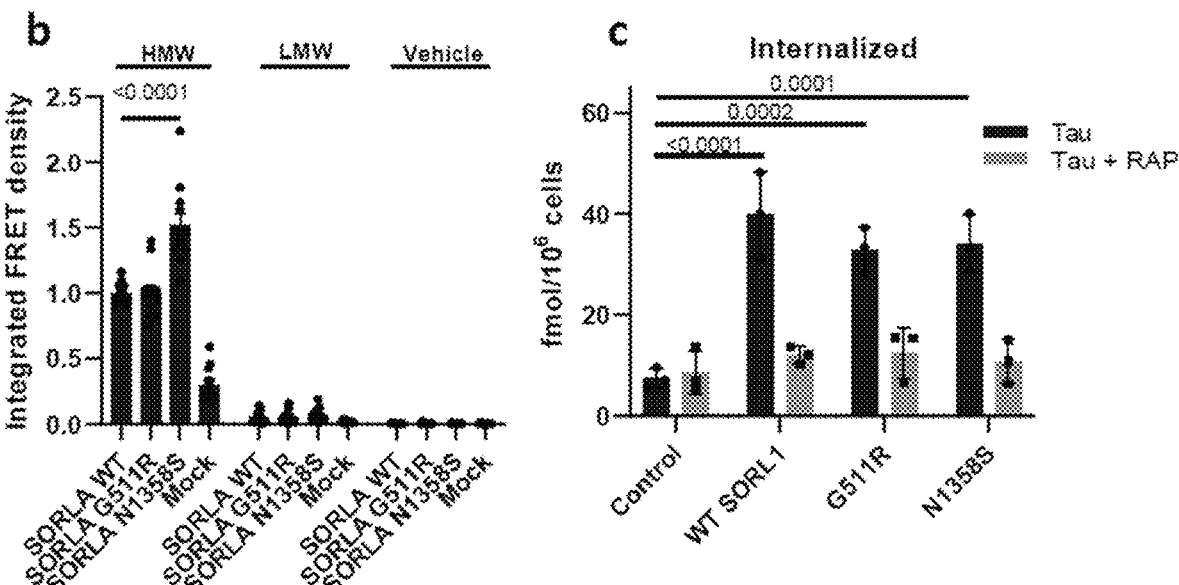

SORLA harboring N1358S mutation exhibits increased tau seeding in HEK293T FRET reporter cells. We next investigated the ability of two SORLA mutations, G511R and N1358S to mediate tau internalization and permit tau seeding. These mutant forms of SORLA were identified by exome sequencing in patients with early onset AD. G511R is located in the VPS10 domain and is known to be deficient in amyloid-beta binding, and N1358S is located in the LDL ligand binding complement-type repeat 7 of SORLA and it is unknown how this mutation affects receptor function (Pottier et al., *Mol Psychiatry*, (2012), 17: 875-879). To investigate the seeding capacity of these mutant forms of tau, HEK293T FRET reporter cells were transfected with plasmid containing WT SORLA or SORLA harboring the G511R or N1358S mutations (FIG. 14$a$), and then incubated with HMW (highly phosphorylated soluble species that support seeding) or LMW (minimally phosphorylated tau species that do not support tau seeding) SEC fractions from AD patient brain or vehicle control (Takeda et al., *Nat Commun*, (2015) 6: 8490). HEK293T biosensor cells transfected with N1358S SORLA showed increased tau seeding as compared to those transfected with WT SORLA when incubated with HMW SEC fractions from AD brains (FIG. 14$b$). In contrast, there were no differences in tau seeding with expression of a second SORLA mutant (G511R) located in the VPS10P domain that impairs the ability of SORLA to bind and to facilitate lysosomal catabolism of Ab (FIG. 14$b$) (Pottier et al., *Mol Psychiatry*, (2012), 17: 875-879; Caglayan et al., *Sci Transl Med*, (2014), 6: 223ra20). To investigate if these changes in tau seeding were associated with increased tau internalization, HEK293T FRET reporter cells transfected with WT, G511R, or N1358S SORLA were incubated with 20 nM $^{125}$I-labeled tau and then internalized tau was quantified. No differences in tau uptake were observed for either mutant (FIG. 14$c$).

Combined, these results suggest that the N1358S mutation leads to increased endolysosomal escape of tau while not impacting tau internalization.

The cellular trafficking of SORLA has revealed that a major function of SORLA is to shuttle ligands between the trans-Golgi network (TGN), endosomes and cell surface (Schmidt et al., *Cell Mol Life Sci*, (2017), 74: 1475-1483). SORLA is predominantly found in early endosomes and in the TGN in most cells (Jacobsen et al., *J Biol Chem*, (2001), 276: 22788-22796; Andersen et al., *Proc Natl Acad Sci USA*, (2005), 102: 13461-13466). SORLA's roles in endocytic sorting have been well-described, and newly synthesized SORLA molecules are transported to the cell surface via the constitutive secretory pathway from the endoplasmic reticulum through the Golgi. These cell surface molecule constitute approximately 10% of the total cell SORLA, and undergo clathrin-dependent endocytosis (Jacobsen et al., *J Biol Chem*, (2001), 276: 22788-22796). The internalized receptors move into endosomal compartments, and are sorted to the TGN, where they shuttle between the TGN and endosomal compartments (Dumanis et al., *J Neurosci*, (2015), 35: 12703-12713; Klinger et al., *J Cell Sci*, (2011), 124: 1095-1105; Glerup et al., *Mol Neurodegener*, (2013), 8: P19 doi:10.1186/1750-1326-8-S1-P19 [PREPRINT]; Herskowitz et al., *Mol Biol Cell*, (2012), 23: 2645-2657; Nielsen et al., *Mol Cell Biol*, (2007), 27: 6842-6851). Interestingly, siRNA knockdown of SORLA in H4 cells, which express both LRP1 and SORLA, revealed that almost all of the tau internalized in these cells is mediated by LRP1, but interestingly, we observed that SORLA knockdown resulted in increased LRP1-mediated tau degradation and decreases cytoplasmic seeding induced by AD brain-derived HMW material containing seeding-competent tau. These results indicate that SORLA mediates the trafficking of tau away from the lysosomal-degradation pathway, increasing the propensity that tau will escape the endolysosomal pathway to allow seeding. Together, the results identify SORLA as a novel receptor for tau that regulates tau internalization, degradation, intracellular sorting, and seeding.

SORLA is implicated in both early and late onset forms of AD. SORLA expression decreases in sporadic AD and polymorphisms in SORLA are associated with early onset familial AD, and late-onset, sporadic AD (Dodson et al., *J Neuropathol Exp Neurol*, (2006), 65: 866-872; Ma et al., *Arch Neurol*, (2009), 66: 448-457; Sager et al., *Ann Neurol*, (2007), 62: 640-647). SORLA can mediate retromer-dependent retrograde trafficking from endosomes to the TGN, as it does for amyloid precursor protein (APP) or anterograde trafficking from the TGN to endosomes (Schmidt et al., *J Biol Chem*, (2007), 282: 32956-32964; Seaman et al., *J Cell Sci*, (2007), 120: 2378-2389; Andersen et al., *Biochemistry*, (2006a), 45: 2618-2628; Fjorback et al., *J Neurosci*, (2012), 32: 1467-1480; Jacobsen et al., *FEBS Lett*, (2002), 511: 155-158; Schmidt et al., *J Biol Chem*, (2007), 282: 32956-32964; Herskowitz et al., *Mol Biol Cell*, (2012), 23: 2645-2657). Thus, in the case of APP, loss of SORLA increases Ab production by increasing its localization in the early endosomes where proteolytic processing can occur (Spoelgen et al. *J Neurosci*, (2006), 26: 418-428; Knupp et al., *Cell Rep*, (2020), 31: 107719). We postulate that SORLA plays a similar role in modulating the trafficking of tau. In this model, loss of normal SORLA decreases SORLA-mediated trafficking of tau to the trans-Golgi resulting in an increase in the amount of tau trafficking along the endolysosomal pathway resulting in increased degradation of tau.

Until now, the impact of the N1358S mutant on SORLA function has not been explored and our finding that SORLA acts as a tau receptor provides a new molecular basis for understanding the genetic association of the SORL1 gene with AD. The N1358S mutant is localized to the cluster of LDL ligand binding repeats, and our results indicate that the N1358S mutation confers increased tau seeding capabilities to SORLA, without impacting the amount of tau internalized. This suggests that deficient intracellular trafficking or endosomal escape may explain the N1358S mutants' deficiency. These results provide insight into the molecular mechanisms by which this tau mutant may impact Alzheimer's disease. In contrast to the N1358S mutant, the G511R tau mutant had no effect on tau uptake or seeding. The G511R mutant is located to the VPS10P domain and SORLA molecules containing this mutation are deficient in Aβ binding, which is speculated to result in increased levels of Ab resulting from reduced lysosomal degradation of Aβ (Caglayan et al., *Sci Transl Med*, (2014), 6: 223ra20).

Our SPR experiments examining the binding of tau to the VPS10P domain of SORLA reveal key differences in the binding of tau when contrasted to that of LRP1. First, posttranslational modifications on tau that are associated with increased AD pathology bind LRP1 less efficiently, but retain affinity for the VPS10P domain of SORLA. Further post-translational modifications of lysine residues that reduce tau binding LRP1 do not impact the tau-VPS10P interaction. Second, the microtubule binding domain of tau binds tightly to LRP1, but only weakly to the VPS10P domain of SORLA. SORLA also contains LDL ligand binding repeats, and it is likely that tau interacts with this region of SORLA as well.

An important remaining question is how internalized tau reaches the cytoplasm to seed intracellular tau aggregation. Endosomal escape of tau appears to be a critical step in the propagation of tau pathology across the brain, enabling internalized tau to seed the aggregation of cytoplasmic tau (Chen et al., *J Biol Chem*, (2019), 294: 18952-18966). Our previous work demonstrated that LRP1 mediates tau internalization and subsequent degradation, and that LRP1-mediated tau uptake permits tau seeding (Cooper et al., *J Biol Chem*, (2021), 296: 100715). While the pathway for LRP1-mediated degradation of ligands is well-defined, it remains unclear how tau escapes the endolysosomal pathway to seed the aggregation of cytoplasmic tau. Endosomal dysfunction has been implicated as a possible early pathway in AD pathogenesis based on both genetics and pathology, with endosomal enlargement observed early in AD. Further, abnormalities in the endo/lysosomal network are prevalent across neurodegenerative disorders (Rogaeva et al., *Nat Genet*, (2007), 39: 168-177; Cataldo et al., *J Pathol*, (2000), 157: 277-286; Karch C M & Goate A M, *Biol Psychiatry*, (2015), 77: 43-51; Offe et al., *J Neurosci*, (2006), 26: 1596-1603; Vagnozzi et al., *Mol Psychiatry*, (2019), 24: 857-868). Previous studies have found that the loss of SORLA results in enlarged endosomes in hiPSC-derived neurons and alters APP localization within the endosomal network (Knupp et al., *Cell Rep*, (2020), 31: 107719). Our finding that SORLA impacts tau trafficking and can mediate tau seeding suggests that it is also involved in the endosomal trafficking and potentially escape of tau.

Both LRP1 and SORLA modulate amyloid precursor protein (APP) trafficking and amyloid-beta (Aβ) production and clearance: LRP1 interacts with APP and modulates Ab production, while SORLA impairs amyloidogenic processes by sorting APP between endosomes and the TGN, impacting APP processing, and Aβ production and lysosomal targeting (Kounnas et al., *Cell*, (1995), 82: 331-340; Ulery et al., *J Biol Chem*, (2000), 275: 7410-7415; Pietrzik et al., *EMBO*

J, (2002), 21: 5691-5700; Andersen et al., *Proc Natl Acad Sci USA*, (2005), 102: 13461-13466; Knupp et al., *Cell Rep*, (2020), 31: 107719). Furthermore, Aβ is also a ligand for SORLA as well as LRP1 (Urmoneit et al., *Lab Invest*, (1997), 77: 157-166; Caglayan et al., *Sci Transl Med*, (2014), 6: 223ra20; Shibata et al., *J Clin Invest*, (2000), 106: 1489-1499; Storck et al., *J Clin Invest*, (2015), 126: 1-14). LRP1 and SORLA interact through their respective luminal domains and cytoplasmic tails, and in primary neurons localize to perinuclear compartments (Spoelgen et al., *Neuroscience*, (2009), 158: 1460-1468). LRP and SORLA also interact directly with beta secretase, the APP processing enzyme BACE, whose degradation may depend on retromer dependent sorting (Andersen et al., *J Neurosci*, (2006b), 45: 1460-1468; Koh et al., *J Biol Chem*, (2005), 280: 32499-32504). Additionally, LRP1 and SORLA are both neuronal apolipoproteinE (apoE) receptors, and through this action mediate cholesterol uptake into neurons (Carlo et al., *J Neurosci*, (2013), 33: 358-370; Liu et al., *Neuron*, (2007), 56: 66-78).

Figure 15:
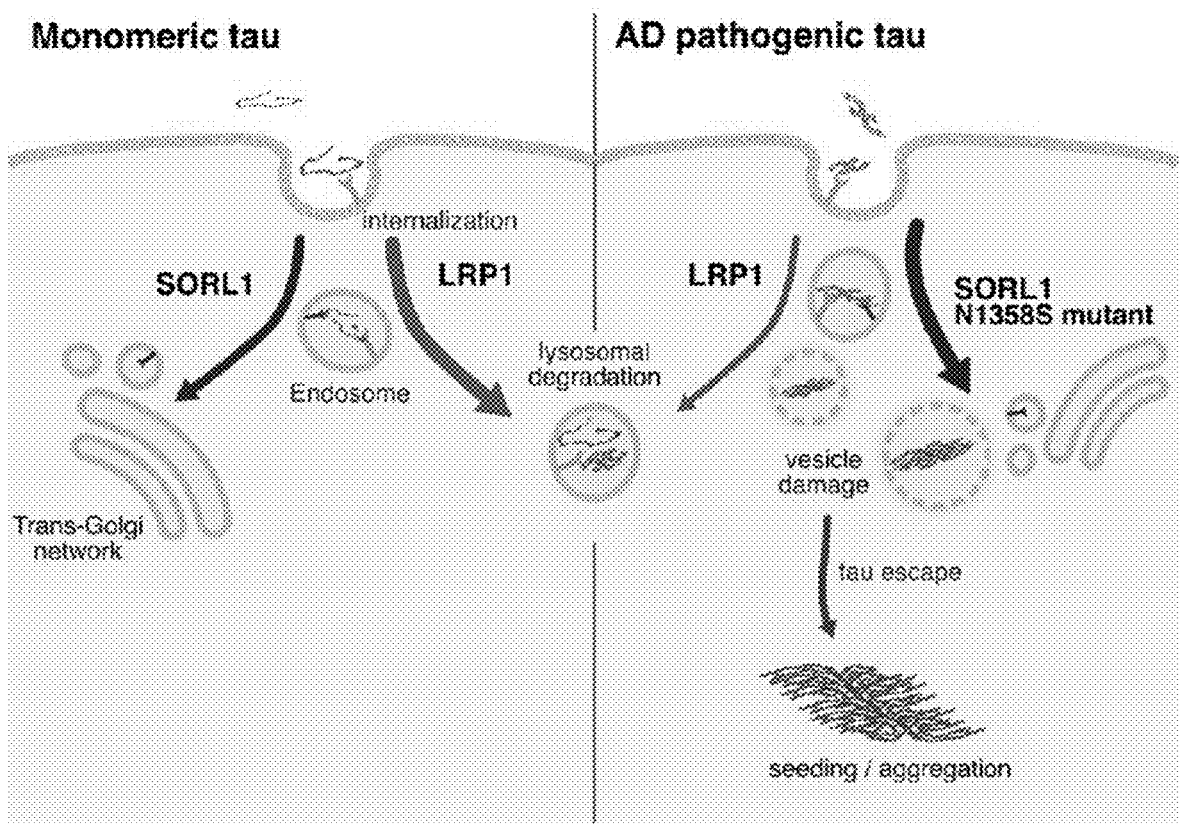
FIG. 15. Model of LRP1 and SORLA-mediated tau trafficking. LRP1 mediates the internalization of monomeric forms of tau, resulting in rapid and efficient tau degradation. SORLA serves as a sorting receptor that facilitates trafficking of tau through the endosomal pathway. We postulate that this pathway allows for rapid and efficient degradation of monomeric tau. However, AD pathogenic tau escapes this pathway to reach the extracellular space where it can induce cytoplasmic seeding. Furthermore, the AD-associated N1358S mutation in SORLA increases the propensity of tau to seed aggregation, likely through impacting tau intracellular trafficking.

We propose that LRP1 functions as a primary receptor for tau endocytosis, internalizing tau and then directing it to lysosomal pathways for degradation. Simultaneously, SORLA acts as a sorting receptor for tau, potentially removing tau away from lysosomal pathways to the TGN. Disruption of tau trafficking could lead to aberrant accumulation of tau in endosomal compartments, and thus enable increased endosomal escape (FIG. 15). Careful studies on tau trafficking mediated by LRP1 and SORLA are required to reveal mechanisms of endosomal escape by tau.

In conclusion, our studies confirm the existence of multiple pathways for mediating the endocytosis and cellular trafficking of tau. In addition, we identified SORLA as a second receptor that binds and internalizes tau and promotes tau seeding. These data put several molecules of clear import in AD pathophysiology—LRP, apoE, SORLA, and tau— into a single molecular pathway involving uptake of pathological tau, and seeded aggregation of intracytoplasmic tau.

Materials and Methods

Cells. CHO K1 (WT CHO) and CHO 13-5-1 cells were maintained in Dulbecco's modified Eagle medium/Ham's F12 with L-glutamine (DMEM/F12; Corning 10-090-CM) supplemented with 10% fetal bovine serum (FBS; Sigma F-4135) (FitzGerald et al., *J Cell Biol*, (1995), 129: 1533-1541). The Tau RD P301S FRET Biosensor embryonic kidney 293T cells (ATCC CRL-3275) provided by Marc Diamond were maintained in DMEM supplemented with 10% FBS. H4 neuroglioma cells (HTB-148™) where purchased from American Type Culture Collection (ATCC) and were maintained in DMEM supplemented with 10% FBS. H4 cells were stably transduced with a lentivirus encoding a FRET-based tau probe comprising the 344 to 378 residues of human P301L mutant tau fused to mTurquoise2, a self-cleaving 2A peptide, and 344 to 378 of human P301L mutant tau fused to mNeonGreen. All cells were cultured with 1× penicillin-streptomycin (Corning 30-002-CI) and maintained at 37° C. and 5% CO2 in a humidified atmosphere. Proteins, antibodies, and plasmids. RAP was expressed in *E. coli* (Williams et al., *J Biol Chem*, (1992), 267: 9035-9040). Full-length tau (2N4R; SP-495) and tau microtubule binding domain (MBD; SP-496, Leu243-Glu372) were purchased from R&D Systems. His-tagged recombinant human tau variants 2N4R, ON3R, 2N3R, and mutated tau proteins were expressed in *E. coli* and purified. His-tagged phosphorylated 2N4R tau was produced in SF9 cells. Cells were not treated with phosphatase inhibitor during production, resulting in an intermediate tau phosphorylation state (Tepper et al., *J Biol Chem*, (2014), 289: 34389-34407). 10×175-cm2 SF9 cells with 80 to 90% confluency were infected with P3 or P4 recombinant baculovirus (MOI 5-10) and incubated at 27° C. for 48 to 72 h. Cells were pelleted at 500 g for 5 min and resuspended in 30 ml lysis buffer containing 50 mM Tris-HCl, 100 mM NaCl, 10% glycerol, 5 mM imidazole, 0.5 mM tris(2-carboxyethyl)phosphate, 0.1 mM PMSF, benzonase 30 U/ml, and 1× Halt protease, and phosphatase inhibitor cocktail (Thermo Scientific 1861282). Cells were crushed in a French press twice, suspension was boiled for 20 min in a 100° C. water bath, cooled down on ice for 15 min, and centrifuged at 15,000 g for 30 min to remove debris. Lysate was run on a HisTrap affinity column, and collected fractions were dialyzed into PBS containing 0.5 mM tris(2-carboxyethyl)phosphate. His tag was removed by enzymatic cleavage. 2N4R tau harboring the 6A or 6E mutations was generated by converting T181, S199, S202, S396, S400, and S404 to alanine (6A mutant) or glutamic acid (6E mutant). 3XKQ and 9XKQ 2N4R tau were generated in *E. coli* by mutating lysine residues 311, 317, and 321 or lysine residues 311, 217, 321, 340, 343, 347, 353, 369, and 375 to glutamine residues. Mouse anti-SORLA antibody was purchased from BD Biosciences (BD Transduction Laboratories™, 611860). Chicken anti-GAPDH was obtained from Abcam (ab83956). SORLA plasmid was provided by Clause Petersen, Aarhus University, Sweeden (pcDNA3.1/zeo SORLA Fl) (Jacobsen et al., *J Biol Chem*, (2001), 276: 22788-22796). SORLA G511R and N1358S plasmids were prepared by mutating the WT SORLA plasmid, mutants were generated by VectorBuilder. Recombinant Human SORLA VPS10 domain containing aa 82-753 was purchased from R&D Systems (9880-LA). The rabbit anti-LRP1 polyclonal (R2629) antibody was used to inhibit ligand binding to LRP1 as previously described (Strickland et al., *J Biol Chem*, (1990), 265: 17401-17404).

Tau internalization and degradation assays. Cellular internalization assays were conducted as previously described (Ulery et al., *J Biol Chem*, (2000), 275: 7410-7415; FitzGerald et al., *J Cell Biol*, (1995), 129: 1533-1541; Cooper et al., *J Biol Chem*, (2021), 296: 100715). Twelve-well culture dishes were seeded with CHO ($2 \times 10^5$ cells per well), HEK293T FRET reporter ($1 \times 10^5$ cells per well) cells, or H4 cells ($0.5 \times 10^5$ cells per well). Cells were cultured overnight in DMEM (H4 and HEK293T) or DMEM/F12 (CHO) with 10% FBS without antibiotic. The following day, cells were transfected with plasmids containing SORLA or siRNA to knockdown SORLA as described below. All transfections were incubated for 24 hours and siRNA incubated for 48 hrs. After transfection or knockdown, cells were incubated in assay media (DMEM supplemented with 1.5% bovine serum albumin and 20 mM HEPES) for 1 h and then incubated with assay media containing 20 nM $^{125}$I-labeled tau (2N4R; R&D Systems, Inc; SP-495) in the presence or absence of 1 μM RAP for specified times. In some experiments LRP1 was inhibited by co-incubation with 300 μg/ml R2629 anti-LRP1 antibody.

Transfections. 24 hours after plating, cells were transfected with plasmid containing the SORLA gene, or SORLA harboring the G511R or N1358S mutant using 0.75 μg DNA per well via PEI transfection reagent at a ratio of 6 μl PEI:1 μg DNA. Transfection with empty vector was used as control. Cells were incubated with transfection reagent for 10 hours during the day, then media was replaced with antibiotic free media supplemented with 10% FBS and incubated overnight. 24 h after transfection, the tau internalization assay was performed as described previously. Transfection efficiency was confirmed via Western blot.

siRNA knockdown. For tau uptake assays, H4 cells were plated at $0.5 \times 10^5$ cells/well on a 12 well culture dish in DMEM+10% FBS without antibiotic. The following day, cells were incubated with 25 nM ON-TARGETplus siRNA SMARTpool human SORLA (Horizon™ L-004722-00-0005) or ON-TARGETplus Non-targeting Control Pool (Horizon™ D-001810-10-05) using 2 µL per well of DharmaFECT™ 1 Transfection Reagent (Horizon™ T-2001). Cells were incubated with siRNA for 48 hours, and then media was replaced with assay media for tau uptake assays. Knockdown efficiency was confirmed via western blot. For tau seeding assay in H4 reporter line, cells were plated at $10^4$ cells/well in a 96 well plate. The next day, cells were transfected with 25 nM siRNA using 0.5 µL Lipofectamine™ 3000 Transfection Reagent (Invitrogen™ L3000015) per well in culture medium (in DMEM supplemented with 10% FBS). Tau seeds were added 24 hours after transfection and incubated for 48 hours.

SPR. Binding of tau isoforms 2N4R, 2N3R, and 2N4R tau harboring the 6A, and 6E mutations, hyperphosphorylated 2N4R tau produced in Sf9 cells, 3XKQ, 9XKQ, E20Q3, and E7Q2 tau SORLA VPS10P were assessed using a Biacore 3000 optical biosensor system (GE Healthcare Life Sciences) essentially as described (Migliorini et al., *J Biol Chem*, (2020), 295: 212-222; Cooper et al., *J Biol Chem*, (2021), 296: 100715). Single cycle titrations were performed by serial injections from low to high concentration (3.8, 11.5, 34.4, 103.3, and 310 nM) with a 3.5-min injection time. Between sample runs, sensor chip surfaces were regenerated with 15-s injections of 100 mM phosphoric acid (pH~2.5) at a flow rate of 100 µl/min.

Kinetic analysis of SPR data. Single cycle titration data were analyzed by fitting the titration to a 1:1 interaction model or by an equilibrium fit of the individual data to a pseudo-first-order process to obtain values of Req for each concentration, then the Req values were plotted as a function of total concentration of tau (Karlsson et al., *Anal Biochem*, (2006), 349: 136-147). These equilibrium data were fit to a binding model using non-linear regression analysis available in GraphPad vs 9.

Tau seeding FRET biosensor assay. Human brain homogenates were prepared from an AD Braak VI brain and one healthy control brain from the Massachusetts Alzheimer's Disease Research Center Brain Bank. Briefly, 100 mg of frontal cortex tissue (Brodmann area 8/9) were thawed and homogenized in 500 µl of PBS with protease inhibitor (Roche) by 30 up and down strokes in a glass Dounce homogenizer. The homogenate was centrifuged at 10,000 g for 10 min at 4° C. The supernatant was aliquoted, and a bicinchoninic acid assay (Thermo Scientific Pierce) was performed according to manufacturer's instructions to quantify total protein concentration. Soluble HMW-SEC tau was isolated from homogenate using size exclusion chromatography on a Superdex200 10/300GL column (#17-5175-01; GE Healthcare) as described previously (Takeda et al., *Nat Commun*, (2015) 6: 8490). Total tau concentration was measured by western blot using a rabbit polyclonal anti-human tau antibody (A0024, Dako) and serial dilutions of recombinant tau 441 (Sigma-Aldrich, T0576). The Tau RD P301S FRET Biosensor 293T cells (ATCC CRL-3275) were reverse transfected in Costar Black (Corning) clear bottom 96-well plates, using 0.3 uL/well trans-IT X2 reagent (Mirus) in 10 uL/well Opti-MEM according to manufacturer's protocol with 100 ng/well empty pcDNA3 plasmid (mock condition) or pcDNA3 plasmid encoding for the WT, G511R, N1358S SORL1 proteins. $6 \times 10^5$ cells/well were seeded in a final volume of 100 uL. After 24 hours, transfection medium was removed, cells were washed with sterile PBS and incubated with 300 ng/well tau diluted in Opti-MEM (final volume 50 uL). The next day. Each condition was tested at least in quadruplicate. The following day, cells were collected using trypsin and transferred into 96-well U-bottom plates (Corning) using 10% FBS culture media to neutralize trypsin. Cells were pelleted at 1200 g for 10 min, resuspended in cold 2% paraformaldehyde for 10 min, pelleted at 1200 g, and resuspended in 200 µl of PBS. Samples were run on the MACS Quant VYB (Miltenyi) flow cytometer for the quantification of CFP and FRET. Tau seeding was quantified by multiplying the percent of FRET-positive cells by the median fluorescence intensity of those cells, as described previously (DeVos et al., *Front Neurosci*, (2018), 12: 1-15). About 40,000 cells per well were analyzed. Data were analyzed using FlowJo software (BD Biosciences). For the seeding assay performed in stable H4 reporter line, 15'000 cells/well were plated.

SDS-PAGE and Western blot. Cell cultures were collected in radioimmunoprecipitation assay lysis buffer and analyzed by Western blotting as previously described (Cooper et al., *J Biol Chem*, (2021), 296: 100715). Equal amounts of protein from each sample were mixed with loading buffer with or without 100 mM/l dithiothreitol, boiled for 5 min, resolved by electrophoresis on a Novex 4 to 12% Tris-Glycine Mini Protein Gel, and transferred to polyvinylidene difluoride membranes for Western blot analysis. Membranes were blocked with Odyssey blocking buffer and incubated with anti-SORLA antibody at a concentration of 1:1000 or anti-GAPDH 1:1000 overnight at 4° C. The membrane was washed three times with 0.05% Tween-20 in Tris-buffered saline, and the antibody binding to membrane was detected with IRDye 680RD or 800 anti-mouse, anti-rabbit or anti-chicken IgG secondary antibody (LI-COR Biosciences) at a concentration of 1:10,000. The membrane was then washed three times with 0.05% Tween-20 in Tris-buffered saline and imaged using a LI-COR Odyssey Infrared Imaging System.

Experimental design and statistical analysis. All results are represented as mean±SEM or SD, as indicated. Data were analyzed for significance using one-way ANOVA, or two-way ANOVA, with Tukey's multiple comparisons post-tests, as indicated using GraphPad vs 9 software. A p value of <0.05 was set as the threshold for significance.

Example 6. LRP1 Binding to HMW or LMW SEC Fractions Isolated from Alzheimer's Disease (AD) or Age-Matched Control (CT) Human Brains In Alzheimer's disease the one of the pathological hallmarks is the accumulation of neurofibrillary tangles, which contain highly post-translationally modified and aggregated tau protein (MAPT). LRP1 was identified as a major endocytic receptor for tau that mediates tau spreading, uptake, degradation, and seeding. We identified high affinity binding between tau and LRP1 and found that phosphorylation of specific lysine residues on tau reduces its binding affinity to LRP1. These studies used recombinantly produced monomeric forms of tau, and an important remaining question is whether LRP1 binds the highly post-translationally modified and aggregated forms of tau found in Alzheimer's disease patients.

Figure 16:
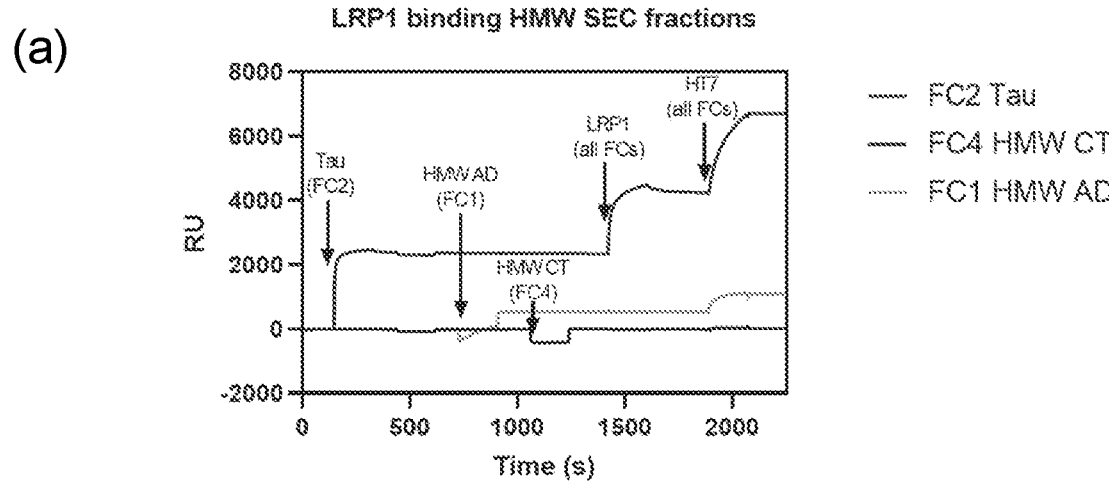
FIG. 16. LRP1 binding to HMW or LMW SEC fractions isolated from Alzheimer's disease (AD) or age-matched control (CT) human brains. Tau 13 antibody was immobilized on the surface of a CM5 sensor chip, and then recombinant tau, HMW SEC fractions (a), or LMW SEC fractions (b) from AD vs CT patient brain extract were flowed over individual flow cells. (a&b) 300 nM LRP1 was then flowed over all FCs, followed by a second tau antibody (HT7) to confirm tau capture. (c) HMW and LMW SEC fractions from AD or CT patient brain extract were captured to the surface of a CM5 sensor chip using the Tau13 antibody, and then increasing concentrations (denoted on graph with arrows at approximate injection start time) were
Figure 16:
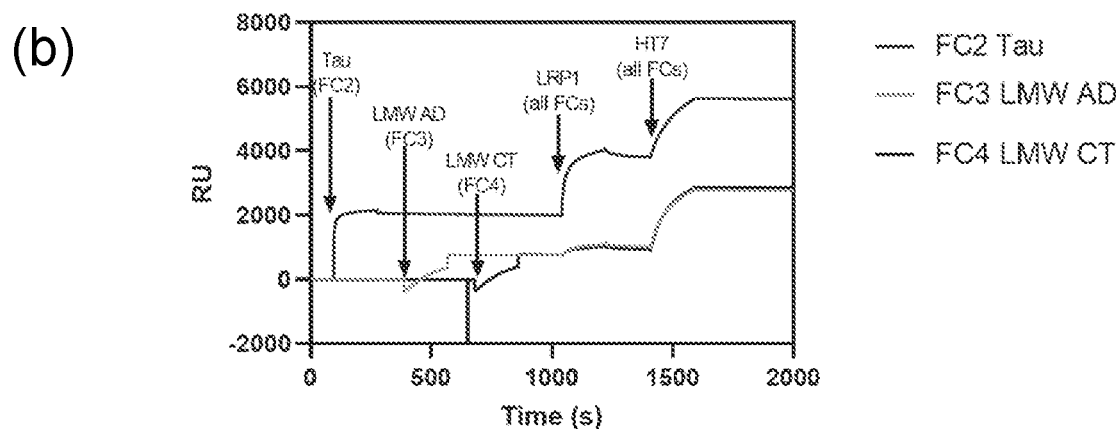
Figure 16:
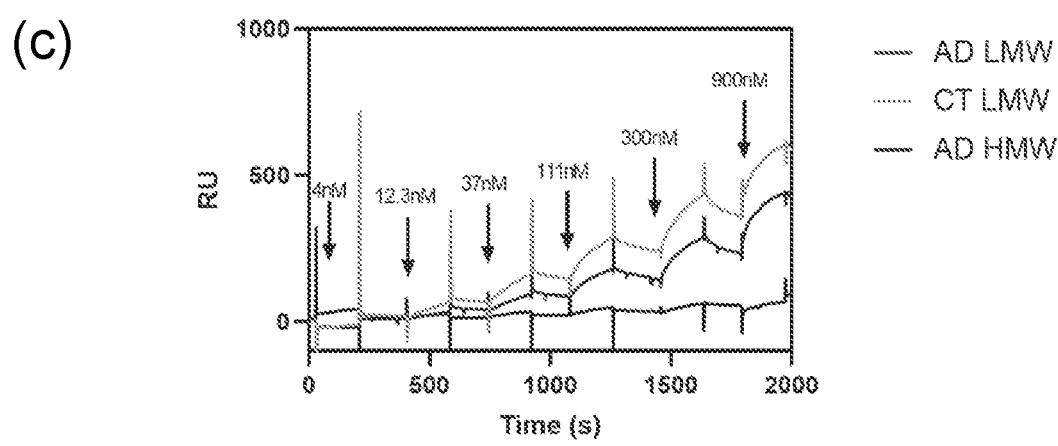

We have developed a surface plasmon resonance (SPR)-based capture assay to investigate the binding of LRP1 to tau isolated from extracts of Alzheimer's disease patient brains. We use amine coupling to immobilize the anti-tau antibody (Tau13) on a CM5 SPR sensor chip, and then flow human brain extracts from Alzheimer's disease patients or age-matched cognitively normal control individuals over the chips. We compared fractions containing high molecular weight (HMW) or low molecular weight (LMW) tau iso- [5] lated by size exclusion chromatography (SEC). The Tau13 antibody stably captures tau from these extracts on the SPR sensor chip surface, allowing us to assess the binding of various concentrations of full-length human LRP1 isolated from placenta to the captured tau. We confirm tau capture by [10] assessing binding of second anti-tau antibody, HT7. This assay allows us to investigate the binding of LRP1 to HMW and LMW tau isolated from patient brains, and we can use this assay to screen for peptide, antibody, or small-molecule inhibitors of the LRP1/tau binding interaction by simulta-neously injecting them with LRP1 to determine if they inhibit LRP1 binding. Our results demonstrate that LRP1 binds. See FIG. 16.

While the present teachings are described in conjunction with various embodiments, it is not intended that the present teachings be limited to such embodiments. On the contrary, the present teachings encompass various alternatives, modi-fications, and equivalents, as will be appreciated by those of skill in the art.

---

What is claimed is:

1. A method of reducing tau internalization and/or trafficking in neuronal cells to treat Alzheimer's disease in a subject, comprising contacting the neuronal cells of the subject with i) an effective amount of a SorLA antagonist; or ii) an effective amount of an LRP1 antagonist and a SorLA antagonist, wherein the SorLA antagonist is an siRNA and the LRP1 antagonist is receptor associated protein (RAP) or a fragment thereof comprising the D3 domain.

2. The method of claim 1, wherein the LRP1 antagonist is receptor associated protein (RAP).

3. The method of claim 1, wherein the effective amount of a SorLA antagonist or the effective amount of an LRP1 antagonist and the SorLA antagonist are administered to the subject intrathecally and/or intraventricularly.

4. The method of claim 1, wherein the siRNA targets a portion of SorLA mRNA corresponding to SEQ ID NO:2.

5. The method of claim 1, wherein the siRNA has a target sequence comprising any of SEQ ID NOS:5-8.

6. The method of claim 1, wherein the siRNA has a target sequence comprising SEQ ID NO:5.

7. The method of claim 1, wherein the siRNA has a target sequence comprising SEQ ID NO:6.

8. The method of claim 1, wherein the siRNA has a target sequence comprising SEQ ID NO:7.

9. The method of claim 1, wherein the siRNA has a target sequence comprising SEQ ID NO:8.

*     *     *     *     *